(12) United States Patent
Neumann

(10) Patent No.: US 12,079,714 B2
(45) Date of Patent: Sep. 3, 2024

(54) METHODS AND SYSTEMS FOR AN ARTIFICIAL INTELLIGENCE ADVISORY SYSTEM FOR TEXTUAL ANALYSIS

(71) Applicant: Kenneth Neumann, Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 896 days.

(21) Appl. No.: 16/502,797

(22) Filed: Jul. 3, 2019

(65) Prior Publication Data
US 2021/0005316 A1     Jan. 7, 2021

(51) Int. Cl.
| | | |
|---|---|---|
| *G06F 16/30* | (2019.01) | |
| *G06F 16/9032* | (2019.01) | |
| *G06N 3/08* | (2023.01) | |
| *G06N 20/00* | (2019.01) | |
| *G16H 50/20* | (2018.01) | |

(Continued)

(52) U.S. Cl.
CPC ......... *G06N 3/08* (2013.01); *G06F 16/90332* (2019.01); *G06N 20/00* (2019.01); *G16H 50/20* (2018.01); *G16H 50/70* (2018.01); *G06F 40/205* (2020.01)

(58) Field of Classification Search
CPC .............. G16H 50/70; G06F 16/90332; G06F 40/205; G06F 3/04812; G06F 3/0484; G06F 3/0482; G06F 3/0488; G06N 20/00; G06N 3/08; G06N 20/20; G06N 40/30; G06N 5/02; G06N 3/004; G06N 3/0454; G06N 7/005; A63B 24/0062; A63B 24/0075; A63B 2024/0065; A63B 2024/0081
See application file for complete search history.

(56) References Cited

U.S. PATENT DOCUMENTS

| | | |
|---|---|---|
| 9,185,238 B1 | 11/2015 | Freeland et al. |
| 9,600,297 B1 | 3/2017 | Buyukkokten |
| 9,948,689 B2 | 4/2018 | Savage et al. |

(Continued)

OTHER PUBLICATIONS

Han, Qiwei, et al. "A hybrid recommender system for patient-doctor matchmaking in primary care." 2018 IEEE 5th International Conference on Data Science and Advanced Analytics (DSAA). IEEE, 2018. (Year: 2018).*
Online spiritual advisor services; http://www.askforadvisors.com/psychic-readings/index.php; Apr. 22, 2019.
24 Astro Spiritual Advisor; https://play.google.com/store/apps/details?id=infrasat.astro24; Feb. 18, 2019.
Chatnow; https://chatnow.org/; Apr. 22, 2019.

*Primary Examiner* — Polina G Peach
(74) *Attorney, Agent, or Firm* — Caldwell Intellectual Property Law

(57) ABSTRACT

In an aspect, an artificial intelligence advisory system for textual analysis. The system includes at least a server configured to receive at least a user datum from a user client device. The system includes an advisory module operating on the at least a server configured to receive at least an advisory input from an advisor client device and generate at least an advisory instruction set as a function of the at least a user input datum and the at least an advisory input. The system includes an artificial intelligence advisor operating on the at least a server configured to generate at least a textual output as a function of the at least an advisory instruction set and the at least a user input datum and receive at least a user input as a function of the at least a textual output.

20 Claims, 23 Drawing Sheets

(51) Int. Cl.
*G16H 50/70* (2018.01)
*G06F 40/205* (2020.01)

(56) References Cited

U.S. PATENT DOCUMENTS

| | | | |
|---|---|---|---|
| 9,965,553 B2 | 5/2018 | Lyren | |
| 9,996,666 B1* | 6/2018 | Wilson | G06F 16/9537 |
| 10,168,866 B2 | 1/2019 | Wakeen | |
| 10,445,354 B2* | 10/2019 | Houser | G06F 16/3344 |
| 11,031,109 B2* | 6/2021 | Devarakonda | G06F 3/0482 |
| 11,205,516 B2* | 12/2021 | Lieberman | G06N 3/045 |
| 2006/0205564 A1* | 9/2006 | Peterson | A63B 69/00 482/8 |
| 2008/0319796 A1* | 12/2008 | Stivoric | A61B 5/7475 705/2 |
| 2009/0048903 A1 | 2/2009 | Lieberman | |
| 2010/0179930 A1* | 7/2010 | Teller | G06N 20/00 706/12 |
| 2010/0241454 A1* | 9/2010 | Firminger | G16H 50/20 715/833 |
| 2011/0119072 A1* | 5/2011 | Lipner | G06Q 10/10 705/2 |
| 2012/0096089 A1* | 4/2012 | Barash | H04L 67/61 709/204 |
| 2013/0174058 A1* | 7/2013 | Kaul | H04M 3/42382 715/753 |
| 2014/0276244 A1* | 9/2014 | Kamyar | A61B 5/1112 600/595 |
| 2014/0310013 A1* | 10/2014 | Ram | G16H 50/20 705/2 |
| 2014/0324457 A1* | 10/2014 | Kim | G16H 50/20 705/3 |
| 2015/0006192 A1* | 1/2015 | Sudharsan | G16H 50/20 705/2 |
| 2015/0032724 A1* | 1/2015 | Thirugnanasundaram | G06Q 30/01 707/722 |
| 2015/0294595 A1* | 10/2015 | Hu | G06Q 10/101 434/236 |
| 2016/0085923 A1* | 3/2016 | Lacombe | G06Q 50/265 705/2 |
| 2016/0110657 A1* | 4/2016 | Gibiansky | G06N 20/00 706/12 |
| 2016/0162785 A1 | 6/2016 | Grobman | |
| 2016/0212076 A1 | 7/2016 | Bellissimo et al. | |
| 2016/0250751 A1* | 9/2016 | Martinson | G16H 10/60 700/253 |
| 2016/0314265 A1* | 10/2016 | Sternberg | G06F 40/20 |
| 2016/0360466 A1* | 12/2016 | Barak | H04W 76/10 |
| 2017/0039502 A1* | 2/2017 | Guman | G06Q 10/06393 |
| 2017/0185581 A1* | 6/2017 | Bojja | G06V 30/19173 |
| 2017/0213138 A1* | 7/2017 | Bojja | G06N 20/00 |
| 2017/0235849 A1 | 8/2017 | Jacob | |
| 2017/0272455 A1* | 9/2017 | Black | H04W 12/065 |
| 2018/0108272 A1* | 4/2018 | Ahmad | G06N 5/02 |
| 2018/0113986 A1* | 4/2018 | Zhu | G16H 10/60 |
| 2018/0121619 A1* | 5/2018 | Perlroth | G16H 40/20 |
| 2018/0160904 A1* | 6/2018 | Saenz | A61B 5/0002 |
| 2018/0165588 A1* | 6/2018 | Saxena | G06N 5/043 |
| 2018/0189728 A1* | 7/2018 | Jones | G06Q 30/0222 |
| 2018/0260860 A1* | 9/2018 | Devanathan | G06F 16/353 |
| 2018/0308128 A1* | 10/2018 | DeLuca | H04L 67/306 |
| 2019/0027052 A1 | 1/2019 | Moore | |
| 2019/0066849 A1* | 2/2019 | Lawrence | G06F 40/205 |
| 2019/0244175 A1* | 8/2019 | Ogrinz | G06Q 10/063 |
| 2019/0304000 A1* | 10/2019 | Simpson | G01N 33/48792 |
| 2020/0077942 A1* | 3/2020 | Youngblood | A61B 5/4884 |
| 2020/0162600 A1* | 5/2020 | Lau | H04M 1/27453 |
| 2020/0183928 A1* | 6/2020 | Wu | G06N 5/022 |
| 2020/0242964 A1* | 7/2020 | Wu | G06F 16/90332 |

\* cited by examiner

METHODS AND SYSTEMS FOR AN ARTIFICIAL INTELLIGENCE ADVISORY SYSTEM FOR TEXTUAL ANALYSIS

FIELD OF THE INVENTION

The present invention generally relates to the field of artificial intelligence. In particular, the present invention is directed to methods and systems for an artificial intelligence advisory system for textual analysis.

BACKGROUND

Accurate analysis of textual responses can be challenging due to the complexity of text to be analyzed in addition to large quantities of text that exists. Knowing what data to analyze and what data to accurately transmit can be highly complex. Incorrect textual analysis can lead to inaccuracies and ultimately frustrate users.

SUMMARY OF THE DISCLOSURE

In an aspect, an artificial intelligence advisory system for textual analysis. The system includes at least a server. At least a server is configured to receive at least a user input datum from a user client device. The system includes an advisory module operating on the at least a server, wherein the advisory module is configured to receive at least an advisory input from an advisor client device; and generate at least an advisory instruction set as a function of the at least a user input datum and the at least an advisory input. The system includes an artificial intelligence advisor operating on the at least a server, wherein the artificial intelligence advisor is configured to generate at least a textual output as a function of the at least an advisory instruction set and the at least a user input datum; and receive at least a user input as function of the at least a textual output.

In another aspect, a method of an artificial intelligence advisory system for textual analysis includes receiving by at least a server at least a user input datum from a user client device. The method includes receiving at least an advisory input from an advisor client device. The method includes generating at least an advisory instruction set as a function of the at least a user input datum and the at least an advisory input. The method includes generating at least a textual output as a function of the at least an advisory instruction set and the at least a user input datum. The system includes receiving at least a user input as a function of the at least a textual output.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for artificial intelligence advisory system for textual analysis. In an embodiment, at least a server receives at least a user input datum from a user client device. In an embodiment, at least a user input datum contains a request for spiritual guidance, or a request to develop a spiritual practice such as a daily meditation practice. At least a server receives at least an advisory input from an advisor client device. In an embodiment, at least an advisory input may include information from an informed advisor such as a spiritual teach or instructor containing advice for user pertaining to user's input datum. At least a server generates at least an advisory instruction set as a function of the at least a user input datum and the at least an advisory instruction set. At least a server generates at least a textual output as a function of the at least an advisory instruction set and the at least a user input datum. In an embodiment, at least a textual output may include words of encouragement or support for a user pertaining to user's input datum. For example, a user input datum containing a request to develop a daily spiritual practice may receive at least a textual output containing daily reminders and words of encouragement for user to engage in user's spiritual practice. At least a server receives at least a user input as a function of the at least a textual output. At least a user input may include reflections and feedback from user in reference to textual output. User input may be utilized to updated textual output and/or advisory instruction set.

Figure 1:
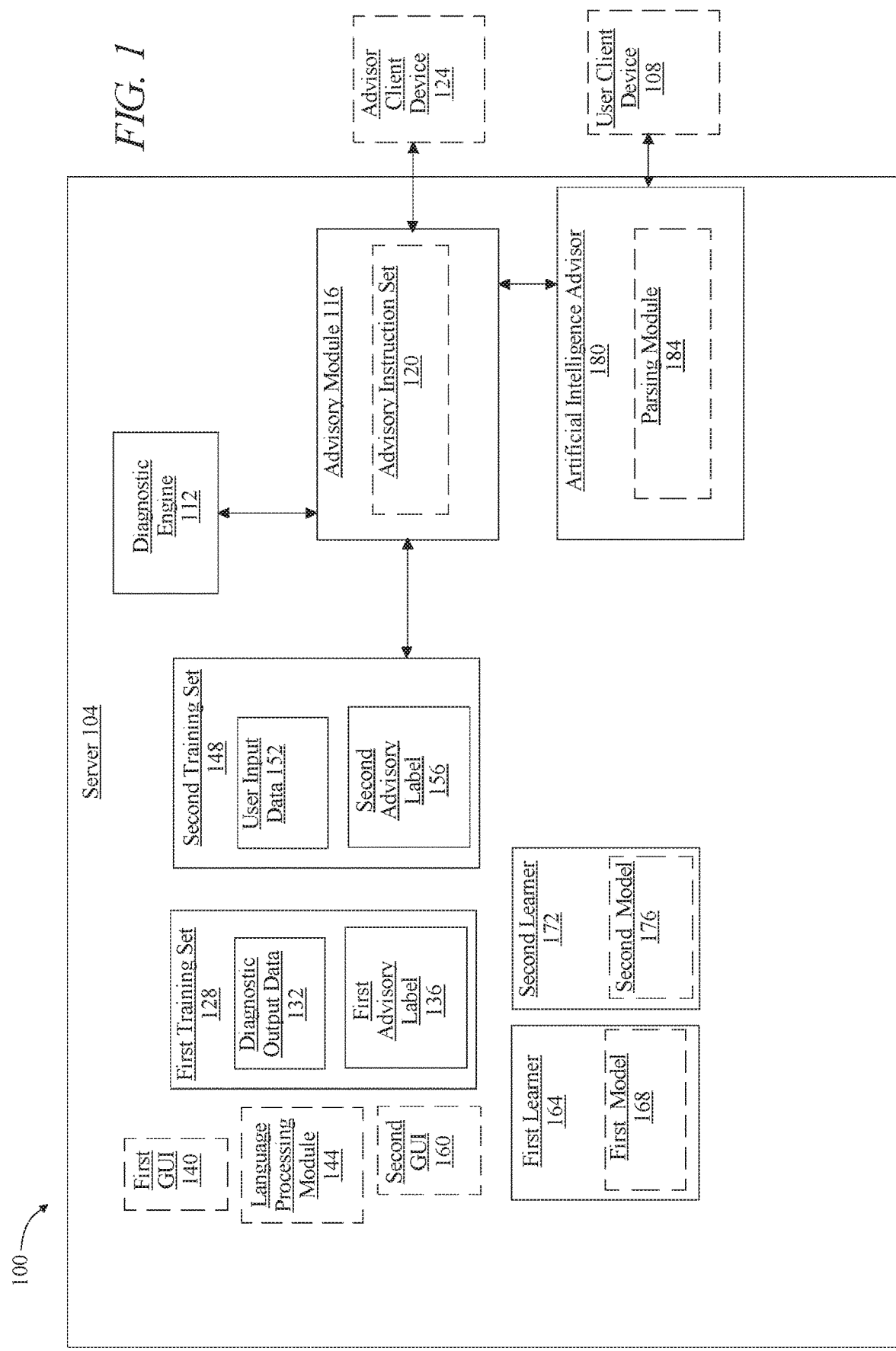
FIG. 1 is a block diagram illustrating an exemplary embodiment of an artificial intelligence advisory system for textual analysis.

Turning now to FIG. 1, an artificial intelligence advisory system 100 for textual analysis is illustrated. Artificial intelligence advisory system includes at least a server 104. At least a server 104 may include any computing device as described herein, including without limitation a microcontroller, microprocessor, digital signal processor (DSP) and/or system on a chip (SoC) as described herein. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server is configured to receive at least a user input datum from a user client device 108. User input datum, as used herein, may include any request, comment, question, remark, desire, aspiration, input, description, practice, and invitation, regarding spirituality, life coaching, and spiritual life coaching. Spirituality may include a desire to connect with the human spirit. Spirituality may include a desire to practice a particular religion such as a worship of a superhuman controlling power such as a personal God or gods. Religion may include a practice of faith, divinity, worship, creed, doctrine, theology and the like. Religion may include a practice of a particular religion such as Confucianism, Shinto, Taoism, Buddhism, Charvaka, Hinduism, Jainism, Meivazhi, Sikhism, Sarnaism, Christianity, Druze, Islam, Judaism, Mandaeism, Traditional African Folk religion, American Folk religion and the like. Spirituality may include certain practices including somatic practices such as deprivation and diminishment. Spirituality may include psychological practices including meditation. Spirituality may include social practices including obedience and communal ownership. Spirituality may include practices aimed at purifying ego-centeredness and divine reality. Life coaching may include addressing a user's personal concerns, projects, conditions, personal life, relationships, and profession life to discover obstacles a user may be facing and determine a course of action to best respond to a user's concerns. Life coaching may include behavior modifications aimed at building confidence, self-worth, self-esteem, loving relationships, an enjoyable workplace environment, living with purpose, managing anger, upsets, frustration, and stress, managing grief, loss, sadness, change, forming a confidant self-identity, and the like. Spiritual life coaching may include behavior modifications and coaching methodologies aid a user in developing and cultivating a spiritual practice. User input datum may include a request to cultivate a spiritual practice through exercise of practices such as prayer, meditation, breath work, energy work and the like. At least a user input datum may include a request for a spiritual coach including a spiritual informed advisor such as a pastor, rabbi, Buddhist monk, meditation teacher, Reiki teacher, and the like. Spiritual coach and/or life coach may include professionals focused on the conscious mind body connection. Spiritual professionals may include for example a teacher, mentor, or coach who may offer guidance, support, insight, and/or services for a user.

With continued reference to FIG. 1, at least a server receives at least a user input datum from a user client device 108. A user client device 108 may include, without limitation, a display in communication with at least a server 104; display may include any display as described herein. A user client device 108 may include an addition computing device, such as a mobile device, laptop, desktop computer, or the like; as a non-limiting example, the user client device 108 may be a computer and/or workstation operated by a medical professional. Output may be displayed on at least a user client device 108 using an output graphical user interface, as described in more detail below.

With continued reference to FIG. 1, system 100 may include a diagnostic engine 112 operating on at least a server 104, wherein the diagnostic engine 112 may be configured to receive at least a biological extraction from a user and generate a diagnostic output, the diagnostic output may include at least a prognostic label and at least an ameliorative process label. At least a server 104, diagnostic engine 112, and/or one or more modules operating thereon may be designed and/or configured to perform any method, method step, or sequence of method steps in any embodiment described in this disclosure, in any order and with any degree of repetition. For instance, at least a server 104 and/or diagnostic engine 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 and/or diagnostic engine 112 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing. Diagnostic engine 112 may be configured to record at least a biological extraction from a user and generate a diagnostic output based on the at least a biological extraction. Diagnostic engine 112 is described in more detail below in reference to FIG. 2.

With continued reference to FIG. 1, system 100 includes an advisory module 116 operating on at least a server 104. At least an advisory module 116 may include any suitable hardware or software module. At least an advisory module 116 is designed and configured to receive at least an advisory input and generate at least an advisory instruction set 120 as a function of the at least a user input datum and the at least an advisory input. At least an advisory input as used herein, includes any information provided by an informed advisor via advisor client device 124 as described in more detail below. At least an advisory input may include user data including user habits, preferences, current spiritual practices, religious affiliations, constitutional restrictions and the like. At least an advisory input may include spiritual, religious, and/or life coach information. Advisory input may include diagnostic information such as a user's previous diagnoses of cancer or user's diagnosis of heart disease. At least an advisory input may include an advisory recommendation for a user to engage in a specific spiritual practice or to read a particular religious passage. An informed advisor may include any person in addition to the user who has access to information useable to aid user in interaction with system 100 and to aid user with at least at least a user datum. Informed advisors may interact with one another and may aid user together in interaction with artificial intelligence advisory support system. Informed advisors may provide output to user client device 108 and/or advisor client device 124. Informed advisors may receive inputs from user client device 108 and/or advisor client device 124. Inputs and/or outputs may be exchanged using messaging services and/or protocols, including without limitation any instant messaging protocols. Text messages may be provided in textual form and/or as audio files using, without limitation, speech-to-text and/or text-to-speech algorithms. Informed advisors may provide inputs and/or outputs to one another and/or to user. Informed advisors may work together to create customized treatment plans around different aspects of a user's life.

With continued reference to FIG. 1, a spiritual informed advisor such as a meditation teacher may provide user a series of meditative exercises to practice as a calming practice to reduce stress and lower blood pressure. Inputs and/or outputs may be exchanged among informed advisors to modify recommendations and/or treatments as user initiates and implements each recommendation. Spiritual professional informed advisors may include individuals associated with certain spiritual religions such as for example a pastor at a church, a rabbi at a synagogue, a member of the Buddhist community, an imam, or the like. Spiritual professional informed advisors may be non-denominational including for example a teacher, mentor, and/or coach who may not be associated with any particular or specific religious denomination. Spiritual professional informed advisors may participate in cultivating spirituality through the exercise of certain practices. This may include but is not limited to meditation, prayer, breath work, energy work, somatic techniques, mind heart connections, chanting, asceticism Tai-chi, and Qigong. Meditation may include exercises designed to control a user's attention. Meditation may be practiced by varying techniques by varying spiritual traditions such as Buddhism, Vedanta, Yoga, Tantra, Jainism and the like. Prayer may include exercises directed towards a higher power and may include directing one's mind towards the Divine. Prayer may be scripted or spontaneous, spoken out loud, spoken silently in the mind, or without words. Breath and energy work may include techniques that incorporate breath work practiced in connection to one's body. This may be accompanied with visualization techniques or chanting of certain mantras or words. Breath and energy work may include certain practices such as pranayama from yoga and/or qigong from Daoism. Somatic techniques may utilize certain body postures and movements which may stimulate energy flow. Somatic techniques may include yoga asanas and/or Buddhist mudras for example. Certain mind heart connections and qualities may be developed such as principals that encompass certain core values and beliefs such as tranquility, humility, compassion, trust, devotion, discipline, courage, mindfulness, truthfulness, morality and the like. Chanting may be practiced as a means of devotion and calming of one's mind. Periods of asceticism and self-discipline may be emphasized such as periods of simplicity, vows of silence, retreats, digital detoxes and the like. Coordinated body posture and movement such as Tai-chi and Qigong may be practiced.

With continued reference to FIG. 1, advisory module 116 generates at least an advisory instruction set 120 as a function of the at least a user input datum and the at least an advisory input. Advisory instruction set 120 as used herein, is a data structure containing instructions to be provided to the user to provide the user with guidance in regard to spirituality, life coaching, and/or spiritual life coaching. Advisory instruction set 120 may include but is not limited to a program, strategy, summary, recommendation, or any other type of interactive platform that may be configured to comprise information associated with the user, an applicable verified external source, and one or more outputs derived from analysis performed on at least a user input datum. Advisory instruction set 120 may describe to the user a future spiritual and/or life state to aspire to. In an embodiment, advisory module 116 may be configured to update at least an advisory instruction set 120 as a function of at least a user input. For example, a user input that describes a user's progress with a particular meditation sequence may be utilized to generate an updated advisory instruction set 120 that includes an additional meditation sequence. In yet another non-limiting example, a user input that describes a user's inability to practice a particular meditation sequence because it is too time consuming may be utilized to generate an updated advisory instruction set 120 that includes a meditation sequence that is scaled back and not as time consuming. In yet another non-limiting example, a user input that describes a user's attendance at church may be verified by checking geolocation of a user to determine if user attended church. In such an instance, a user who attended church may receive at least a textual output containing congratulatory words for user about user's church attendance whereas a user who did not attend church may receive at least a textual output containing words of encouragement and support to motivate user to attend church.

With continued reference to FIG. 1, advisory module 116 receives at least an advisory input from an advisor client device 124. At least an advisor client device 124 may be operated by an informed advisor, defined for the purposes of this disclosure as any person besides the user who has access to information useable to aid user in interaction with artificial intelligence advisory system. An informed advisor may include, without limitation, a medical professional such as a doctor, nurse, nurse practitioner, functional medicine practitioner, any professional with a career in medicine, nutrition, genetics, fitness, life sciences, insurance, and/or any other applicable industry that may contribute information and data to system 100 regarding medical needs. An informed advisor may include a spiritual or philosophical advisor, such as a religious leader, pastor, imam, rabbi, or the like. An informed advisor may include a physical fitness advisor, such as without limitation a personal trainer, instructor in yoga or martial arts, sports coach, or the like. At least an advisor client device 124 may include any device suitable use as user client device 108 as described above.

With continued reference to FIG. 1, at least a server 104, diagnostic engine 112, and/or advisory module 116 may be configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, at least a server 104 may be configured to receive a first training set 128 including a plurality of first data entries, each first data entry of the first training set 128 including at least an element of diagnostic data and at least a correlated first advisory label. At least an element of diagnostic data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors; absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DI-IIIA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more measures of psychological function or state, such as without limitation clinical interviews, assessments of intellectual functioning and/or intelligence quotient (IQ) tests, personality assessments, and/or behavioral assessments. Physiological state data may include one or more psychological self-assessments, which may include any self-administered and/or automatedly computer-administered assessments, whether administered within system 100 and/or via a third-party service or platform.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 144 as described in this disclosure.

With continued reference to FIG. 1, physiological state data may include one or more evaluations of sensory ability, including measures of audition, vision, olfaction, gustation, vestibular function and pain. Physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein, is data describing all proteins produced and/or modified by an organism, colony of organisms, or system of organisms, and/or a subset thereof. Physiological state data may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on advisory labels and/or ameliorative processes as described in further detail below. Physiological state data may include any physiological state data, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Examples of physiological state data described in this disclosure are presented for illustrative purposes only and are not meant to be exhaustive. Persons skilled in the art, upon reviewing the entirety of this disclosure, will be aware of various additional examples of physiological state data that may be used consistently with descriptions of systems and methods as provided in this disclosure.

With continued reference to FIG. 1, each element of first training set 128 includes at least a first advisory label 136. A first advisory label 136, as described herein, is an element of data identifying and/or describing any spirituality, life coaching, and/or spiritual life coaching program, strategy, summary, recommendation, or any other type of interactive platform. A first advisory label 136 may be associated with one or more diagnostic outputs. For example, an advisory label such as a meditation sequence may be associated with one or more diagnostic outputs including cancer, hypertension, menopause, irritable bowel syndrome, smoking cessation, attention deficit hyperactivity disorder (ADHD), and anxiety. In yet another non-limiting example, a first advisory label 136 such as Reiki may be associated with one or more diagnostic outputs including cancer, heart disease, anxiety, depression, chronic pain, infertility, neurodegenerative disorders, autism, Chron's disease, and chronic fatigue syndrome. In yet another non-limiting example, a first advisory label 136 such as yoga may be associated with one or more diagnostic outputs including chronic stress, anxiety, depression, heart disease, back pain, depression, anger, diabetes, and thyroid disease. In yet another non-limiting example, a first advisory label 136 such as prayer may be associated with one or more diagnostic outputs including anxiety, depression, schizophrenia, obsessive-compulsive disorder, tardive dyskinesia, ischemia heart disease, cardiac failure, Parkinson's disease, and cancer.

With continued reference to FIG. 1, first advisory label 136 may be stored in any suitable data and/or data type. For instance, and without limitation, at least an advisory label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least an advisory label may take; persons skilled in the art, upon reviewing the entirety of this disclosure, will be aware of various forms which may be suitable for use as at least an advisory label consistently with this disclosure.

With continued reference to FIG. 1, in each first data element of first training set 128 at least a first advisory label 136 of the data element is correlated with at least an element of diagnostic data including physiological data. In an embodiment, an element of physiological data is correlated with an advisory label where the element of physiological data is located in the same data element and/or portion of data element as the advisory label; for example, and without limitation, an element of physiological data is correlated with an advisory element where both element of physiological data and advisory element are contained within the same first data element of the first training set 128. As a further example, an element of physiological data is correlated with an advisory element where both share a category label as described in further detail below, where each is within a certain distance of the other within an ordered collection of data in data element, or the like. Still further, an element of physiological data may be correlated with an advisory label where the element of physiological data and the advisory label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and advisory labels that may exist in first training set 128 and/or first data element consistently with this disclosure.

With continued reference to FIG. 1, at least a server 104 may be designed and configured to associate at least an element of physiological state data with at least a category from a list of significant categories of physiological state data. Significant categories of physiological state data may include labels and/or descriptors describing types of physiological state data that are identified as being of high relevance in identifying advisory labels. As a non-limiting example, one or more categories may identify significant categories of physiological state data based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or associated spiritual treatments within a certain field. As a non-limiting example, and without limitation, physiological data describing disorders of the mind associated with overactivity of the mind including anxiety, obsessive compulsive disorder, depression, bipolar disorder, obsessive compulsive disorder, panic attacks, anger, and post-traumatic stress disorder may be useful in selecting spiritual practices that are designed to calm the mind such as prayer, tai chi, qi gong, and yoga. As an additional example, diagnostic outputs and/or physiological data associated with high risks of mortality such as heart disease, stroke, diabetes, intentional self-harm such as suicide, Alzheimer's disease, and chronic lower respiratory diseases may be useful in selecting spiritual practices that are focused in seeking out a higher power and developing a religious practice such as Christianity, Buddhism, and Judaism. In a further non-limiting example, chronic health conditions including diagnostic outputs such as diabetes, hypertension, arthritis, rheumatoid arthritis, multiple sclerosis, and the like may be useful in selecting spiritual practices that are focused on meditative practices including mindfulness meditation, breath awareness meditation, transcendental meditation, and kundalini yoga. Persons skilled in the art, upon reviewing the entirety of this disclosure, will be aware of various additional categories of physiological data that may be used consistently with this disclosure.

Still referring to FIG. 1, at least a server 104 may receive the list of significant categories according to any suitable process; for instance, and without limitation, at least a server 104 may receive the list of significant categories from at least an expert. In an embodiment, at least a server 104 and/or a user device connected to at least a server 104 may provide a first graphical user interface 140, which may include without limitation a form or other graphical element having data entry fields, wherein one or more experts, including without limitation clinical and/or scientific experts, may enter information describing one or more categories of physiological data that the experts consider to be significant or useful for detection of conditions; fields in first graphical user interface 140 may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. First graphical user interface 140 or the like may include fields corresponding to advisory labels, where experts may enter data describing advisory labels and/or categories of advisory labels the experts consider related to entered categories of physiological data; for instance, such fields may include drop-down lists or other pre-populated data entry fields listing currently recorded advisory labels, and which may be comprehensive, permitting each expert to select an advisory label and/or a plurality of advisory labels the expert believes to be predicted and/or associated with each category of physiological data selected by the expert. Fields for entry of advisory labels and/or categories of advisory labels may include free-form data entry fields such as text entry fields; as described above, examiners may enter data not presented in pre-populated data fields in the free-form data entry fields. Alternatively or additionally, fields for entry of advisory labels may enable an expert to select and/or enter information describing or linked to a category of advisory label that the expert considers significant, where significance may indicate likely impact on longevity, mortality, quality of life, or the like as described in further detail below. First graphical user interface 140 may provide an expert with a field in which to indicate a reference to a document describing significant categories of physiological data, relationships of such categories to advisory labels, and/or significant categories of advisory labels. Any data described above may alternatively or additionally be received from experts similarly organized in paper form, which may be captured and entered into data in a similar way, or in a textual form such as a portable document file (PDF) with examiner entries, or the like.

With continued reference to FIG. 1, data information describing significant categories of physiological data, relationships of such categories to advisory labels, and/or significant categories of advisory labels may alternatively or additionally be extracted from one or more documents using a language processing module 144. Language processing module 144 may include any hardware and/or software module. Language processing module 144 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (G-D&T) symbols, chemical symbols and formulas, spaces, whitespace, and other symbols, including any symbols usable as textual data as described above Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 144 may compare extracted words to categories of physiological data recorded by at least a server 104, one or more advisory labels recorded by at least a server 104, and/or one or more categories of advisory labels recorded by at least a server 104; such data for comparison may be entered on at least a server 104 as described above using expert data inputs or the like. In an embodiment, one or more categories may be enumerated, to find total count of mentions in such documents. Alternatively or additionally, language processing module 144 may operate to produce a language processing model. Language processing model may include a program automatically generated by at least a server 104 and/or language processing module 144 to produce associations between one or more words extracted from at least a document and detect associations, including without limitation mathematical associations, between such words, and/or associations of extracted words with categories of physiological data, relationships of such categories to advisory labels, and/or categories of advisory labels. Associations between language elements, where language elements include for purposes herein extracted words, categories of physiological data, relationships of such categories to advisory labels, and/or categories of advisory labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to advisory labels, and/or a given category of advisory labels. As a further example, statistical correlations and/or mathematical associations may include probabilistic formulas or relationships indicating a positive and/or negative association between at least an extracted word and/or a given category of physiological data, a given relationship of such categories to advisory labels, and/or a given category of advisory labels; positive or negative indication may include an indication that a given document is or is not indicating a category of physiological data, relationship of such category to advisory labels, and/or category of advisory labels is or is not significant. For instance, and without limitation, a negative indication may be determined from a phrase such as "meditation was not found to reduce stress in diabetic patients," whereas a positive indication may be determined from a phrase such as "meditation was found to reduce stress in cancer patients," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory by at least a server 104, or the like.

Still referring to FIG. 1, language processing module 144 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model HMMs as used herein, are statistical models with inference algorithms that that may be applied to the models. In such models, a hidden state to be estimated may include an association between an extracted word category of physiological data, a given relationship of such categories to advisory labels, and/or a given category of advisory labels. There may be a finite number of category of physiological data, a given relationship of such categories to advisory labels, and/or a given category of advisory labels to which an extracted word may pertain; an HMM inference algorithm, such as the forward-backward algorithm or the Viterbi algorithm, may be used to estimate the most likely discrete state given a word or sequence of words. Language processing module 144 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 144 may use a corpus of documents to generate associations between language elements in a language processing module 144 and at least a server 104 may then use such associations to analyze words extracted from one or more documents and determine that the one or more documents indicate significance of a category of physiological data, a given relationship of such categories to advisory labels, and/or a given category of advisory labels. In an embodiment, at least a server 104 may perform this analysis using a selected set of significant documents, such as documents identified by one or more experts as representing good science, good clinical analysis, or the like; experts may identify or enter such documents via graphical user interface, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to advisory labels, and/or a given category of advisory labels is entered via graphical user interface, alternative submission means, and/or extracted from a document or body of documents as described above, an entry or entries may be aggregated to indicate an overall degree of significance. For instance, each category of physiological data, relationship of such categories to advisory labels, and/or category of advisory labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to advisory labels, and/or categories of advisory labels may be ranked according significance scores, for instance by ranking categories of physiological data, relationships of such categories to advisory labels, and/or categories of advisory labels higher according to higher significance scores and lower according to lower significance scores. Categories of physiological data, relationships of such categories to advisory labels, and/or categories of advisory labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to advisory labels, and/or category of advisory labels is significant with regard to that test, while a second category of physiological data, relationship of such category to advisory labels, and/or category of advisory labels is not significant; such indications may be used to perform a significance score for each category of physiological data, relationship of such category to advisory labels, and/or category of advisory labels is or is not significant per type of physiological sample, which then may be subjected to ranking, comparison to thresholds and/or elimination as described above.

Still referring to FIG. 1, at least a server 104 may detect further significant categories of physiological data, relationships of such categories to advisory labels, and/or categories of advisory labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, at least a server 104 may be configured, for instance as part of receiving the first training set 128, to associate at least correlated first advisory label 136 with at least a category from a list of significant categories of advisory labels. Significant categories of advisory labels may be acquired, determined, and/or ranked as described above. As a non-limiting example, advisory labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result at least a server 104 may modify list of significant categories to reflect this difference.

Still referring to FIG. 1, at least a server 104 is designed and configured to receive a second training set 148 including a plurality of second data entries. Each second data entry of the second training set 148 includes at least an element of user input data 152 correlated with the at least a second advisory label, where correlation may include any correlation suitable for correlation of at least a first advisory label 136 to at least an element of physiological data as described above. Each second data entry of the second training set 148 includes at least a second advisory label; at least a second advisory label 156 may include any label suitable for use as at least a first advisory label 136 as described above. As used herein, a user input label is an identifier, which may include any form of identifier suitable for use as an advisory label as described above, including any type of request pertaining to spirituality, life coaching, and/or spiritual life coaching. User inputs may include, without limitation, requests, comments, questions, remarks, desires, aspirations, inputs, descriptions, practices, and invitations regarding spirituality, life coaching, and spiritual life coaching. User inputs may include, without limitation, a desire to develop a spirituality practice or create a meditation practice. User inputs may include a desire to live a more spiritual based life. User inputs may include a desire to handle a life problem with a spiritual perspective. User inputs may include a desire to cultivate a prayer practice. Persons skilled in the art, upon reviewing the entirety of this disclosure, will be aware of various processes that may be used as user inputs consistently with this disclosure.

Continuing to refer to FIG. 1, in an embodiment at least a server 104 may be configured, for instance as part of receiving second training set, to associate the at least second advisory label 156 with at least a category from a list of significant categories of advisory labels. This may be performed as described above for use of lists of significant categories with regard to at least a first advisory label 136. Significance may be determined, and/or association with at least a category, may be performed for advisory labels in first training set 128 according to a first process as described above and for advisory labels in second training set 148 according to a second process as described above.

Still referring to FIG. 1, at least a server 104 may be configured, for instance as part of receiving second training set, to associate at least a correlated user input with at least a category from a list of significant categories of user inputs. In an embodiment, at least a server and/or a user device connected to at least a server may provide a second graphical user interface 160 which may include without limitation a form or other graphical element having data entry fields, wherein one or more experts, including without limitation clinical and/or scientific experts, may enter information describing one or more categories of advisory labels that the experts consider to be significant as described above; fields in graphical user interface may provide options describing previously identified categories, which may include a comprehensive or near-comprehensive list of types of advisory labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to user data labels, where experts may enter data describing user data labels and/or categories of user data labels the experts consider related to entered categories of advisory labels; for instance, such fields may include drop-down lists or other pre-populated data entry fields listing currently recorded user data labels, and which may be comprehensive, permitting each expert to select a user data label and/or a plurality of user data labels the expert believes to be predicted and/or associated with each category of advisory labels selected by the expert. Fields for entry of user data labels and/or categories of user data labels may include free-form data entry fields such as text entry fields; as described above, examiners may enter data not presented in pre-populated data fields in the free-form data entry fields. Alternatively or additionally, fields for entry of user data labels may enable an expert to select and/or enter information describing or linked to a category of user data label that the expert considers significant, where significance may indicate likely impact on longevity, mortality, quality of life, or the like as described in further detail below. Graphical user interface may provide an expert with a field in which to indicate a reference to a document describing significant categories of advisory labels, relationships of such categories to user data labels, and/or significant categories of user data labels. Such information may alternatively be entered according to any other suitable means for entry of expert data as described above. Data concerning significant categories of advisory labels, relationships of such categories to user data labels, and/or significant categories of user data labels may be entered using analysis of documents using language processing module 144 or the like as described above.

In an embodiment, and still referring to FIG. 1, at least a server 104 may extract at least a second data entry from one or more documents; extraction may be performed using any language processing method as described above. At least a server 104 may be configured, for instance as part of receiving second training set, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by an advisory label; for instance, the medical history document may list a diagnosis that a medical practitioner made concerning the patient, a finding that the patient is at risk for a given condition and/or evinces some precursor state for the condition, or the like. A medical history document may contain data describing and/or described by a user input label; for instance, the medical history document may list a therapy, recommendation, or other user input that a medical practitioner described or recommended to a patient. A medical history document may describe an outcome; for instance, medical history document may describe an improvement in a condition describing or described by an advisory label, and/or may describe that the condition did not improve. Advisory labels, user input labels, and/or efficacy of advisory labels may be extracted from and/or determined from one or more medical history documents using any processes for language processing as described above; for instance, language processing module 144 may perform such processes. As a non-limiting example, positive and/or negative indications regarding ameliorative processes identified in medical history documents may be determined in a manner described above for determination of positive and/or negative indications regarding categories of physiological data, relationships of such categories to advisory labels, and/or categories of advisory labels.

With continued reference to FIG. 1, at least a server 104 may be configured, for instance as part of receiving second training set, to receiving at least a second data entry of the plurality of second data entries from at least an expert. This may be performed, without limitation using second graphical user interface 160 as described above.

With continued reference to FIG. 1, system 100 may include a first label learner operating on at least a server 104, the first label learner designed and configured to generate at least an advisory instruction set 120 using machine-learning algorithm and the first training set 128. First label learner may include any hardware and/or software module. First label learner is designed and configured to generate outputs using machine-learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

With continued reference to FIG. 1, first label learner may be designed and configured to generate at least an advisory instruction set 120 by creating at least a first machine-learning model 168 relating diagnostic output data 132 to advisory labels using the first training set 128 and generating at least an advisory instruction set 120 using the first machine-learning model 168; at least a first machine-learning model 168 may include one or more models that determine a mathematical relationship between diagnostic output data 132 and advisory labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, machine-learning algorithms may generate at least an advisory instruction set 120 as a function of a classification of at least an advisory label. Classification as used herein includes pairing or grouping advisory labels as a function of a shared commonality. Classification may include for example, groupings, pairings, and/or trends between diagnostic data including for example physiological data and current advisory label, future advisory label, and the like. In an embodiment, machine-learning algorithms may examine relationships between a future propensity of a user to need a new and/or additional advisory label as a function of current advisory label and/or current diagnostic output and/or new diagnostic output. Machine-learning algorithms may include any and all algorithms as performed by any modules, described herein for first label learner. For example, machine-learning algorithms may relate current cancer diagnosis to subsequent additional diagnosis and new advisory label needed. Machine-learning algorithms may examine precursor condition and future propensity to develop a subsequent disorder. For example, machine-learning algorithms may examine a user diagnosed with chicken pox and user's future propensity to subsequently develop shingles. In yet another non-limiting example, machine-learning algorithms may examine infection with human papillomavirus (HPV) and subsequent cancer diagnosis. Machine-learning algorithms may examine a user's propensity to have recurring attacks of a disease or condition, for example a user with elevated uric acid levels and repeated attacks of gout. Machine-learning algorithms may examine user's genetic predisposition to develop a certain condition or disease. For example, machine-learning algorithms may examine presence of hereditary non-polyposis colorectal cancer (HNPCC) commonly known as lynch syndrome, and subsequent diagnosis of colorectal cancer. In yet another non-limiting example, machine-learning algorithms may examine presence of abnormal squamous cells and/or abnormal glandular cells in the cervix and subsequent development of cervical cancer. Machine-learning algorithms may examine progression of disease state, for example progression of human immunodeficiency virus (HIV) is marked by decline of CD4+T-Cells, with a count below 200 leading to a diagnosis of acquired immunodeficiency syndrome (AIDS). In yet another non-limiting example, progression of diabetes may be marked by increases of hemoglobin A1C levels with a level of 6.5% indicating a diagnosis of diabetes. Machine-learning algorithms may examine progression of disease by certain age groups. For example, progression of Multiple Sclerosis in users between the age of 20-30 as compared to progression of Multiple Sclerosis in users between the age of 70-80. Machine-learning algorithms may be examining progression of aging such as measurements of telomere length and/or oxidative stress levels and chance mortality risk. Machine-learning algorithms may examine development of co-morbid conditions when a disease or conditions is already present. For example, machine-learning algorithms may examine a user diagnosed with depression and subsequent diagnosis of a co-morbid condition such as migraines, generalized anxiety disorder, antisocial personality disorder, agoraphobia, obsessive-compulsive disorder, drug dependence alcohol dependence, and/or panic disorder. Machine-learning algorithms may examine a user's lifetime chance of developing a certain disease or condition, such as a user's lifetime risk of heart disease, Alzheimer's disease, diabetes and the like. Machine-learning algorithms may be grouped and implemented according to any of the methodologies as described herein.

Continuing to refer to FIG. 1, machine-learning algorithm used to generate first machine-learning model 168 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, first label learner may generate at least an advisory instruction set 120 using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 128; the trained network may then be used to apply detected relationships between elements of diagnostic data including for example physiological state data and advisory labels.

With continued reference to FIG. 1, machine-learning algorithms may include unsupervised processes; unsupervised processes may, as a non-limiting example, be executed by an unsupervised learning module executing on at least a server 104 and/or on another computing device in communication with at least a server 104, which may include any hardware or software module as described herein. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, first label learner and/or at least a server 104 may perform an unsupervised machine learning process on first training set 128, which may cluster data of first training set 128 according to detected relationships between elements of the first training set 128, including without limitation correlations of elements of physiological state data to each other and correlations of advisory labels to each other; such relations may then be combined with supervised machine learning results to add new criteria for advisory label learner to apply in relating physiological state data to advisory labels. As a non-limiting, illustrative example, an unsupervised process may determine that a first element of physiological data acquired in a blood test correlates closely with a second element of physiological data, where the first element has been linked via supervised learning processes to a given advisory label, but the second has not; for instance, the second element may not have been defined as an input for the supervised learning process, or may pertain to a domain outside of a domain limitation for the supervised learning process. Continuing the example a close correlation between first element of physiological state data and second element of physiological state data may indicate that the second element is also a good predictor for the advisory label; second element may be included in a new supervised process to derive a relationship or may be used as a synonym or proxy for the first physiological element by first label learner Still referring to FIG. 1, at least a server 104 and/or first label learner may detect further significant categories of physiological data, relationships of such categories to advisory labels, and/or categories of advisory labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, first label learner and/or at least a server 104 may continuously or iteratively perform unsupervised machine-learning processes to detect relationships between different elements of the added and/or overall data; in an embodiment, this may enable system 100 to use detected relationships to discover new correlations between known biomarkers, advisory labels, and/or user input labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular advisory labels and/or suitable user input labels. Use of unsupervised learning may greatly enhance the accuracy and detail with which system may detect advisory labels and/or user input labels.

With continued reference to FIG. 1, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of advisory label, and/or a group of people having a shared value and/or category of user input label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 1 first label learner may alternatively or additionally be designed and configured to generate at least an advisory output by executing a lazy learning process as a function of the first training set 128 and at least a biological extraction; lazy learning processes may be performed by a lazy learning module executing on at least a server 104 and/or on another computing device in communication with at least a server, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at an advisory label associated with biological extraction, using first training set 128. As a non-limiting example, an initial heuristic may include a ranking of advisory labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and advisory labels, for instance as calculated as described above. Heuristic may include selecting some number of highest-ranking associations and/or advisory labels. First label learner may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate at least an advisory instruction set 120 as described in this disclosure, including without limitation lazy learning applications of machine-learning algorithms as described in further detail below.

Continuing to refer to FIG. 1, first label learner may generate a plurality of advisory labels having different implications for a particular person. For instance, where the at least a physiological sample includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, first label learner and/or at least a server 104 may perform additional processes to resolve ambiguity. Processes may include presenting multiple possible results to a medical practitioner, informing the medical practitioner that one or more follow-up tests and/or physiological samples are needed to further determine a more definite advisory label. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, first label learner and/or at least a server 104 may operate a further algorithm to determine which of the multiple outputs is most likely to be correct; algorithm may include use of an additional supervised and/or unsupervised model. Alternatively or additionally, first label learner may perform one or more lazy learning processes using a more comprehensive set of user data to identify a more probably correct result of the multiple results. Results may be presented and/or retained with rankings, for instance to advise a medical professional of the relative probabilities of various advisory labels being correct; alternatively or additionally, advisory labels associated with a probability of correctness below a given threshold and/or advisory labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of advisory labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of advisory labels on a list of multiple advisory labels, and/or to eliminate some labels from such a list.

Still referring to FIG. 1, at least a server 104 includes a second label learner operating on at least a server, the second label learner designed and configured to generate at least an advisory instruction set 120 using a second machine learning algorithm and the second training set. Second label learner may include any hardware or software module suitable for use as first label learner as described above. Second label learner is a machine-learning module as described above; second label learner may perform any machine-learning process or combination of processes suitable for use by first label learner as described above. For instance, and without limitation, second label learner may be configured to create a second machine-learning model 176 relating at least an element of user input data 152 and at least a correlated second advisory label 156 to generate at least an advisory instruction set 120 using the second machine learning model; second machine-learning model 176 may be generated according to any process, process steps, or combination of processes and/or process steps suitable for creation of first machine learning model. In an embodiment, second label learner may use data from first training set 128 as well as data from second training set 148; for instance, second label learner may use lazy learning and/or model generation to determine relationships between elements of physiological data, in combination with or instead of advisory labels, and user input labels. Where second label learner determines relationships between elements of physiological data and user input labels directly, this may determine relationships between advisory labels and user input labels as well owing to the existence of relationships determined by first label learner.

With continued reference to FIG. 1, at least a server, first learner 164, and/or second learner 172 may perform machine-learning algorithms using a loss function analysis utilizing linear regression based on past interactions between a user and system 100 and advisory instruction set 120 to generate advisory instruction set 120. In an embodiment, at least a server, first learner 164, and/or second learner 172 may compare one or more advisory instruction set 120 options to a mathematical expression representing an optimal combination of user-specific variables. Mathematical expression may include a linear combination of variables, weighted by coefficients representing relative importance of each variables in generating an optimal advisory instruction set 120. For instance, a user-specific variable such as religious denomination preference may be multiplied by a first coefficient representing the importance of religious denomination, a second user-specific variable such as total time to devote to a spiritual practice each week may be multiplied by a second coefficient representing the importance of time, a degree of variance from an advisory instruction set 120 may be represented as another parameter, which may be multiplied by another coefficient representing the importance of that parameter, a degree of variance from another user-specific variable may be multiplied by an additional coefficient representing an importance of that parameter, and/or a parameter representing a degree of variance from one or more other user-specific variables may be provided a coefficient representing the importance of such a variance; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, at least a server, first learner 164, and/or second learner 172 may calculate variables of each of a plurality of user-specific variables, calculate an output of mathematical expression using the variables, and select an advisory instruction set 120 that produces an output having the lowest size, according to a given definition of "size," of the set of outputs representing each of the plurality of advisory instruction set 120; size may, for instance, included absolute value, numerical size, or the like. Selection of different loss functions may result in identification of different advisory instruction set 120 as generating minimal outputs; for instance, where religious denomination is associated in a first loss function with a large coefficient or weight, a user-specific variable having a short transit time may minimize the first loss function, whereas a second loss function wherein religious denomination has a smaller coefficient but degree of variance from religious denomination has a larger coefficient may produce a minimal output for a different advisory instruction having a longer transit time but more closely hewing to a religious denomination.

Alternatively or additionally, and still referring to FIG. 1, each user-specific variable may be represented by a mathematical expression having the same form as mathematical expression; at least a server, first learner 164, and/or second learner 172 may compare the former to the latter using an error function representing average difference between the two mathematical expressions. Error function may, as a non-limiting example, be calculated using the average difference between coefficients corresponding to each variable. A user-specific variable having a mathematical expression minimizing the error function may be selected, as representing an optimal expression of relative importance of variables to a system or user. In an embodiment, error function and loss function calculations may be combined; for instance, a user-specific variable resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to other user-specific variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable to the user. Sliders or other inputs may be initialized prior to user entry as equal, or may be set to default values based on results of any machine-learning processes or combinations thereof as described in further detail below.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary provision options.

At least a server, first learner 164, and/or second learner 172 may generate a loss function of user specific variables and minimize the loss function. At least a server, first learner 164, and/or second learner 172 may generate advisory instruction set 120 utilizing loss function analysis. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. At least a server, first learner 164, and/or second learner 172 may utilize variables to model relationships between past interactions between a user and system 100 and advisory instruction set 120. In an embodiment loss function analysis may utilize variables that may impact user interactions and/or advisory instruction set 120. Variables are described in more detail below in reference to FIG. 16. Loss function analysis may be user specific so as to create algorithms and outputs that are customize to variables for an individual user. User behaviors and user past responses may be utilized as training data to generate outputs. Variables contained within loss function analysis may be weighted and given different numerical scores. Variables may be stored and utilized to predict subsequent outputs. Outputs may seek to predict user behavior and past user interactions with system 100 and advisory instruction set 120.

With continued reference to FIG. 1, system 100 includes an artificial intelligence advisor 180 configured to perform a user textual conversation with the user client device 108. Artificial intelligence advisor 180 is configured to generate at least a textual output as a function of the at least an advisory instruction set 120 and receive at least a user input as a function of the at least a textual output. Artificial intelligence advisor 180 may receive inputs from user client device 108 and/or advisor client device 124. Inputs and/or outputs may be exchanged using messaging services and protocols, including without limitation any instant messaging protocols. Persons skilled in the art, upon reviewing the entirety of this disclosure, will be aware of a multiplicity of communication protocols that may be employed to exchange text messages as described herein. Text messages may be provided in textual form and/or as audio files using, without limitation, speech-to-text and/or text-to-speech algorithms.

With continued reference to FIG. 1, artificial intelligence advisor 180 may include a parsing module 184 configured to generate at least a query using at least a user input datum and generate at least a textual output as a function of the at least a query. At least a query, as used in this disclosure, is at least a datum used to retrieve text that will be incorporated in at least a textual output, where retrieval may be effected by inputting the at least a query into a data structure, database, and/or model, and receiving a corresponding output as a result, for example as set forth in further detail below. In an embodiment, parsing module 184 may include language processing module 144 configured to map the at least a user input datum to the at least a query. Parsing module 184 includes any of the hardware and software components as described in more detail below in reference to FIGS. 17-21.

Figure 2:
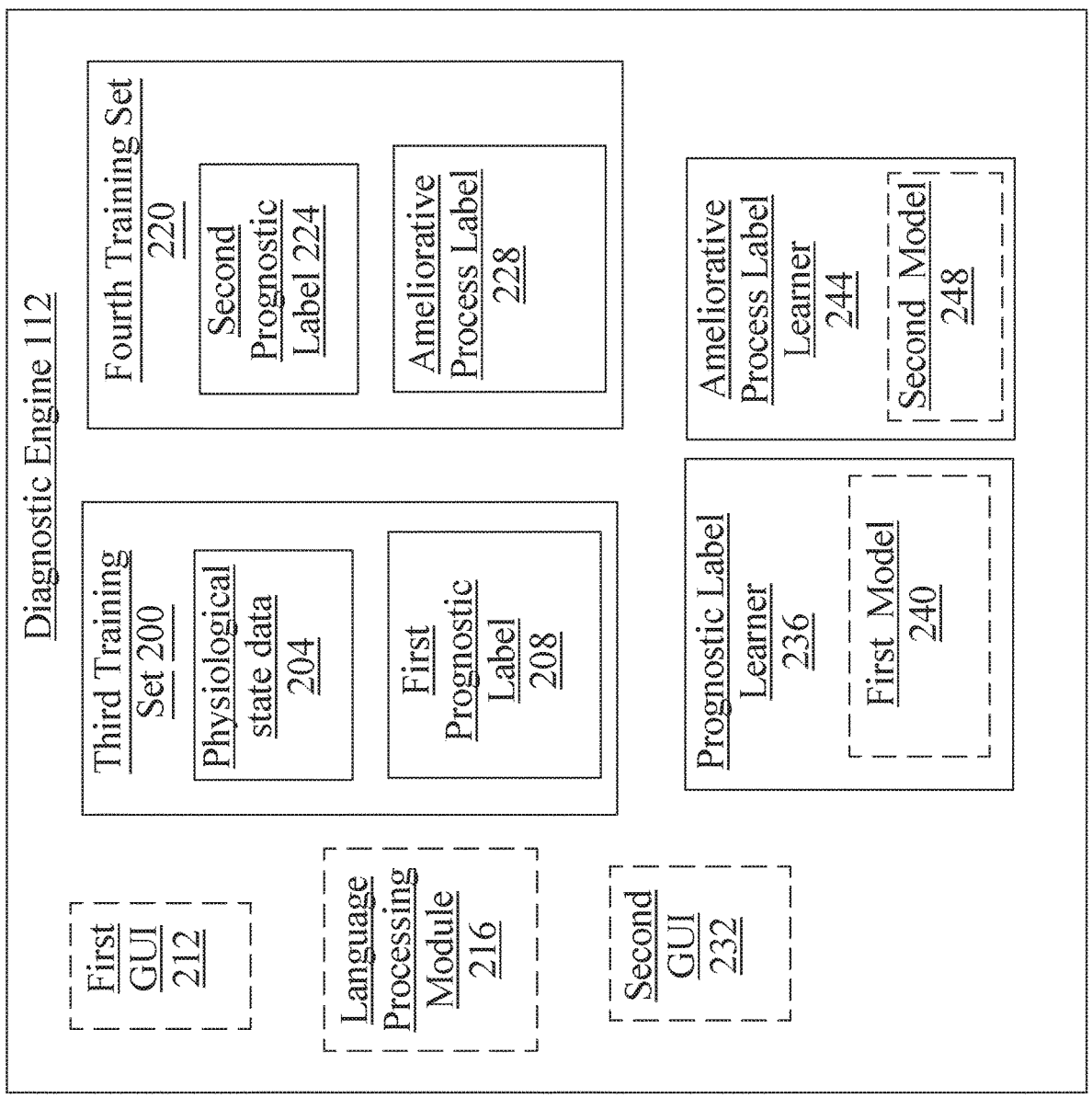
FIG. 2 is a block diagram illustrating an exemplary embodiment of a diagnostic engine.

Referring now to FIG. 2, an exemplary embodiment of diagnostic engine 112 is illustrated. In an embodiment, diagnostic engine 112 may be configured to record at least a biological extraction from a user and generate a diagnostic output based on the at least a biological extraction. At least a biological extraction may include any of the biological extractions as described above in reference to FIG. 1. In an embodiment, diagnostic engine may generate a diagnostic output based on the at least a biological extraction using training data and a machine-learning model. Training data may include any of the training data as described above in reference to FIG. 1. In an embodiment, diagnostic engine 112 may receive a third training set 200 including a plurality of first data entries, each first data entry of the third training set 200 including at least an element of physiological state data 204 and at least a correlated first prognostic label 208. Physiological state data 204 may include any of the physiological state data as described above in reference to FIG. 1.

Continuing to refer to FIG. 2, each element of third training set 200 includes at least a first prognostic label 208. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognostic label may be associated with a physical and/or somatic condition, a mental condition such as a mental illness, neurosis, or the like, or any other condition affecting human health that may be associated with one or more elements of physiological state data 204 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrine disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 2, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 2, in each first data element of third training set 200, at least a first prognostic label 208 of the data element is correlated with at least an element of physiological state data 204 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the third training set 200. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in third training set 200 and/or first data element consistently with this disclosure.

In an embodiment, and still referring to FIG. 2, diagnostic engine 112 may be designed and configured to associate at least an element of physiological state data 204 with at least a category from a list of significant categories of physiological state data 204. Significant categories of physiological state data 204 may include labels and/or descriptors describing types of physiological state data 204 that are identified as being of high relevance in identifying prognostic labels. As a non-limiting example, one or more categories may identify significant categories of physiological state data 204 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 2, diagnostic engine 112 may receive the list of significant categories according to any suitable process; for instance, and without limitation, diagnostic engine 112 may receive the list of significant categories from at least an expert. In an embodiment, diagnostic engine 112 and/or a user device connected to diagnostic engine 112 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like With continued reference to FIG. 2, data information describing significant categories of physiological data, relationships of such categories to prognostic labels, and/or significant categories of prognostic labels may alternatively or additionally be extracted from one or more documents using a language processing module 216. Language processing module 216 may include any hardware and/or software module. Language processing module 216 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 2, language processing module 216 may compare extracted words to categories of physiological data recorded at diagnostic engine 112, one or more prognostic labels recorded at diagnostic engine 112, and/or one or more categories of prognostic labels recorded at diagnostic engine 112; such data for comparison may be entered on diagnostic engine 112 as described above using expert data inputs or the like. In an embodiment, one or more categories may be enumerated, to find total count of mentions in such documents. Alternatively or additionally, language processing module 216 may operate to produce a language processing model. Language processing model may include a program automatically generated by diagnostic engine 112 and/or language processing module 216 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at diagnostic engine 112, or the like.

Still referring to FIG. 2, language processing module 216 and/or diagnostic engine 112 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model HMMs has used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HIM inference algorithm, such as the forward-backward algorithm or the Viterbi algorithm, may be used to estimate the most likely discrete state given a word or sequence of words. Language processing module 216 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 2, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 2, language processing module 216 may use a corpus of documents to generate associations between language elements in a language processing module 216, and diagnostic engine 112 may then use such associations to analyze words extracted from one or more documents and determine that the one or more documents indicate significance of a category of physiological data, a given relationship of such categories to prognostic labels, and/or a given category of prognostic labels. In an embodiment, diagnostic engine 112 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into diagnostic engine 112. Documents may be entered into diagnostic engine 112 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine 112 may automatically obtain the document using such an identifier, for instance by submitting a request to a database or compendium of documents such as JSTOR as provided by Ithaka Harbors, Inc. of New York.

Continuing to refer to FIG. 2, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of biological extraction, which then may be subjected to ranking, comparison to thresholds and/or elimination as described above.

Still referring to FIG. 2, diagnostic engine 112 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 2, in an embodiment, diagnostic engine 112 may be configured, for instance as part of receiving the third training set 200, to associate at least correlated first prognostic label 208 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result diagnostic engine 112 may modify list of significant categories to reflect this difference.

Still referring to FIG. 2, diagnostic engine 112 is designed and configured to receive a fourth training set 220 including a plurality of second data entries. Each second data entry of the fourth training set 220 includes at least a second prognostic label 224; at least a second prognostic label 224 may include any label suitable for use as at least a first prognostic label 208 as described above. Each second data entry of the fourth training set 220 includes at least an ameliorative process label 228 correlated with the at least a second prognostic label 224, where correlation may include any correlation suitable for correlation of at least a first prognostic label 208 to at least an element of physiological data as described above. As used herein, an ameliorative process label 228 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

Continuing to refer to FIG. 2, in an embodiment diagnostic engine 112 may be configured, for instance as part of receiving fourth training set 220, to associate the at least second prognostic label 224 with at least a category from a list of significant categories of prognostic labels. This may be performed as described above for use of lists of significant categories with regard to at least a first prognostic label 208. Significance may be determined, and/or association with at least a category, may be performed for prognostic labels in third training set 200 according to a first process as described above and for prognostic labels in fourth training set 220 according to a second process as described above.

Still referring to FIG. 2, diagnostic engine 112 may be configured, for instance as part of receiving fourth training set 220, to associate at least a correlated ameliorative process label 228 with at least a category from a list of significant categories of ameliorative process labels 228. In an embodiment, diagnostic engine 112 and/or a user device connected to diagnostic engine 112 may provide a second graphical user interface 232 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 216 or the like as described above.

In an embodiment, and still referring to FIG. 2, diagnostic engine 112 may extract at least a second data entry from one or more documents; extraction may be performed using any language processing method as described above. Diagnostic engine 112 may be configured, for instance as part of receiving fourth training set 220, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label 228; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 228, and/or efficacy of ameliorative process labels 228 may be extracted from and/or determined from one or more medical history documents using any processes for language processing as described above; for instance, language processing module 216 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 2, diagnostic engine 112 may be configured, for instance as part of receiving fourth training set 220, to receiving at least a second data entry of the plurality of second data entries from at least an expert. This may be performed, without limitation using second graphical user interface as described above.

Referring again to FIG. 2, diagnostic engine 112 may be configured to record at least a biological extraction. At least a biological extraction may include a physically extracted sample, which as used herein includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of diagnostic engine 112 or may be a separate device in communication with diagnostic engine 112.

Still referring to FIG. 2, at least a biological extraction may include any data suitable for use as physiological state data as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

Alternatively or additionally, and with continued reference to FIG. 2, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 2, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a biological extraction consistent with this disclosure. At least a biological extraction may be added to biological extraction database 300.

With continued reference to FIG. 2, diagnostic engine 112 may include a prognostic label learner 236 operating on the diagnostic engine 112, the prognostic label learner 236 designed and configured to generate the at least a prognostic output as a function of the third training set 200 and the at least a biological extraction. Prognostic label learner 236 may include any hardware and/or software module. Prognostic label learner 236 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 2, prognostic label learner 236 may be designed and configured to generate at least a prognostic output by creating at least a first machine-learning model 240 relating physiological state data 204 to prognostic labels using the third training set 200 and generating the at least a prognostic output using the first machine-learning model 240; at least a first machine-learning model 240 may include one or more models that determine a mathematical relationship between physiological state data 204 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithm used to generate first machine-learning model 240 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, prognostic label learner 236 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using third training set 200; the trained network may then be used to apply detected relationships between elements of physiological state data 204 and prognostic labels.

Figure 3:
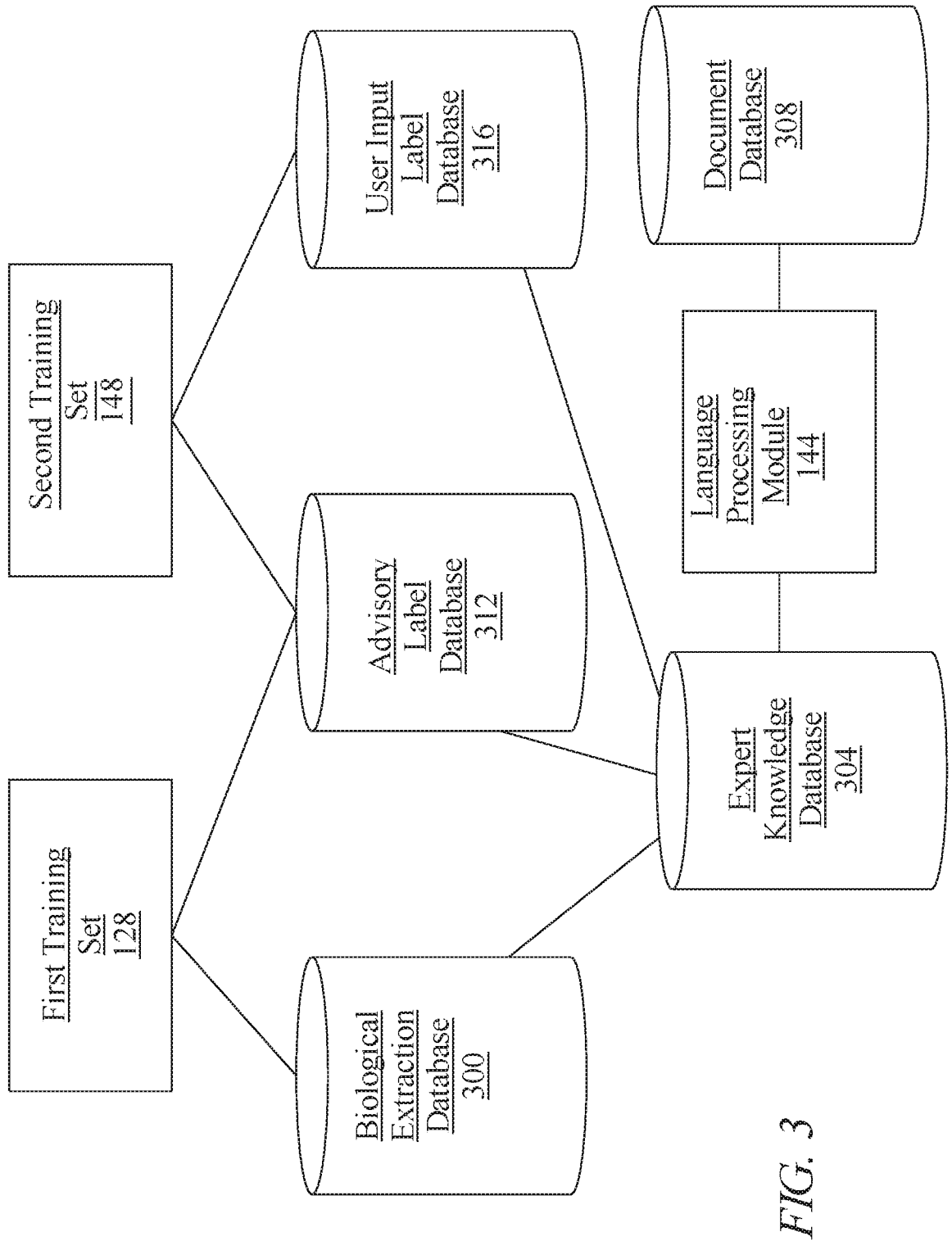
FIG. 3 is a block diagram illustrating embodiments of data storage facilities for use in disclosed systems and methods.

Referring now to FIG. 3, data incorporated in first training set 128 and/or second training set 148 may be incorporated in one or more databases. As a non-limiting example, one or elements of diagnostic output data may be stored in and/or retrieved from a biological extraction database 300. A biological extraction database 300 may include any data structure for ordered storage and retrieval of data, which may be implemented as a hardware or software module. A biological extraction database 300 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 300 may include a plurality of data entries and/or records corresponding to elements of physiological data as described above. Data entries and/or records may describe, without limitation, data concerning particular biological extractions that have been collected; entries may describe reasons for collection of samples, such as without limitation one or more conditions being tested for, which may be listed with related advisory labels. Data entries may include advisory labels and/or other descriptive entries describing results of evaluation of past biological extractions, including diagnoses that were associated with such samples, prognoses and/or conclusions regarding likelihood of future diagnoses that were associated with such samples, and/or other medical or diagnostic conclusions that were derived. Such conclusions may have been generated by diagnostic engine 112 in previous iterations of methods, with or without validation of correctness by medical professionals. Data entries in a biological extraction database 300 may be flagged with or linked to one or more additional elements of information, which may be reflected in data entry cells and/or in linked tables such as tables related by one or more indices in a relational database; one or more additional elements of information may include data associating a biological extraction and/or a person from whom a biological extraction was extracted or received with one or more cohorts, including demographic groupings such as ethnicity, sex, age, income, geographical region, or the like, one or more common diagnoses or physiological attributes shared with other persons having biological extractions reflected in other data entries, or the like. Additional elements of information may include one or more categories of physiological data as described above. Additional elements of information may include descriptions of particular methods used to obtain biological extractions, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 300 may reflect categories, cohorts, and/or populations of data consistently with this disclosure.

With continued reference to FIG. 3, diagnostic engine 112 and/or another device in diagnostic engine 112 may populate one or more fields in biological extraction database 300 using expert information, which may be extracted or retrieved from an expert knowledge database 304. An expert knowledge database 304 may include any data structure and/or data store suitable for use as a biological extraction database 300 as described above. Expert knowledge database 304 may include data entries reflecting one or more expert submissions of data such as may have been submitted according to any process described above in reference to FIGS. 1-2 including without limitation by using first graphical user interface 140 and/or second graphical user interface 160. Expert knowledge database may include one or more fields generated by language processing module 144, such as without limitation fields extracted from one or more documents as described above. For instance, and without limitation, one or more categories of physiological data and/or related advisory labels and/or categories of advisory labels associated with an element of physiological state data as described above may be stored in generalized from in an expert knowledge database 304 and linked to, entered in, or associated with entries in a biological extraction database 300. Documents may be stored and/or retrieved by diagnostic engine 112 and/or language processing module 144 in and/or from a document database 308; document database 308 may include any data structure and/or data store suitable for use as biological extraction database 300 as described above. Documents in document database 308 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

With continued reference to FIG. 3, an advisory label database 312, which may be implemented in any manner suitable for implementation of biological extraction database 300, may be used to store advisory labels used in diagnostic engine 112, including any advisory labels correlated with elements of physiological data in first training set 128 as described above; advisory labels may be linked to or refer to entries in biological extraction database 300 to which advisory labels correspond. Linking may be performed by reference to historical data concerning biological extractions, such as diagnoses, prognoses, and/or other medical conclusions derived from biological extractions in the past; alternatively or additionally, a relationship between an advisory label and a data entry in biological extraction database 300 may be determined by reference to a record in an expert knowledge database 304 linking a given advisory label to a given category of biological extraction as described above. Entries in advisory label database 312 may be associated with one or more categories of advisory labels as described above, for instance using data stored in and/or extracted from an expert knowledge database 304.

With continued reference to FIG. 3, first training set 128 may be populated by retrieval of one or more records from biological extraction database 300 and/or advisor label database 312; in an embodiment, entries retrieved from biological extraction database 300 and/or advisory label database 312 may be filtered and or select via query to match one or more additional elements of information as described above, so as to retrieve a first training set 128 including data belonging to a given cohort, demographic population, or other set, so as to generate outputs as described below that are tailored to a person or persons with regard to whom diagnostic engine 112 classifies biological extractions to advisory labels as set forth in further detail below. Persons skilled in the art, upon reviewing the entirety of this disclosure, will be aware of various ways in which records may be retrieved from biological extraction database 300 and/or advisory label database to generate a first training set to reflect individualized group data pertaining to a person of interest in operation of system and/or method, including without limitation a person with regard to whom at least a biological extraction is being evaluated as described in further detail below. Diagnostic engine 112 may alternatively or additionally receive a first training set 128 and store one or more entries in biological extraction database 300 and/or advisory label database 312 as extracted from elements of first training set 128.

Still referring to FIG. 3, at least a server 104 may include or communicate with a user input label database 316; a user input label database 316 may include any data structure and/or datastore suitable for use as a biological extraction database 300 as described above. A user input label database 316 may include one or more entries listing labels associated with one or more user input datums as described above, including any user input datums correlated with advisory labels in second training set 148 as described above; user input labels may be linked to or refer to entries in advisory label database 312 to which user input labels correspond. Linking may be performed by reference to historical data concerning advisory labels, such as therapies, treatments, and/or lifestyle or dietary choices chosen to alleviate conditions associated with advisory labels in the past; alternatively or additionally, a relationship between a user input label and a data entry in advisory label database 312 may be determined by reference to a record in an expert knowledge database 304 linking a given user input label to a given category of advisory label as described above. Entries in user input label database 312 may be associated with one or more categories of advisory labels as described above, for instance using data stored in and/or extracted from an expert knowledge database 304.

Figure 4:
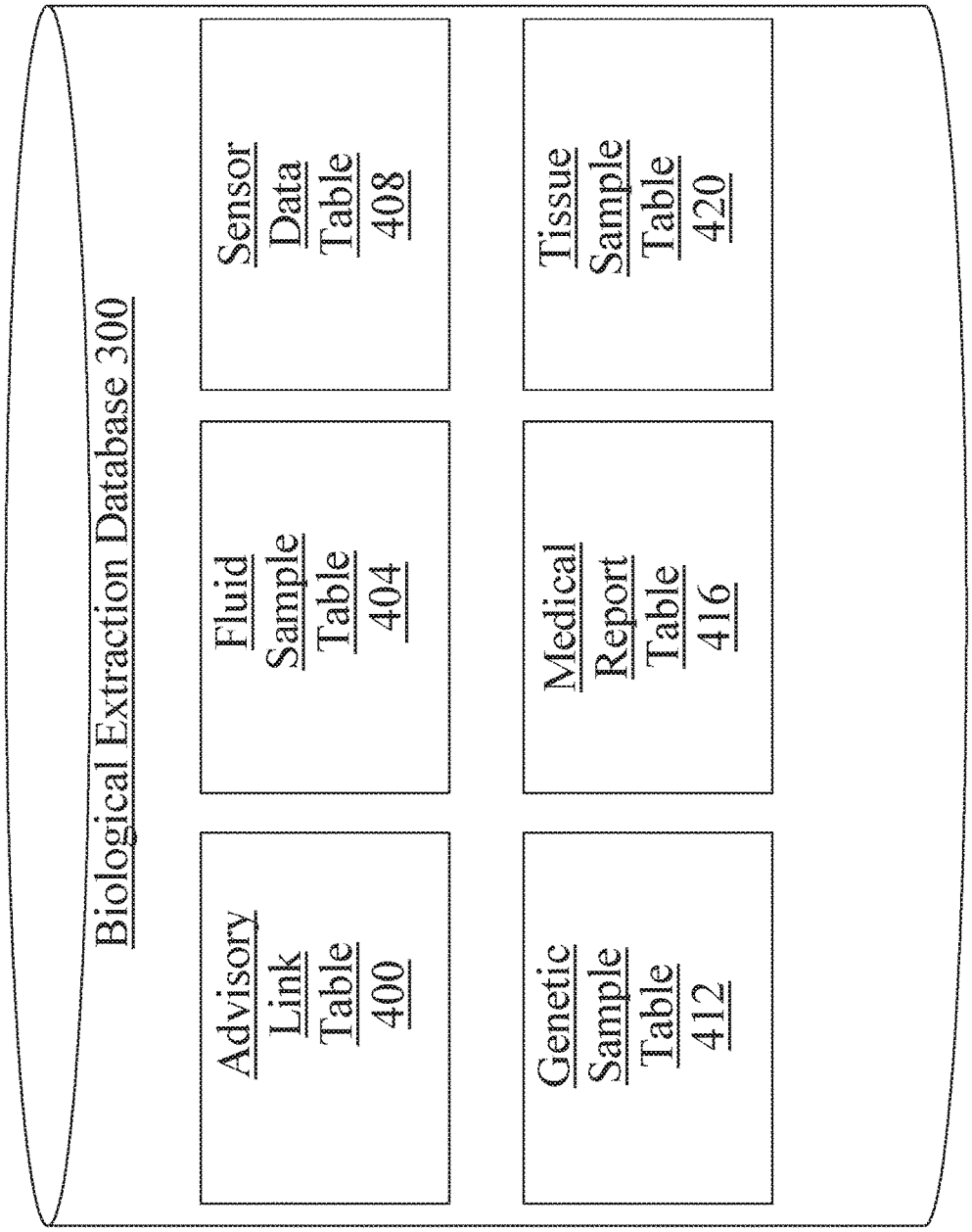
FIG. 4 is a block diagram illustrating an exemplary embodiment of a biological extraction database.

Referring now to FIG. 4, one or more database tables in biological extraction database 300 may include, as a non-limiting example, an advisory link table 400. Advisory link table 400 may be a table relating biological extraction data as described above to advisory labels; for instance, where an expert has entered data relating an advisory label to a category of biological extraction data and/or to an element of biological extraction data via first graphical user interface 140 as described above, one or more rows recording such an entry may be inserted in advisory link table 400. Alternatively or additionally, linking of advisory labels to biological extraction data may be performed entirely in an advisory label database as described below.

With continued reference to FIG. 4, biological extraction database 300 may include tables listing one or more samples according to sample source. For instance, and without limitation, biological extraction database 300 may include a fluid sample table 404 listing samples acquired from a person by extraction of fluids, such as without limitation blood, lymph cerebrospinal fluid, or the like. As another non-limiting example, biological extraction database 300 may include a sensor data table 408, which may list samples acquired using one or more sensors, for instance as described in further detail below. As a further non-limiting example, biological extraction database 300 may include a genetic sample table 412, which may list partial or entire sequences of genetic material. Genetic material may be extracted and amplified, as a non-limiting example, using polymerase chain reactions (PCR) or the like. As a further example, also non-limiting, biological extraction database 300 may include a medical report table 416, which may list textual descriptions of medical tests, including without limitation radiological tests or tests of strength and/or dexterity or the like. Data in medical report table may be sorted and/or categorized using a language processing module, for instance, translating a textual description into a numerical value and a label corresponding to a category of physiological data; this may be performed using any language processing algorithm or algorithms as referred to in this disclosure. As another non-limiting example, biological extraction database 300 may include a tissue sample table 420, which may record biological extractions obtained using tissue samples. Tables presented above are presented for exemplary purposes only; persons skilled in the art will be aware of various ways in which data may be organized in biological extraction database 300 consistently with this disclosure.

Figure 5:
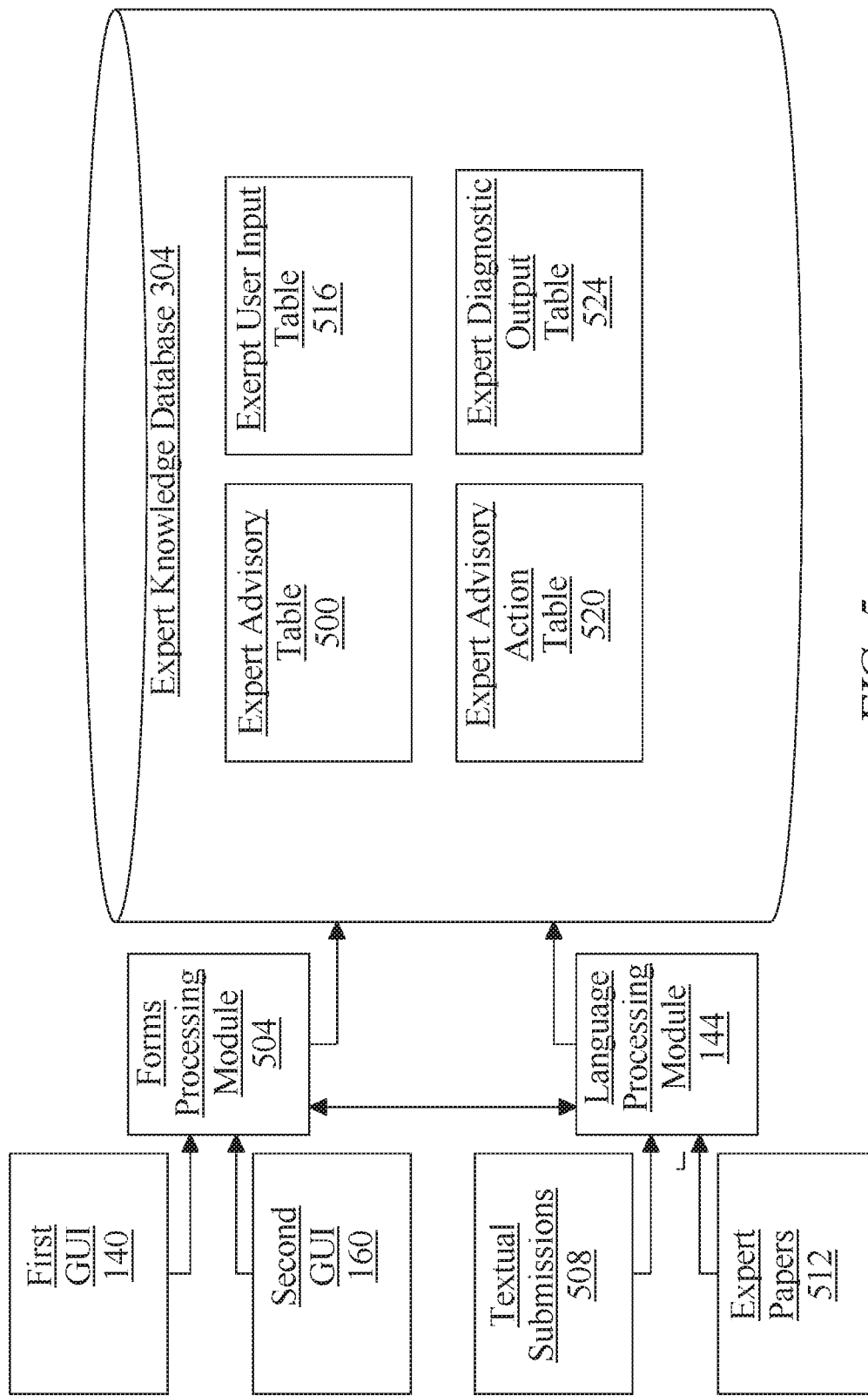
FIG. 5 is a block diagram illustrating an exemplary embodiment of an expert knowledge database.

Referring now to FIG. 5, an exemplary embodiment of an expert knowledge database 304 is illustrated. Expert knowledge database 304 may, as a non-limiting example, organize data stored in the expert knowledge database 304 according to one or more database tables. One or more database tables may be linked to one another by, for instance, common column values. For instance, a common column between two tables of expert knowledge database 304 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in expert knowledge database 304 may include, as a non-limiting example, an expert advisory table 500. Expert advisory table 500 may be a table relating biological extraction data as described above to advisory labels; for instance, where an expert has entered data relating an advisory label to a category of biological extraction data and/or to an element of biological extraction data via first graphical user interface 140 as described above, one or more rows recording such an entry may be inserted in expert advisory table 500. In an embodiment, a forms processing module 504 may sort data entered in a submission via first graphical user interface 140 by, for instance, sorting data from entries in the first graphical user interface 140 to related categories of data; for instance, data entered in an entry relating in the first graphical user interface 140 to an advisory label may be sorted into variables and/or data structures for storage of advisory labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 144 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 508, such as accomplished by filling out a paper or PDF form and/or submitting narrative information, may likewise be processed using language processing module 144. Data may be extracted from expert papers 512, which may include without limitation publications in medical and/or scientific journals, by language processing module 144 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert advisory table 500 may include a single table and/or a plurality of tables; plurality of tables may include tables for particular categories of advisory labels such as a current diagnosis table, a current meditation sequence table, a current spiritual practice table, a current prayer practice, (not shown), to name a few non-limiting examples presented for illustrative purposes only.

With continued reference to FIG. 5, one or more database tables in expert knowledge database 304 may include, an expert user input t able 516, an expert advisory action table 520, and expert diagnostic output table 524, expert data populating such tables may be provided, without limitation, using any process described above, including entry of data from second graphical user interface 160 via forms processing module 504 and/or language processing module 144, processing of textual submissions 508, or processing of expert papers 512. For instance, and without limitation, an expert user input table 516 may list one or categories of user input processes, and/or links of such one or more user inputs processes to advisory labels, as provided by experts according to any method of processing and/or entering expert data as described above. As a further example an expert advisory action table 520 may list one or more expert advisory processes based on instructions for actions a user should take, including without limitation prayer, meditation, yoga, tai-chi, qi-gong, and/or links of such one or more action processes to advisory labels, as provided by experts according to any method of processing and/or entering expert data as described above. As an additional example, an expert diagnostic output table 524 may list one or more categories of diagnostic outputs, and/or links of such one or more diagnostic outputs to advisory labels, as provided by experts according to any method of processing and/or entering expert data as described above. Tables presented above are presented for exemplary purposes only; persons skilled in the art will be aware of various ways in which data may be organized in expert knowledge database 304.

Figure 6:
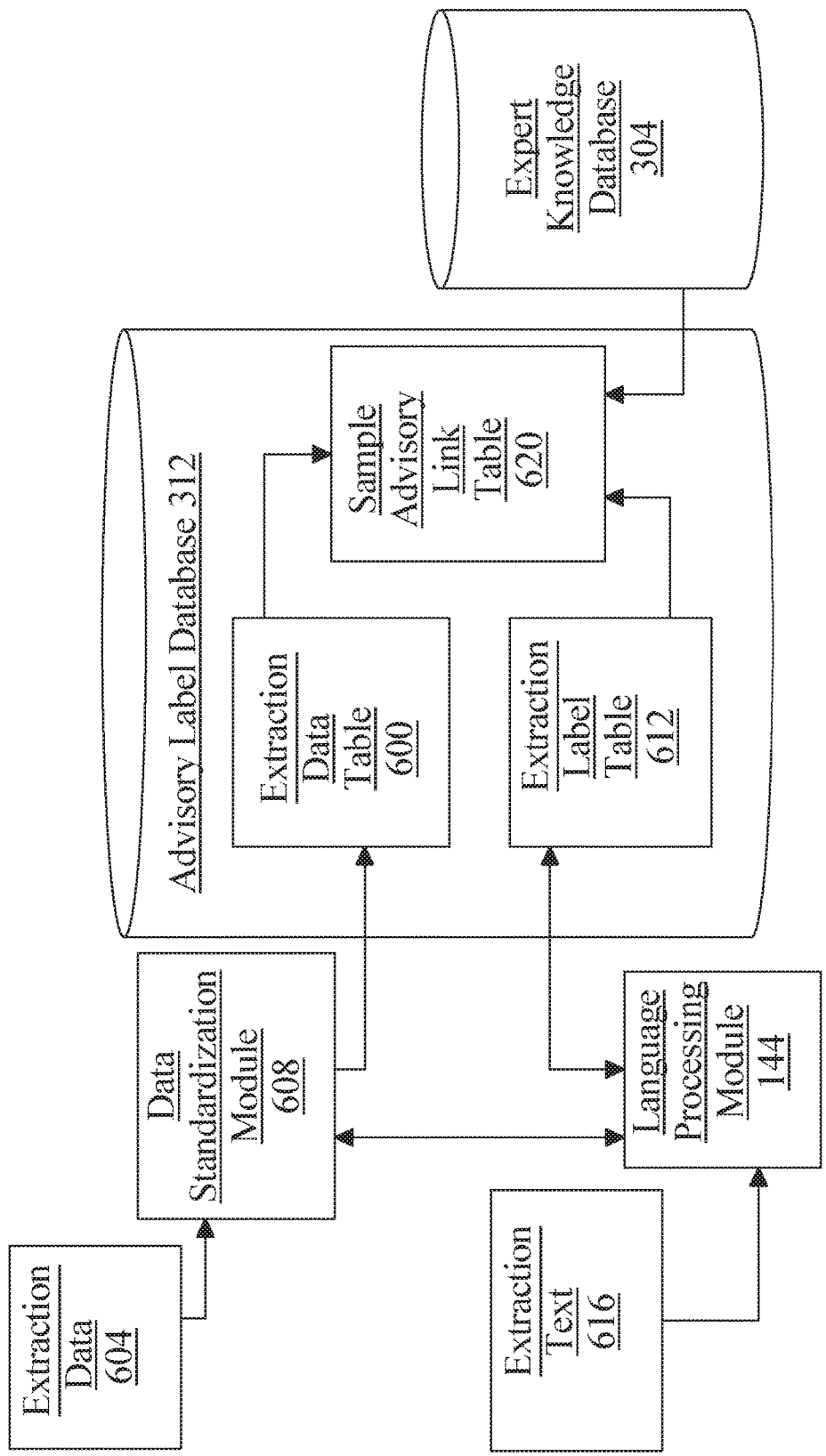
FIG. 6 is a block diagram illustrating an exemplary embodiment of an advisory label database.

Referring now to FIG. 6, an exemplary embodiment of an advisory label database 312 is illustrated. Advisory label database 312 may, as a non-limiting example, organize data stored in the advisory label database 312 according to one or more database tables. One or more database tables may be linked to one another by, for instance, common column values. For instance, a common column between two tables of advisory label database 312 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, one or more database tables in advisory label database 312 may include, as a non-limiting example, an extraction data table 600. Extraction data table 600 may be a table listing sample data, along with, for instance, one or more linking columns to link such data to other information stored in advisory label database 312. In an embodiment, extraction data 604 may be acquired, for instance from biological extraction database 300, in a raw or unsorted form, and may be translated into standard forms, such as standard units of measurement, labels associated with particular physiological data values, or the like; this may be accomplished using a data standardization module 608, which may perform unit conversions. Data standardization module 608 may alternatively or additionally map textual information, such as labels describing values tested for or the like, using language processing module 144 or equivalent components and/or algorithms thereto.

Continuing to refer to FIG. 6, advisory label database 312 may include an extraction label table 612; extraction label table 612 may list advisory labels received with and/or extracted from biological extractions, for instance as received in the form of extraction text 616. A language processing module 144 may compare textual information so received to advisory labels and/or form new advisory labels according to any suitable process as described above. Extraction advisory link table 620 may combine extractions with advisory labels, as acquired from extraction label table and/or expert knowledge database 304; combination may be performed by listing together in rows or by relating indices or common columns of two or more tables to each other. Tables presented above are presented for exemplary purposes only; persons skilled in the art will be aware of various ways in which data may be organized in expert knowledge database 304 consistently with this disclosure.

Figure 7:
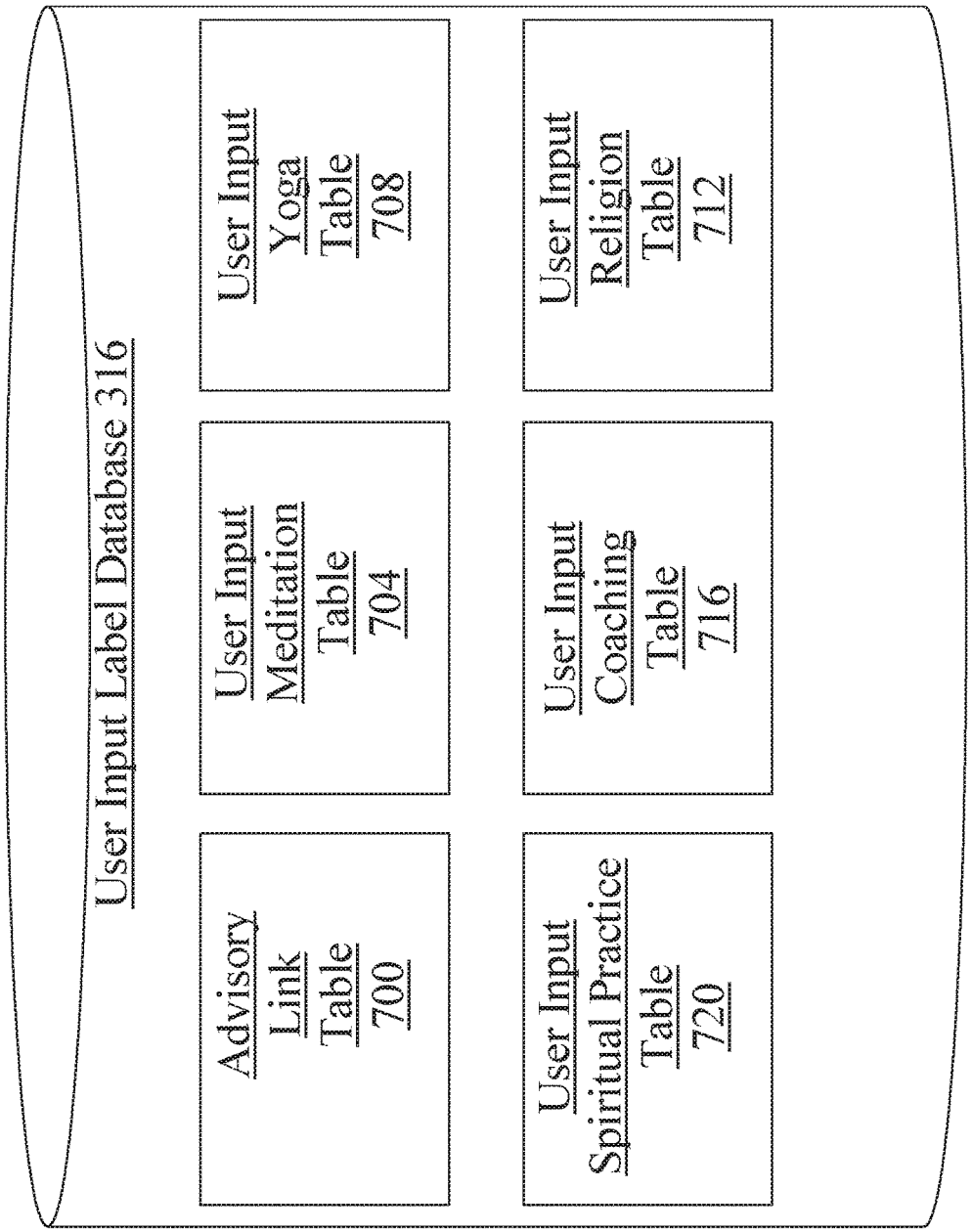
FIG. 7 is a block diagram illustrating an exemplary embodiment of a user input label database.

Referring now to FIG. 7, an exemplary embodiment of a user input label database 316 is illustrated. User input label database 316 may, as a non-limiting example, organize data stored in the user input label database 316 according to one or more database tables. One or more database tables may be linked to one another by, for instance, common column values. For instance, a common column between two tables of user input label database 316 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 7, user input label database 316 may include an advisory link table 700; advisory link table may link user input data to advisory label data, using any suitable method for linking data in two or more tables as described above. User input label database 316 may include a user input meditation table 704, which may list one or more user inputs based on meditation instructions, and/or links of such one or more user input processes to advisory labels, for instance as provided by experts according to any method of processing and/or entering expert data as described above, and/or using one or more machine-learning processes as set forth in further detail below. As a further example a user input yoga table 708 may list one or more user input processes based on instructions for yoga, and/or links of such one or more user input processes to advisory labels, as provided by experts according to any method of processing and/or entering expert data as described above and/or using one or more machine-learning processes as set forth in further detail below. As an additional example, a user input religion table 712 may list one or more user input processes based on a particular religious preference and/or religious instruction, and/or links of such one or more user input processes to advisory labels, as provided by experts according to any method of processing and/or entering expert data as described above and/or using one or more machine-learning processes as set forth in further detail below. As a further non-limiting example, a user input coaching table 716 may list one or more user input processes based on coaching, including without limitation requests for spiritual coaching, life coaching, and/or spiritual life coaching and/or links of such one or more user input processes to advisory labels, as provided by experts according to any method of processing and/or entering expert data as described above and/or using one or more machine-learning processes as set forth in further detail below. As an additional example, a user input spiritual practice table 720 may list one or more user input processes for developing a spiritual practice; spiritual practice may include a desire to develop a spiritual practice and/or to further developing an already existing spiritual practice; this may be acquired using expert submission as described above and/or using one or more machine-learning processes as set forth in further detail below. Tables presented above are presented for exemplary purposes only; persons skilled in the art will be aware of various ways in which data may be organized in user input label database 316 consistently with this disclosure.

Figure 8:
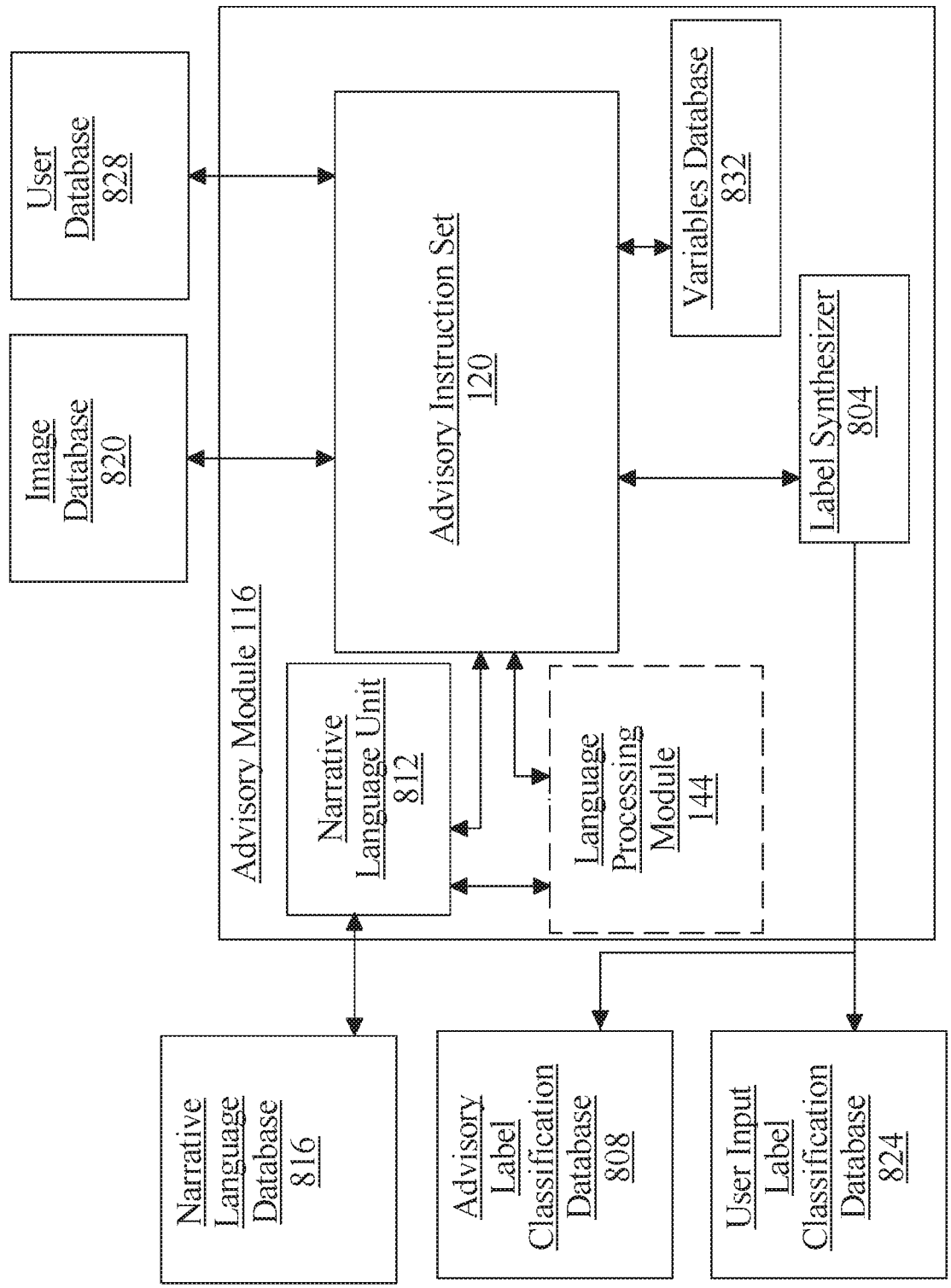
FIG. 8 is a block diagram illustrating an exemplary embodiment of an advisory module and associated system elements.

Referring now to FIG. 8, an exemplary embodiment of advisory module 116 is illustrated. Advisory module 116 is configured to receive at least an advisory input from an advisory client device and generate at least an advisory instruction set as a function of the at least a user input datum and the at least an advisory input. In an embodiment, advisory module 116 may include a label synthesizer 804. Label synthesizer 804 may include any suitable software or hardware module. In an embodiment, label synthesizer 804 may be designed and configured to combine a plurality of labels in at least an advisory instruction set together to provide maximally efficient data presentation. Combination of labels together may include elimination of duplicate information. For instance, label synthesizer 804 and/or at least a server 104 may be designed and configure to determine a first advisory label of the at least an advisory label is a duplicate of a second advisory label of the at least an advisory label and eliminate the first advisory label. Determination that a first advisory label is a duplicate of a second advisory label may include determining that the first advisory label is identical to the second advisory label; for instance, an advisory label generated from test data presented in one biological extraction of at least a biological extraction may be the same as an advisory label generated from test data presented in a second biological extraction of at least a biological extraction. As a further non-limiting example, a first advisory label may be synonymous with a second advisory label, where detection of synonymous labels may be performed, without limitation, by a language processing module 144 as described above.

Continuing to refer to FIG. 8, label synthesizer 804 may group user input labels according to one or more classification systems relating the user input labels to each other. For instance, advisory module 116 and/or label synthesizer 804 may be configured to determine that a first user input label of the at least a user input label and a second user input label of the at least a user input label belong to a shared category. A shared category may be a category of conditions or tendencies toward a future condition to which each of first user input label and second user input label belongs; as an example, a meditation sequence and a yoga sequence may each be examples of a spiritual practice, for instance, which may in turn share a category with tai chi sequence, Reiki sequence, prayer sequence, scripture sequence or the like. Shared category and/or categories may be associated with advisory labels as well. A given advisory label may belong to a plurality of overlapping categories. Advisory module 116 may be configured to add a category label associated with a shared category to at least an advisory instruction set, where addition of the label may include addition of the label and/or a datum linked to the label, such as a textual or narrative description. In an embodiment, advisory module 116 may consult user input label classification database 824. In an embodiment, relationships between advisory labels and categories may be retrieved from an advisory label classification database 808, for instance by generating a query using one or more advisory labels of at least an advisory output, entering the query, and receiving one or more categories matching the query from the advisory label classification database 808.

With continued reference to FIG. 8, advisory module 116 may be configured to generate at least an advisory instruction set by converting one or more advisory labels into narrative language. As a non-limiting example, advisory module 116 may include a narrative language unit 812, which may be configured to determine an element of narrative language associated with at least an advisory label and/or at least a user input label and include the element of narrative language in at least an advisory instruction set. Narrative language unit 812 may implement this, without limitation, by using a language processing module 144 to detect one or more associations between advisory labels, user input labels, and/or lists of advisory labels, user input labels, and phrases and/or statements of narrative language. Alternatively or additionally, narrative language unit 812 may retrieve one or more elements of narrative language from a narrative language database 816, which may contain one or more tables associating advisory labels, user input labels, and/or groups of advisory labels and user input labels with words, sentences, and/or phrases of narrative language. One or more elements of narrative language may be included in at least an advisory instruction set, for instance for display to a user as text describing a current spiritual status of the user. At least an advisory instruction set may further include one or more images; one or more images may be retrieved by advisory module 116 from an image database 820, which may contain one or more tables associating advisory labels, groups of advisory labels, user input labels, groups of user input labels or the like with one or more images.

With continued reference to FIG. 8, advisory module 116 may be configured to generate at least an advisory instruction set by converting one or more user input labels into narrative language. As a non-limiting example, advisory module 116 may consult narrative language unit 812, which may be configured to determine an element of narrative language associated with at least a user input and include the element of narrative language in at least an advisory instruction set. Narrative language unit 812 may implement this, without limitation, by using a language processing module 144 to detect one or more associations between user inputs, user input labels, or lists of user input labels, and phrases and/or statements of narrative language. Alternatively or additionally, narrative language unit 812 may retrieve one or more elements of narrative language from narrative language database 816, which may contain one or more tables associating user inputs, user input labels and/or groups of user input labels with words, sentences, and/or phrases of narrative language. One or more elements of narrative language may be included in at least an advisory instruction set 120, for instance for display to a user as text describing a current meditation sequence of the user. At least an advisory instruction set may further include one or more images; one or more images may be retrieved by advisory module 116 from an image database 820, which may contain one or more tables associating user input labels, groups of user input labels, or the like with one or more images.

With continued reference to FIG. 8, advisory module 116 may be configured to receive at least an advisory input and generate at least an advisory instruction set 120 as a function of the at least a user input datum and the at least an advisory input. In an embodiment, advisory module 116 may consult user database 828 to seek information about a particular user preference. At least a user input datum, may include an element of data describing the user, user needs, and/or user preferences in regard to spirituality, life coaching, and/or spiritual life coaching. At least a user input datum may include a preference for a particular style or type of religious practice. At least a user input datum may include a preference for a certain amount of time to be devoted each day or each week to a spiritual practice. For example, a user may have a preference to implement a spiritual practice three days each week for thirty minutes each day. At least an advisory instruction set may be generated as a function of the at least an advisory input. At least an advisory input may include any of the advisory inputs as described above in reference to FIG. 1. At least an advisory input may include a recommendation for a user engage in a certain spiritual practice because of a current diagnosis of a user. For example, an informed advisor such as a user's functional medicine doctor may generate at least an advisory input containing a suggestion for user to practice a meditation sequence throughout user's cancer diagnosis and treatment. In yet another non-limiting example, an informed advisor such as user' yoga coach may generate at least an advisory input containing a yoga flow sequence user should practice to aid user in loosening up user's stiff neck. In yet another non-limiting example, at least an advisory input may include a suggestion for a user to try a specific prayer sequence as a result of user's desire to form a relationship with a higher power.

Figure 9:
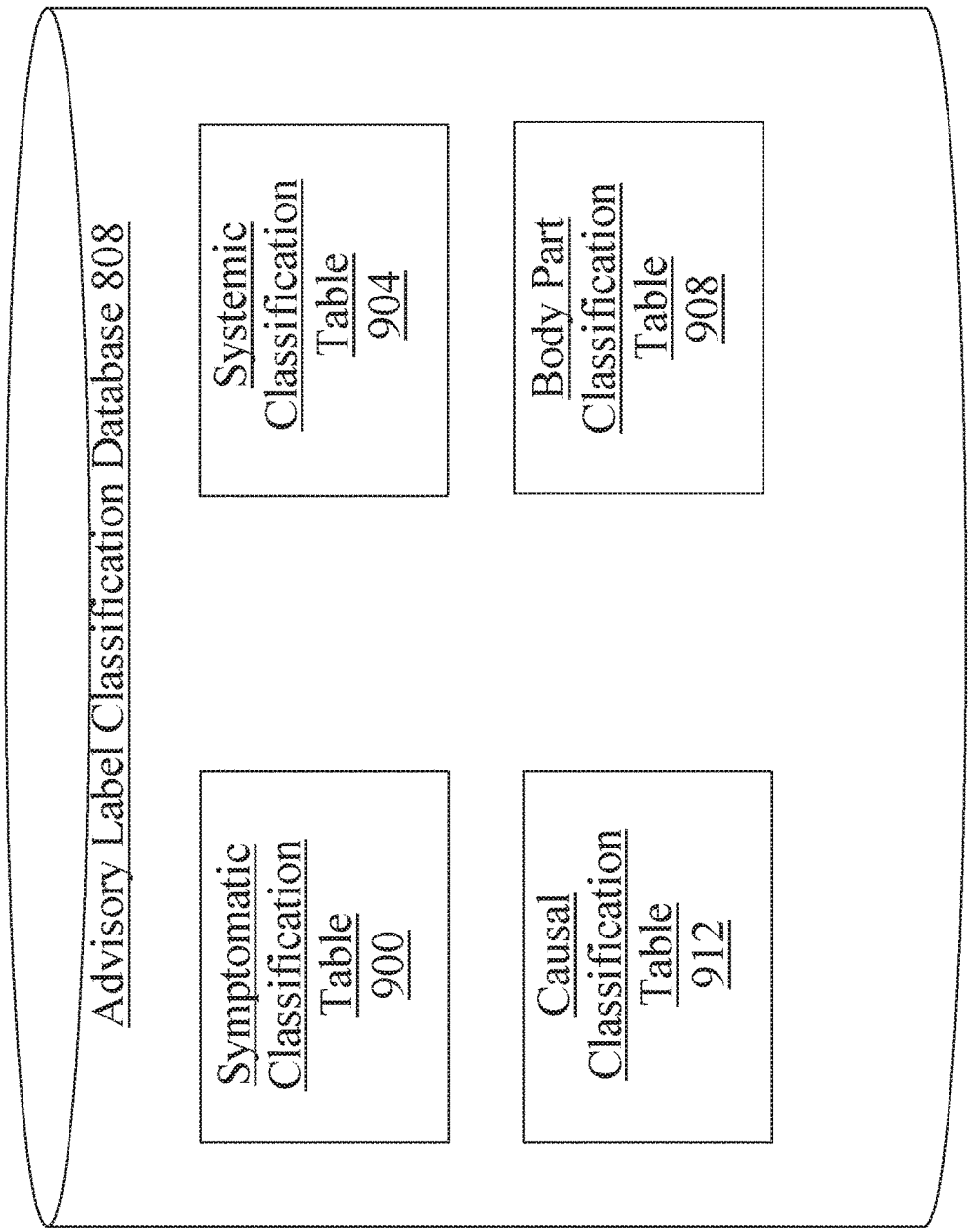
FIG. 9 is a block diagram illustrating an exemplary embodiment of an advisory label classification database.

Referring now to FIG. 9, an exemplary embodiment of an advisory label classification database 808 is illustrated. Advisory label classification database 808 may be implemented as any database and/or datastore suitable for use as biological extraction database 300 as described above. One or more database tables in advisory label classification database 808 may include, without limitation, a symptomatic classification table 900; symptomatic classification table 900 may relate each advisory label to one or more categories of symptoms associated with that advisory label. As a non-limiting example, symptomatic classification table 900 may include records indicating that anxiety and obsessive compulsive disorder symptoms are both reduced with spiritual practices including yoga, Reiki, and meditation. One or more database tables in advisory label classification database 808 may include, without limitation, a systemic classification table 904; systemic classification table 904 may relate each advisory label to one or more systems associated with that advisory label. As a non-limiting example, systemic classification table 904 may include records indicating each of prayer sequences and religious instruction reduce all-cause mortality and impact longevity. In yet another non-limiting example, systemic classification table 904 may include records indicating meditation practices reduce systemic blood pressure and reduce all-cause mortality. One or more database tables in advisory label classification database 808 may include, without limitation, a body part classification table 908; body part classification table 908 may relate each advisory label to one or more body parts associated with that advisory label. As a non-limiting example, body part classification table 908 may include records indicating a yoga practices reduces neck pain and low back pain. One or more database tables in advisory label classification database 808 may include, without limitation, a causal classification table 912; causal classification table 912 may relate each advisory label to one or more causes associated with that advisory label. As a non-limiting example, causal classification table 912 may include records indicating each of depression and schizophrenia may be improved with a spiritual practice. The above-described tables, and entries therein, are provided solely for exemplary purposes. Persons skilled in the art, upon reviewing the entirety of this disclosure, will be aware of various additional examples for tables and/or relationships that may be included or recorded in advisory classification table consistently with this disclosure.

Figure 10:
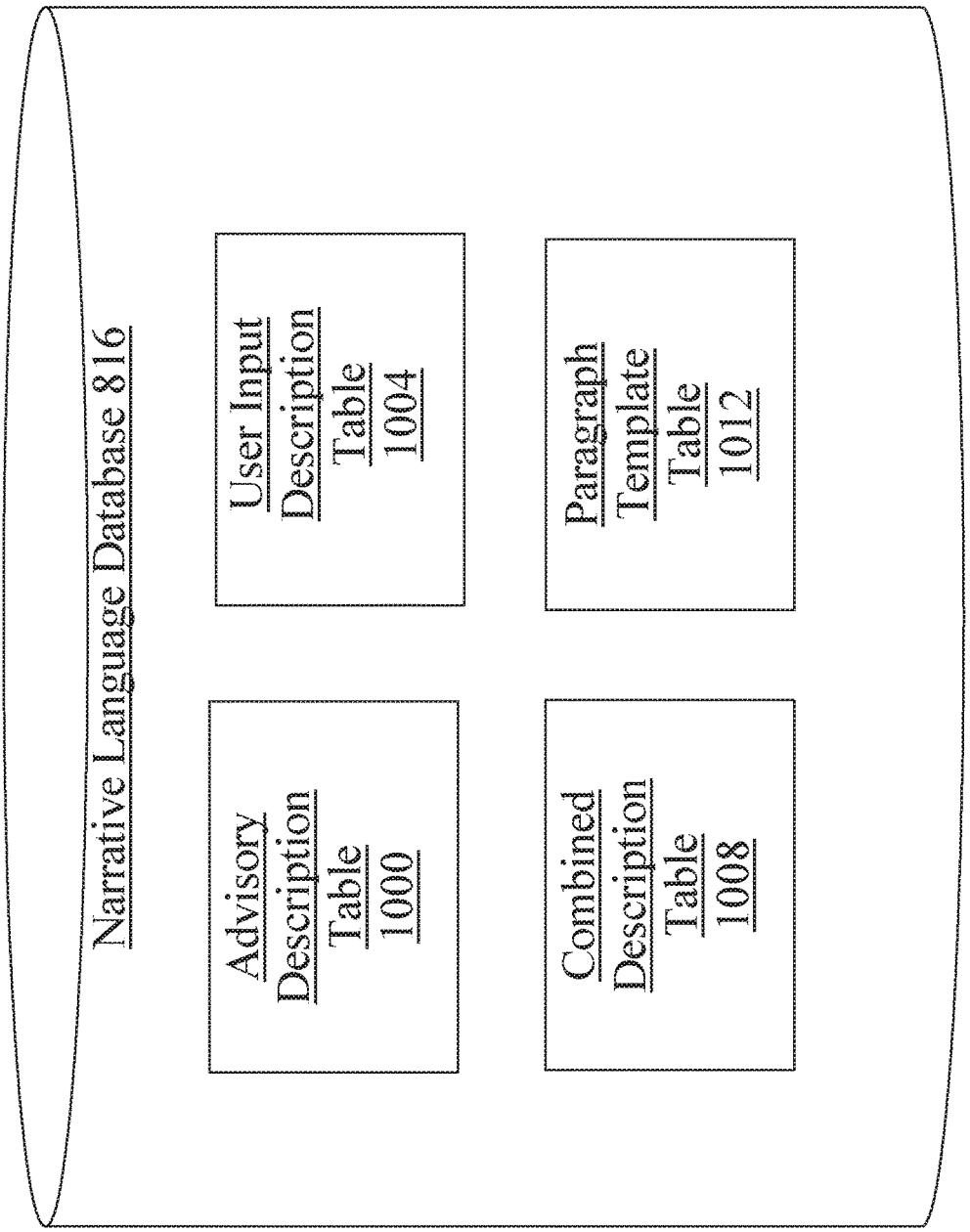
FIG. 10 is a block diagram illustrating an exemplary embodiment of a narrative language database.

Referring now to FIG. 10, and exemplary embodiment of a narrative language database 816 is illustrated. Narrative language database 816 may be implemented as any database and/or datastore suitable for use as biological extraction database 300 as described above. One or more database tables in narrative language database 816 may include, without limitation, an advisory description table 1000, which may link advisory labels to narrative descriptions associated with advisory labels. One or more database tables in narrative language database 816 may include, without limitation, a user input description table 1004, which may link user input labels to narrative descriptions associated with user input labels. One or more database tables in narrative language database 816 may include, without limitation, a combined description table 1008, which may link combinations of advisory labels and user input labels to narrative descriptions associated with the combinations. One or more database tables in narrative language database 816 may include, without limitation, a narrative template table 1012, which may contain one or more templates of phrases, sentences, paragraphs, pages, reports, or the like into which images and text, such as images obtained from image database 820 and text obtained from advisory description table 1000, user input description table 1004, and combined description table 1008 may be inserted. As a non-limiting example, a template may include a combination of words and/or phrases to be displayed as narrative language with one or more labels, variable names, or other indicators representing "blanks" to be filled in with numerical or textual values provided using diagnostic output elements; for instance, a template sentence may be rendered as "Your cholesterol levels are <CLVL>," where "<CLVL>" is parsed by narrative language unit 812 as an instruction to insert a variable containing a cholesterol level reading in place of "<CLVL>" in the narrative language generated using the template. Such labels, variable-insertion markers, or the like may be used to insert any numerical or textual datum from diagnostic output and/or user input into any phrase, sentence, paragraph, page, or the like; persons skilled in the art, upon reviewing the entirety of this disclosure, will be aware of various ways in which templates and variables may be combined to generate narrative language as described in this disclosure. Tables in narrative description table 816 may be populated, as a non-limiting example, using submissions from experts, which may be collected according to any processes described above. Persons skilled in the art, upon reviewing the entirety of this disclosure, will be aware of various way sin which entries in narrative description table 816 may be categorized and/or organized.

Figure 11:
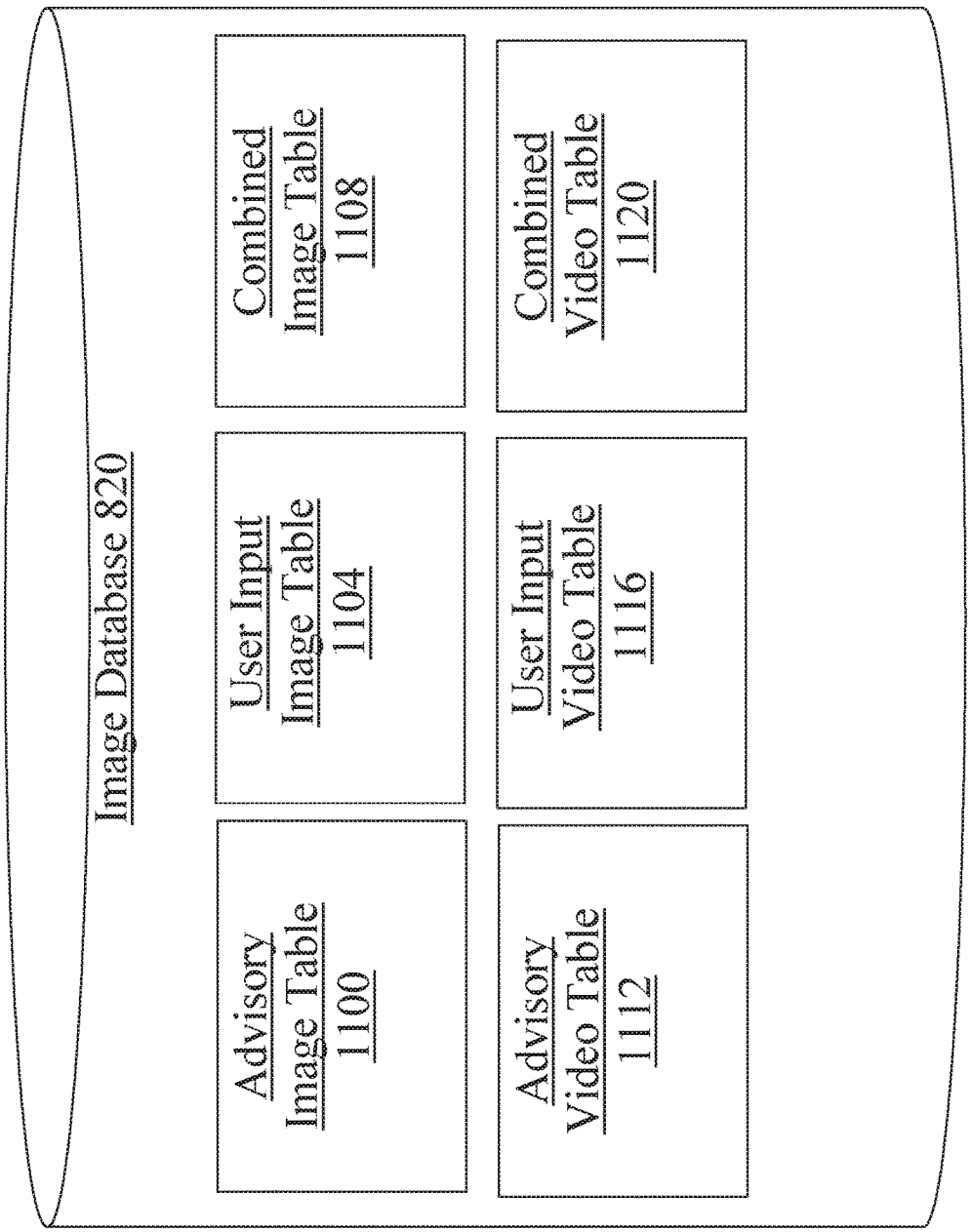
FIG. 11 is a block diagram illustrating an exemplary embodiment of an image database.

Referring now to FIG. 11, an exemplary embodiment of an image database 820 is illustrated. Image database 820 may be implemented as any database and/or datastore suitable for use as biological extraction database 300 as described above. One or more database tables in image database 820 may include, without limitation, an advisory image table 1100, which may link advisory labels to images associated with advisory labels. One or more database tables in image database 820 may include, without limitation, a user input image table 1104, which may link user input labels to images associated with user input labels. One or more database tables in image database 820 may include, without limitation, a combined description table 1108, which may link combinations of advisory labels and user input labels to images associated with the combinations. One or more database tables in image database 820 may include, without limitation, an advisory video table 812, which may link advisory labels to videos associated with advisory labels. One or more database tables in image database 820 may include, without limitation, a user video table 1116, which may link user input labels to videos associated with user input labels. One or more database tables in image database 820 may include, without limitation, a combined video table 1120, which may link combinations of advisory labels and user input labels to videos associated with the combinations. Tables in image database 820 may be populated, without limitation, by submissions by experts, which may be provided according to any process or process steps described in this disclosure for collection of expert submissions.

Figure 12:
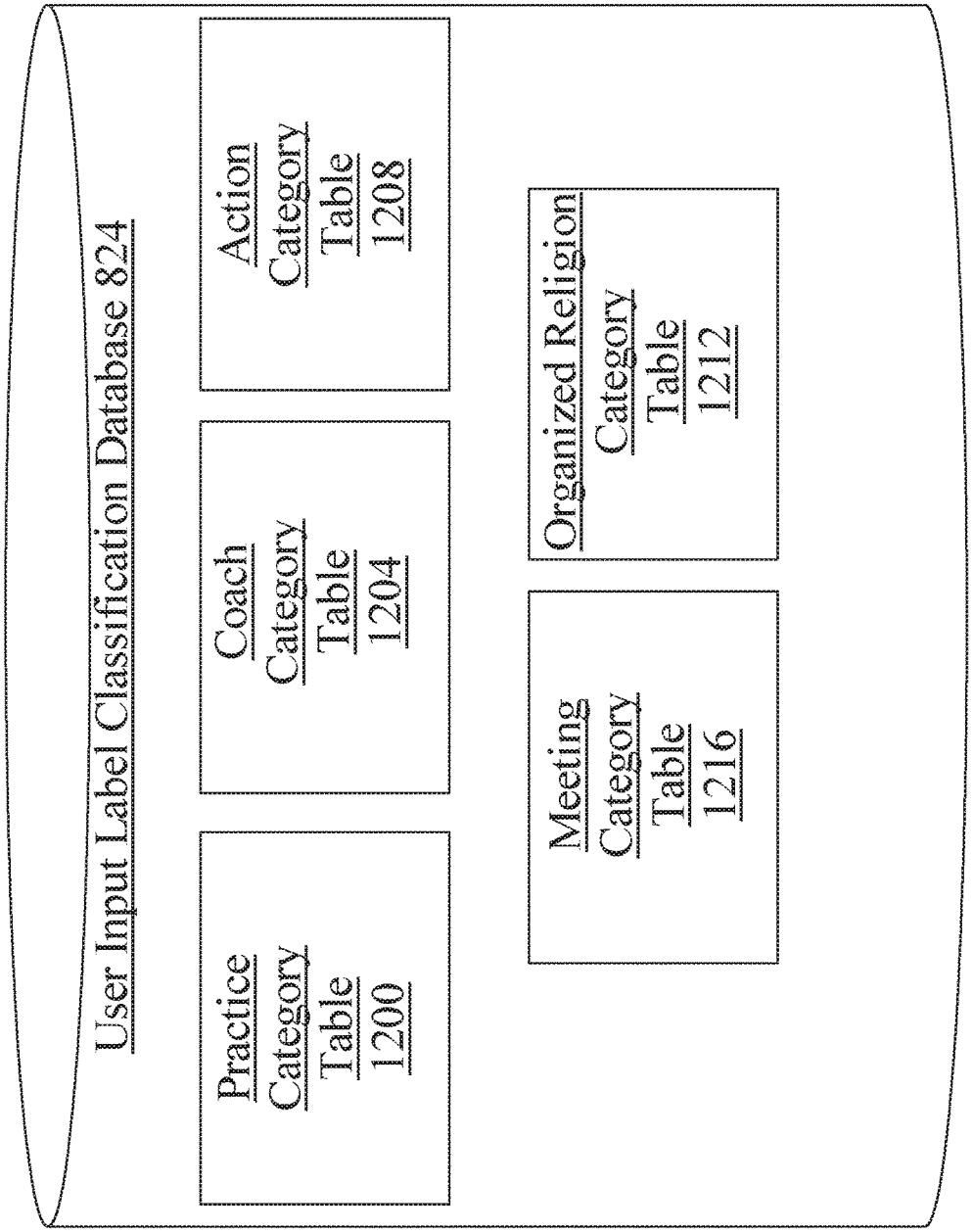
FIG. 12 is a block diagram illustrating an exemplary embodiment of a user input label classification database.

Referring now to FIG. 12, an exemplary embodiment of a user input label classification database 824 is illustrated. User input label classification database 824 may be implemented as any database and/or datastore suitable for use as biological extraction database 300 as described above. One or more database tables in user input label classification database 824 may include, without limitation, a practice category table 1200; practice category 1200 may relate each user input label to one or more categories associated with that user input label. As a non-limiting example, practice category table 1200 may include records indicating that each of a plan to initiate a spiritual practice, develop a spiritual practice, and/or further deepen an already existing spiritual practice. One or more database tables in user input label classification database 824 may include, without limitation, a coach category table 1204; coach category table 1204 may relate each user input label pertaining to coaching to one or more categories associated with that user input label. As a non-limiting example, coach category table 1204 may include records indicating a desire to implement spiritual changes and/or life changes with the use of a spiritual coach, life coach, and/or spiritual life coach. One or more database tables in user input label classification database 824 may include, without limitation, an action category table 1208; action category table 1208 may relate each user input label pertaining to an action to one or more categories associated with that user input label. As a non-limiting example, action category table 1208 may include records indicating that each of a plan for a daily prayer sequence or attending a daily lecture by a pastor at a church qualifies as an action plan. One or more database tables in user input label classification database 824 may include, without limitation, an organized religion category table 1212; organized religion category table 1212 may relate each user input label associated with an organized to one or more categories associated with that user input label. As a non-limiting example, organized religion category table 1212 may include records indicating that each of a plan to become a member of Jewish faith or to attend a Christian religious instruction class qualifies as a form of organized religious practice. One or more database tables in user input label classification database 824 may include, without limitation, a meeting category table 1216; meeting category table 1216 may relate each user input label pertaining to a meeting to one or more categories associated with that user input label. As a non-limiting example, meeting category table 1216 may include records indicating that each of a plan to attend a yoga class or to attend a 12-step program belongs to a category of meetings to aid spiritual development. In an embodiment, user input labels may be mapped to each table contained within user input label classification database 824 using practice category table 1200. The above-described tables, and entries therein, are provided solely for exemplary purposes. Persons skilled in the art, upon reviewing the entirety of this disclosure, will be aware of various additional examples for tables and/or relationships that may be included or recorded in ameliorative classification table consistently with this disclosure.

Figure 13:
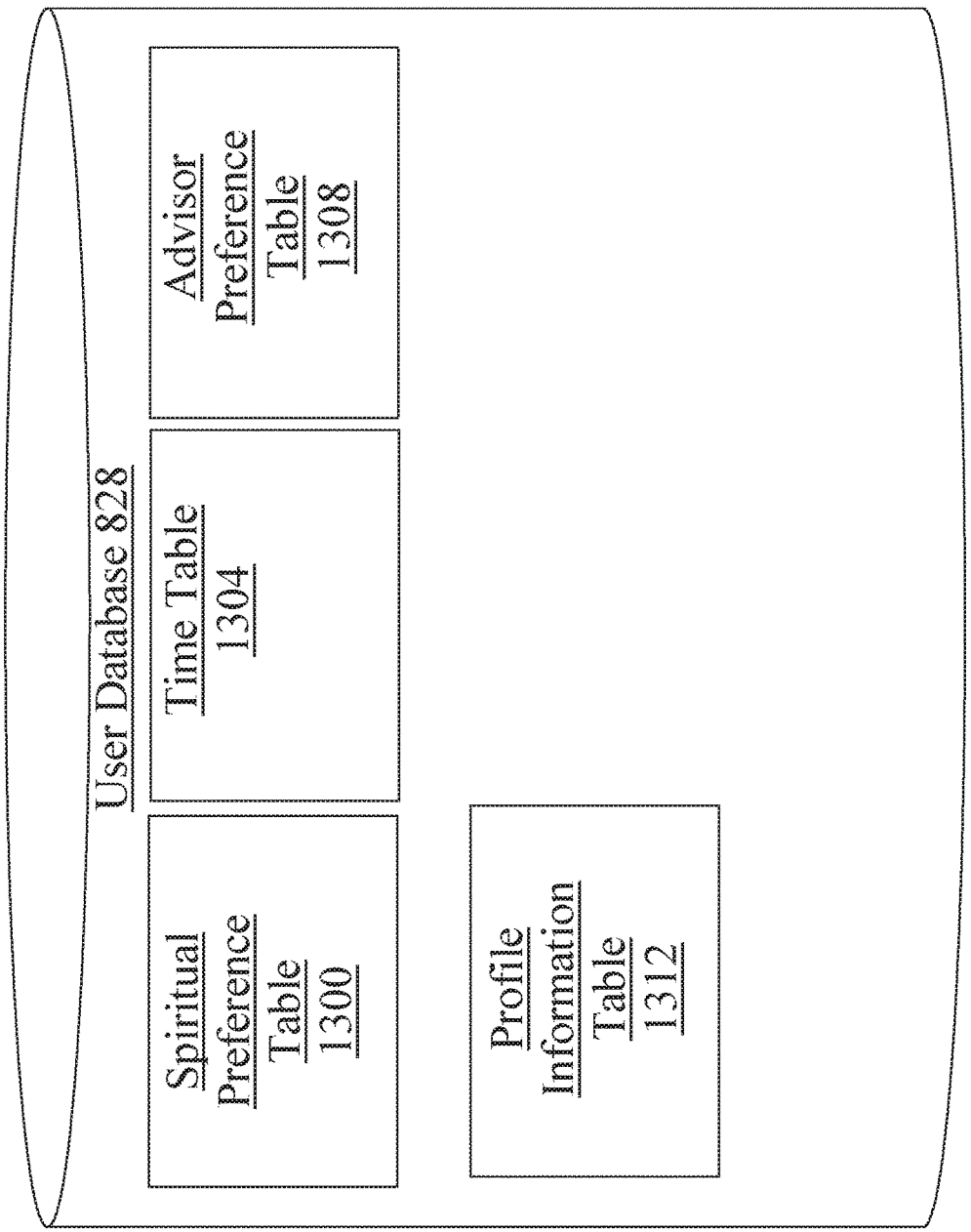
FIG. 13 is a block diagram illustrating an exemplary embodiment of user database.

Referring to FIG. 13, an exemplary embodiment of a user database 828 is illustrated. User database 828 may be implemented as any database and/or datastore suitable for use as biological extraction database 300 as described above. One or more database tables in user database 828 may include, without limitation, a spiritual preference table 1300; spiritual preference table 1300 may include information pertaining to a user's preference for one or more spiritual practices. For example, spiritual preference table 1300 may include information describing a user's preference for a particular spiritual practice such as Reiki, or user's preference for a particular type of organized religion and/or religious instruction such as preference for Christianity or Episcopalian faith. One or more database tables in user database 828 may include, without limitation, a timetable 1304; timetable may include information describing a user's preference to dedicate a certain amount of time each day or week to spirituality and/or developing a spiritual practice. For example, timetable 1304 may include information describing a user's preference to engage in a spiritual practice three days each week or a user's desire to set aside fifteen minutes each morning to devote to a spiritual practice. One or more database tables in user database 828 may include, without limitation, an advisor preference table 1308; advisor preference table 1308 may list one or more informed advisors, as described in further detail below, who user prefers to provide advice and/or services to user, and/or one or more informed advisors who have been selected to provide advice and/or services to the user based on user's preference. Advisor preference table 1308 may include information such as a user's preference to attend a particular yoga teacher's class or a user's preference for a religious teacher with certain credentials or training. One or more database tables in user database 828 may include, without limitation, a profile information table 1312; profile information table may include any user profile information, including without limitation current and/or former residential, vacation, and/or mailing addresses, one or more telephone numbers, one or more email addresses, date of birth, family information, or the like.

Figure 14:
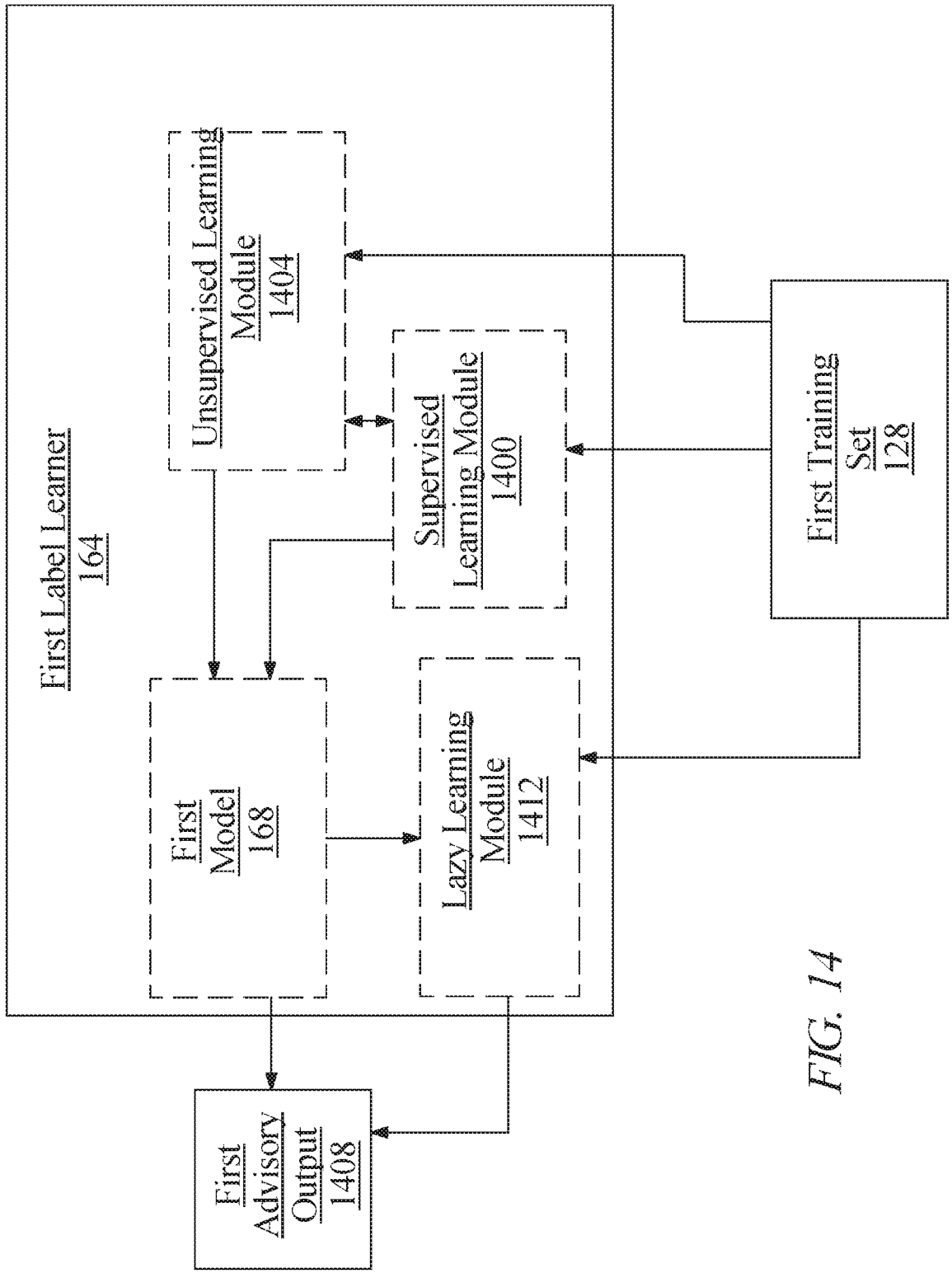
FIG. 14 is a block diagram illustrating an exemplary embodiment of a first label learner and associated system elements.

Referring now to FIG. 14, an exemplary embodiment of first label learner 164 is illustrated. Machine-learning algorithms used by first label learner 164 may include supervised machine-learning algorithms, which may, as a non-limiting example be executed using a supervised learning module 1400 executing on at least a server 104 and/or on another computing device in communication with at least a server 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of diagnostic outputs as inputs, advisory labels as outputs, and a scoring function representing a desired form of relationship to be detected between elements of diagnostic outputs and advisory labels; scoring function may, for instance, seek to maximize the probability that a given element of diagnostic output and/or combination of elements of diagnostic output is associated with a given advisory label and/or combination of advisory labels to minimize the probability that a given element of diagnostic output and/or combination of elements of diagnostic output is not associated with a given advisory label and/or combination of advisory labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 128. Persons skilled in the art, upon reviewing the entirety of this disclosure, will be aware of various possible variations of supervised machine learning algorithms that may be used to determine relation between elements of diagnostic output and advisory labels. In an embodiment, one or more supervised machine-learning algorithms may be restricted to a particular domain for instance, a supervised machine-learning process may be performed with respect to a given set of parameters and/or categories of parameters that have been suspected to be related to a given set of advisory labels, and/or are specified as linked to a medical specialty and/or field of medicine covering a particular set of advisory labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions and correlated spiritual guidance and/or spiritual interventions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate advisory labels. Additional supervised learning processes may be performed without domain restrictions to detect, for instance, previously unknown and/or unsuspected relationships between diagnostic output and advisory labels.

With continued reference to FIG. 14, machine-learning algorithms may include unsupervised processes; unsupervised processes may, as a non-limiting example, be executed by an unsupervised learning module 1404 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, first label learner 164 and/or at least a server 104 may perform an unsupervised machine learning process on first training set 128, which may cluster data of first training set 128 according to detected relationships between elements of the first training set 128, including without limitation correlations of elements of diagnostic output to each other and correlations of advisory labels to each other; such relations may then be combined with supervised machine learning results to add new criteria for first label learner 164 to apply in relating diagnostic output to advisory labels. As a non-limiting, illustrative example, an unsupervised process may determine that a first element of user physiological data acquired in a blood test correlates closely with a second element of user physiological data, where the first element has been linked via supervised learning processes to a given advisory label, but the second has not; for instance, the second element may not have been defined as an input for the supervised learning process, or may pertain to a domain outside of a domain limitation for the supervised learning process. Continuing the example a close correlation between first element of user physiological data and second element of user physiological data may indicate that the second element is also a good predictor for the advisory label; second element may be included in a new supervised process to derive a relationship or may be used as a synonym or proxy for the first physiological data element by first label learner 164.

Still referring to FIG. 14, at least a server 104 and/or first label learner 164 may detect further significant categories of user physiological data, relationships of such categories to advisory labels, and/or categories of advisory labels using machine-learning processes, including without limitation unsupervised machine-learning processes as described above; such newly identified categories, as well as categories entered by experts in free-form fields as described above, may be added to pre-populated lists of categories, lists used to identify language elements for language processing module 144, and/or lists used to identify and/or score categories detected in documents, as described above. In an embodiment, as additional data is added to system 100, first label learner 164 and/or at least a server 104 may continuously or iteratively perform unsupervised machine-learning processes to detect relationships between different elements of the added and/or overall data; in an embodiment, this may enable system 100 to use detected relationships to discover new correlations between known biomarkers, advisory labels, and/or advisory labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular advisory labels and/or suitable advisory labels. Use of unsupervised learning may greatly enhance the accuracy and detail with which system may detect advisory labels and/or advisory labels.

With continued reference to FIG. 14, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of advisory label, and/or a group of people having a shared value and/or category of advisory label; as illustrative examples, cohort could include all people having a certain level or range of levels of blood triglycerides, all people diagnosed with anxiety, all people who regularly practice a religion, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 14, first label learner 164 may alternatively or additionally be designed and configured to generate at least an advisory output 1408 by executing a lazy learning process as a function of the first training set 128 and/or at least a biological extraction; lazy learning processes may be performed by a lazy learning module 1412 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at an advisory label associated with a user physiological test sample, using first training set 128. As a non-limiting example, an initial heuristic may include a ranking of advisory labels according to relation to a test type of at least a physiological test sample, one or more categories of physiological data identified in test type of at least a physiological test sample, and/or one or more values detected in at least a physiological test sample; ranking may include, without limitation, ranking according to significance scores of associations between elements of physiological data and advisory labels, for instance as calculated as described above. Heuristic may include selecting some number of highest-ranking associations and/or advisory labels. First label learner 164 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate advisory outputs 1408 as described in this disclosure, including without limitation lazy learning applications of machine-learning algorithms as described in further detail below.

Figure 15:
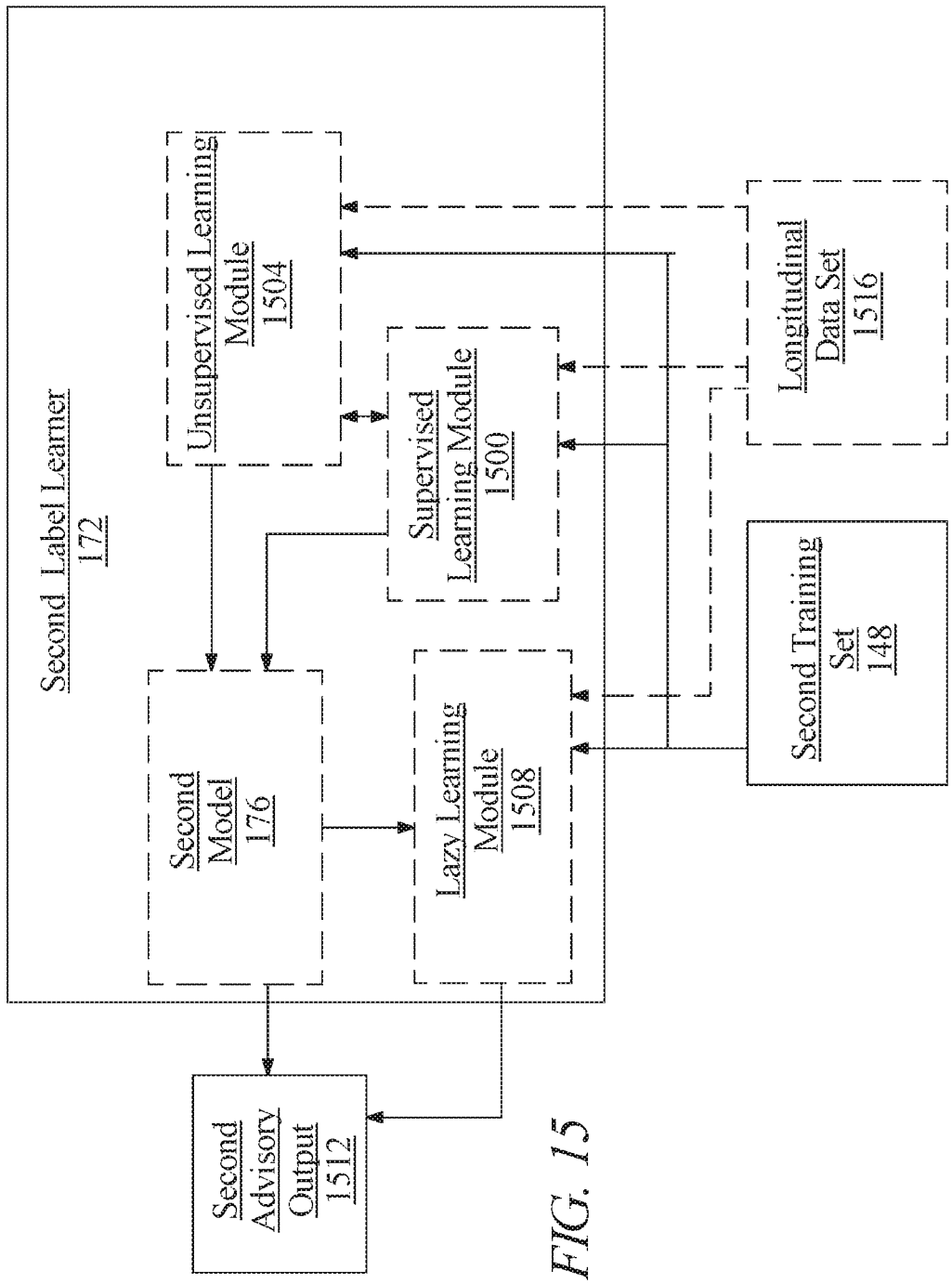
FIG. 15 is a block diagram illustrating an exemplary embodiment of a second label learner and associated system elements.

Referring now to FIG. 15, an exemplary embodiment of second label learner 172 is illustrated. Second label learner 172 may be configured to perform one or more supervised learning processes, as described above; supervised learning processes may be performed by a supervised learning module 1500 executing on at least a server 104 and/or on another computing device in communication with at least a server 104, which may include any hardware or software module. For instance, a supervised learning algorithm may use user inputs as inputs, advisory labels as outputs, and a scoring function representing a desired form of relationship to be detected between advisory labels and user input labels; scoring function may, for instance, seek to maximize the probability that a given advisory label and/or combination of advisory labels is associated with a given user input label and/or combination of user input labels to minimize the probability that a given advisory label and/or combination of advisory labels is not associated with a given user input label and/or combination of user input labels. In an embodiment, one or more supervised machine-learning algorithms may be restricted to a particular domain; for instance, a supervised machine-learning process may be performed with respect to a given set of parameters and/or categories of advisory labels that have been suspected to be related to a given set of user input labels, for instance because the user inputs corresponding to the set of user input labels are hypothesized or suspected to have an effect on the advisory labels, and/or are specified as linked to a particular user input label. As a non-limiting example, a particular set of user input labels corresponding to a set of conditions that may be alleviated by meditation, and a supervised machine-learning process may be performed to relate those user input labels to advisory labels associated with various advisors that may be qualified to provide instruction to users with those user inputs including for example, meditation teachers, spiritual coaches, and spiritual advisors and the like.

With continued reference to FIG. 15, second label learner 172 may perform one or more unsupervised machine-learning processes as described above; unsupervised processes may be performed by an unsupervised learning module 1504 executing on at least a server 104 and/or on another computing device in communication with at least a server 104, which may include any hardware or software module. For instance, and without limitation, second label learner 172 and/or at least a server 104 may perform an unsupervised machine learning process on second training set 148, which may cluster data of second training set 148 according to detected relationships between elements of the second training set 148, including without limitation correlations of user input labels to each other and correlations of advisory labels to each other; such relations may then be combined with supervised machine learning results to add new criteria for second label learner 172 to apply in relating user input labels to advisory labels. As a non-limiting, illustrative example, an unsupervised process may determine that a first user input label correlates closely with a second user input label, where the first user input label has been linked via supervised learning processes to a given advisory label, but the second user input label has not; for instance, the second user input label may not have been defined as an input for the supervised learning process, or may pertain to a domain outside of a domain limitation for the supervised learning process. Continuing the example, a close correlation between first user input label and second user input label may indicate that the second user input label is also a good match for the advisory label; second user input label may be included in a new supervised process to derive a relationship or may be used as a synonym or proxy for the first user input label by second label learner 172. Unsupervised processes performed by second label learner 172 may be subjected to any domain limitations suitable for unsupervised processes performed by first label learner 164 as described above.

Continuing to view FIG. 15, second label learner 172 may be configured to perform a lazy learning process as a function of the second training set 148 and the at least a constitutional output to produce the at least an advisor output; a lazy learning process may include any lazy learning process as described above regarding first label learner 164. Lazy learning processes may be performed by a lazy learning module 1508 executing on at least a server 104 and/or on another computing device in communication with at least a server 104, which may include any hardware or software module. Second Advisory output 1512 may be provided to a user output device as described in further detail below.

In an embodiment, and still referring to FIG. 15, second label learner 172 may generate a plurality of advisory process labels having different implications for a particular person. For instance, where an advisory output is related to a user with anxiety options may be generated including meditation, prayer, and tai chi. In such a situation, second label learner 172 and/or at least a server 104 may perform additional processes to resolve ambiguity. Processes may include presenting multiple possible results to a user, informing the medical practitioner of various options that may be available, and/or providing the user with several options to pick from. Alternatively or additionally, processes may include additional machine learning steps. For instance, second label learner 172 may perform one or more lazy learning processes using a more comprehensive set of user inputs to identify a more probably correct result of the multiple results. Results may be presented and/or retained with rankings, for instance to advise a user and/or medical professional of the relative probabilities of various advisory labels being correct or ideal choices for a given user; alternatively or additionally, advisory labels associated with a probability of success or suitability below a given threshold and/or advisory labels contradicting results of the additional process, may be eliminated. As a non-limiting example, an additional process may reveal that a user has practiced tai chi before and would prefer to start with tai chi to manage user's anxiety before trying meditation or prayer.

Continuing to refer to FIG. 15, second label learner 172 may be designed and configured to generate further training data and/or to generate outputs using longitudinal data 1516. As used herein, longitudinal data 1516 may include a temporally ordered series of data concerning the same person, or the same cohort of persons; for instance, longitudinal data 1516 may describe a series of spiritual practices a user has embarked upon over the last year. Longitudinal data 1516 may be related to one or more spiritual practices recommended by an informed advisor. Second label learner 172 may track one or more elements of user data and fit, for instance, a linear, polynomial, and/or splined function to data points; linear, polynomial, or other regression across larger sets of longitudinal data, using, for instance, any regression process as described above, may be used to determine a best-fit graph or function for the effect of a given process over time on a user data parameter. Functions may be compared to each other to rank processes; for instance, a process associated with a steeper slope in curve representing improvement in a user data element, and/or a shallower slope in a curve representing a slower decline, may be ranked higher than a process associated with a less steep slope for an improvement curve or a steeper slope for a curve marking a decline. Processes associated with a curve and/or terminal data point representing a value that does not associate with a previously detected advisory label may be ranked higher than one that is not so associated. Information obtained by analysis of longitudinal data 1516 may be added to second training set 148.

Figure 16:
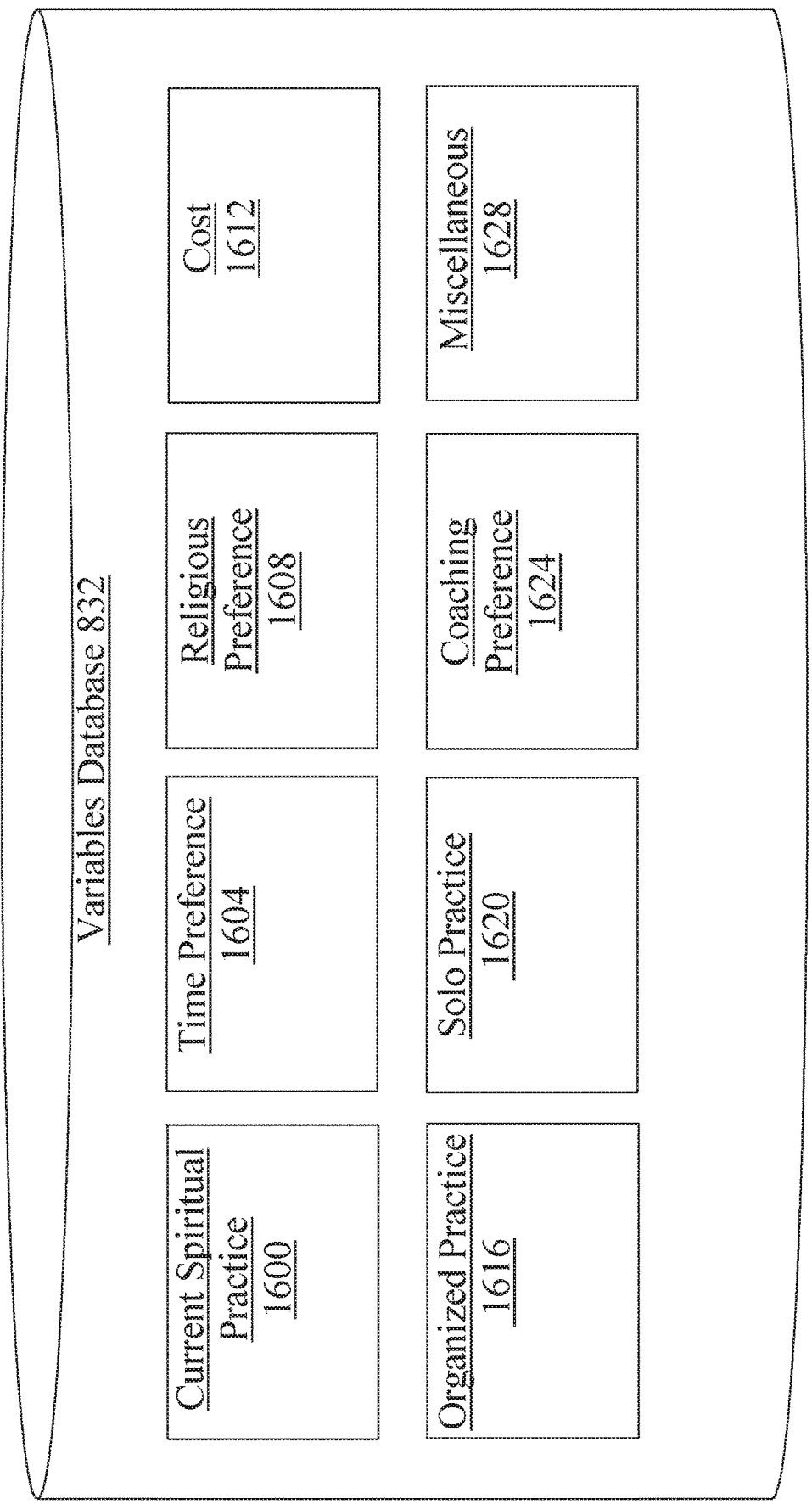
FIG. 16 is a block diagram illustrating an exemplary embodiment of a variables database.

Referring now to FIG. 16, an exemplary embodiment of variables database 832 is illustrated. Variables database 832 may be implemented as any database and/or datastore suitable for use as biological extraction database 300 as described above. Variables database 832 may be consulted and/or utilized by advisory module 116, first label learner 164, and/or second label learner 172 when generating a loss function of user-specific variables and minimizing the loss function as described above in more detail in reference to FIG. 1. One or more database tables in variables database 832 may include, without limitation, a current spiritual practice table 1600; current spiritual practice table 1600 may contain information pertaining to any current spiritual practice user may current practice and/or engage in. For example and without limitation, current spiritual practice table 1600 may contain information pertaining to current tai chi practice user engages in or bible study class user attends each week. One or more database tables in variables database 832 may include without limitation, a time preference table 1604; time preference table 1604 may contain information pertaining to time user dedicates or is willing to dedicate to a spiritual practice each week. For example and without limitation, time preference table 1604 may include information describing a user's ability to devote twenty minutes each day to a spiritual practice or one hour each Sunday to a spiritual practice. One or more database tables in variables database 832 may include without limitation, a religious preference table 1608; religious preference table 1608 may include information pertaining to a user's preference for a particular sect or form of religion. For example and without limitation, a user may prefer to practice Christianity or even a specific form of Christianity such as Protestantism or Catholicism. One or more database tables in variables database 832 may include without limitation, cost table 1612; cost table 1612 may include information relating to user cost to devote a certain amount of money to a particular religious or spiritual practice. For example and without limitation, cost table 1612 may include information describing a user's preference to pay a certain amount of money for a yoga class or donate a certain amount of money to a church offering basket each week. One or more database tables in variables database 832 may include without limitation, organized practice table 1612; organized practice table 1612 may include information relating to a user's desire to engage in an organized spiritual practice and engage in a spiritual practice with other participants. For example and without limitation, organized practice table 1616 may include information describing a user's preference to participate as a member of a church or synagogue, or to participate in a group meditation session or group yoga session. One or more database tables in variables database 832 may include without limitation, solo practice table 1620; solo practice table 1620 may include information relating to a user's desire to engage in an individual spiritual practice and engage in a spiritual practice without other participants. For example and without limitation, solo practice table 1620 may contain information describing a user's preference to meditate alone or practice yoga by one's self and not in a group setting. One or more database tables in variables database 832 may include without limitation, coaching preference table 1624; coaching preference table 1624 may include information describing a user's preference to receive assistance with spirituality and/or life issues with or without the assistance of a coach. For example and without limitation, coaching preference table 1624 may include information describing user's preference for a coach to aid user with developing a spiritual practice. One or more database tables in variables database 832 may include without limitation, miscellaneous table 1628; miscellaneous table 1628 may include other variables that may be utilized but have not been discussed above.

Figure 17:
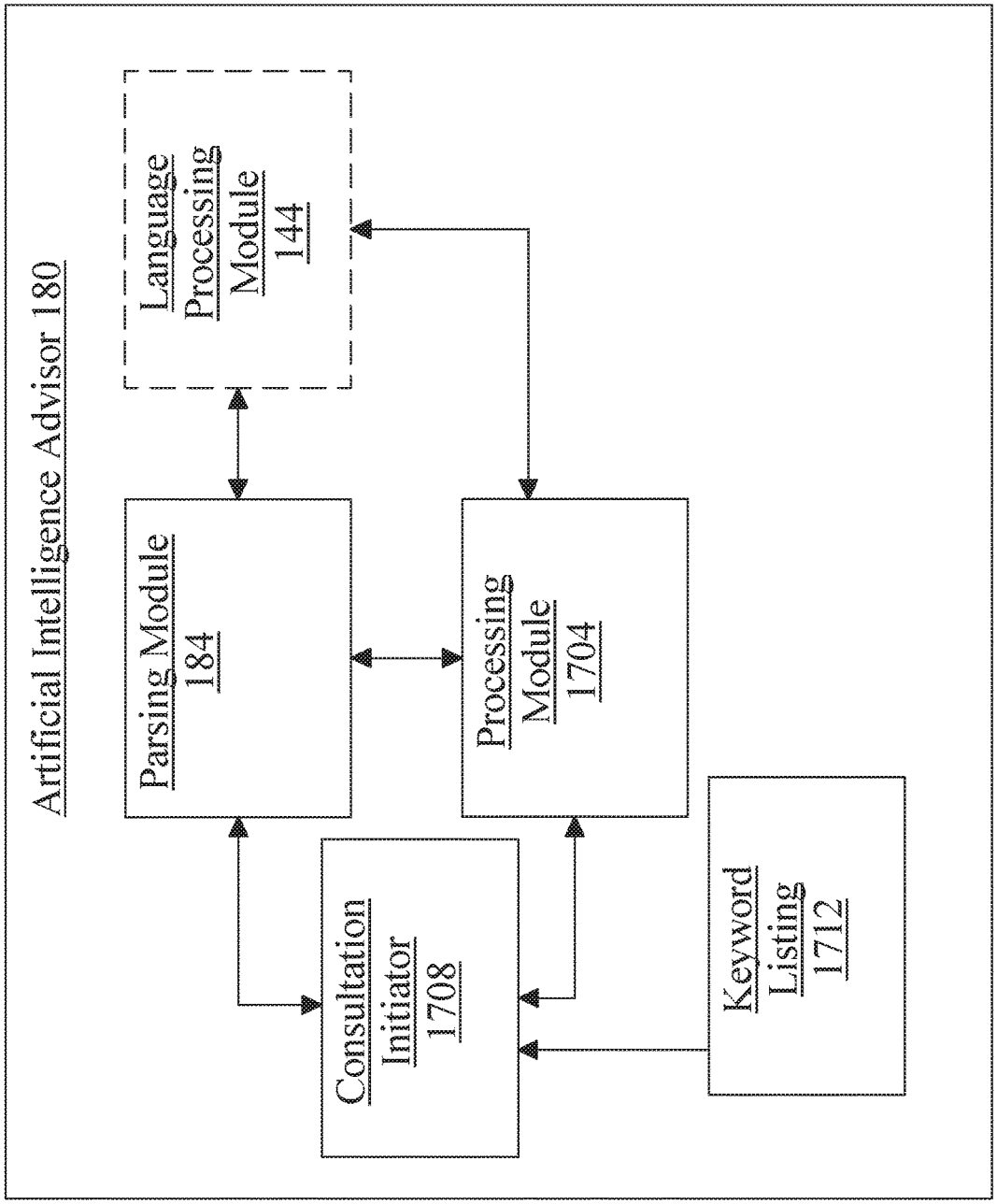
FIG. 17 is a block diagram illustrating an exemplary embodiment of an artificial intelligence advisor and associated system elements.

Referring now to FIG. 17, an exemplary embodiment of an artificial intelligence advisor 180 is illustrated. In an embodiment, artificial intelligence advisor includes a parsing module 184 configured to generate at least a query using the at least a user input. At least a query, as used in this disclosure, is at least a datum used to retrieve text that will be incorporated in at least a textual output, where retrieval may be effected by inputting the at least a query into a data structure, database, and/or model, and receiving a corresponding output as a result, for example as set forth in further detail below. Parsing module 184 may generate at least a query by extracting one or more words or phrases from the input, and/or analyzing one or more words or phrases; extraction and/or analysis may include tokenization, for instance as described above in relation to language processing module 144. In an embodiment, parsing module 184 may utilize, incorporate, or be a language processing module 144 as described above. Language processing module 144 may be configured to map at least a user input to at least a query, using any process as described above for a language processing module 144. Extraction and/or analysis may further involve polarity classification, in which parsing module 184 may determine, for instance, whether a phrase or sentence is a negation of the semantic content thereof, or a positive recitation of the semantic content; as a non-limiting example, polarity classification may enable parsing module 184 to determine that "I believe in God" has a divergent meaning, or the opposite meaning, of the phrase "I don't' believe in God." Polarity classification may be performed, without limitation, by consultation of a database of words that negate sentences, and/or geometrically within a vector space, where a negation of a given phrase may be distant from the non-negated version of the same phrase according to norms such as cosine similarity.

Still referring to FIG. 17, parsing module 184 may be configured to normalize one or more words or phrases of user input, where normalization signifies a process whereby one or more words or phrases are modified to match corrected or canonical forms; for instance, misspelled words may be modified to correctly spelled versions, words with alternative spellings may be converted to spellings adhering to a selected standard, such as American or British spellings, capitalizations and apostrophes may be corrected, and the like; this may be performed by reference to one or more "dictionary" data structures listing correct spellings and/or common misspellings and/or alternative spellings, or the like. Parsing module 184 may perform algorithms for named entity recognition. Named entity recognition may include a process whereby names of users, names of informed advisors such as doctors, medical professionals, spiritual advisors, coaches, trainers, family members or the like, addresses, place names, entity names, or the like are identified; this may be performed, without limitation, by searching for words and/or phrases in user database. For instance, parsing module 184 may identify at least a phrase, which may include one or more words, map the at least a phrase to at least a query element, and then assemble a query using the at least a query element. Mapping at least a phrase to at least a query element may be performed using any language processing technique described in this disclosure, including vector similarity techniques.

With continued reference to FIG. 17, parsing module 184 may extract and/or analyze one or more words or phrases by performing dependency parsing processes; a dependency parsing process may be a process whereby parsing module 184 and/or a language processing module 144 communicating with and/or incorporated in parsing module 184 recognizes a sentence or clause and assigns a syntactic structure to the sentence or clause. Dependency parsing may include searching for or detecting syntactic elements such as subjects, objects, predicates or other verb-based syntactic structures, common phrases, nouns, adverbs, adjectives, and the like; such detected syntactic structures may be related to each other using a data structure and/or arrangement of data corresponding, as a non-limiting example, to a sentence diagram, parse tree, or similar representation of syntactic structure. Parsing module 184 may be configured, as part of dependency parsing, to generate a plurality of representations of syntactic structure, such as a plurality of parse trees, and select a correct representation from the plurality; this may be performed, without limitation, by use of syntactic disambiguation parsing algorithms such as, without limitation, Cocke-Kasami-Younger (CKY), Barley algorithm or Chart parsing algorithms. Disambiguation may alternatively or additionally be performed by comparison to representations a syntactic structures of similar phrases as detected using vector similarity, by reference to machine-learning algorithms and/or modules such as without limitation a user communication learner as described below, or the like.

Still referring to FIG. 17, parsing module 184 may combine separately analyzed elements from at least a user input together to form a single query; elements may include words, phrases, sentences, or the like, as described above. For instance, two elements may have closely related meanings as detected using vector similarity or the like; as a further non-limiting example, a first element may be determined to modify and/or have a syntactic dependency on a second element, using dependency analysis or similar processes as described above. Combination into a query may include, without limitation, concatenation. Alternatively or additionally, parsing module 184 may detect two or more queries in a single user input of at least a user input; for instance, parsing module 184 may extract a conversational query and an informational query from a single user input. An informational query, as used in this disclosure, is a query used to retrieve one or more elements of factual information; one or more elements may include, without limitation, any data suitable for use as an advisory label, a user input label, and/or biological extraction data as described above. One or more elements may include an identity of a category of an advisory label, user input label, biological extraction datum, informed advisor, spiritual practice, religious preference, current religious beliefs, or the like. One or more elements may include an identity of any factual element, including an identity of a place, person, informed advisor, user, entity, or the like. A conversational query, as used herein, is a query used to generate a textual response and/or response form, such as an overall sentence structure, templates, words, and/or phrases such as those usable for entries in narrative language database as described above, for inclusion of information returned in response to an informational query, for a response to a question, comment, phrase, or sentence that is not in itself a request for information, and/or for a request for clarification and/or more information as described in further detail below. A conversational query may include one or more pattern-matching elements, such as regular expressions, "wildcards," or the like.

With continued reference to FIG. 17, parsing module 184 may be configured to convert at least a query into at least a canonical or standard form of query; for instance, and without limitation, once a query has been detected, parsing module 184 may convert it to a highly closely related query based on vector similarity, where the highly closely related query is labeled as a standard form or canonical query. In an embodiment, converting to a standard form query may enable more efficient processing of queries as described below, as a reduced space of potential queries may be used to retrieve conversational and/or informational responses.

Continuing to refer to FIG. 17, artificial intelligence advisor may include a processing module 1704 configured to generate the at least a textual output as a function of the at least a query. Processing module 1704 is described in more detail below. Artificial intelligence advisor may include a consultation initiator 1708 configured to detect a consultation event in a user textual conversation and initiate a consultation with an informed advisor as a function of the consultation event. A consultation event, as used herein, is a situation where an informed advisor such as a spiritual informed advisor as described above, is needed to address a user's situation or concerns, such as when a user should be consulting with a doctor regarding an apparent medical emergency or new condition, or with an advisor who can lend emotional support when particularly distraught. Detection may be performed, without limitation, by matching an input and/or set of inputs to an output that constitutes an action of initiating a consultation; such a pairing of an input and/or input set may be learned using a machine learning process, for instance via general learner and/or user specific learner. In the latter case, information concerning a particular user's physical or emotional needs or condition may be a part of the training set used to generate the input/input set to consultation event pairing; for instance, a user with a desire to develop a religious practice may trigger consultation events upon any inputs describing failure to attend a religious meeting, disbelief in a higher power or the like. Initiation of consultation may include transmitting a message to an advisor client device 124 associated with an appropriate informed advisor, such as without limitation transmission of information regarding a potential need for a spiritual intervention by a spiritual informed advisor. Initiation of consultation may alternatively or additionally include providing an output to the user informing the user that a consultation with an informed advisor, who may be specified by name or role, is advisable. Consultation initiator 1708 may analyze consultation inputs, defined as any element of conversation input to, output from, and/or processed by artificial intelligence advisor 180 and/or any component or module thereof, including without limitation user inputs, words or phrases extracted from user inputs conversational queries, informational queries, conversational outputs, informational outputs, and/or textual outputs. In an embodiment, consultation initiator may compare consultation inputs to keywords in a keyword listing 1712, where keywords may include any word or phrase as described in this disclosure, and comparison may include any form of comparison as described in this disclosure. Keyword listing 1712 may include any data structure and/or database suitable for storage, retrieval, and/or comparison of textual data. Keyword listing 1712 may be populated using expert submissions of keywords associated with consultation events; expert submissions may be collected and inserted to keyword listing 1712 using any methods, components, and/or modules as described above regarding expert knowledge database 304 and/or related elements. Keyword listing 1712 may include user-specific keywords; for instance, keyword listing may combine keywords with advisory labels and/or user identifiers, such that a keyword encountered for a particular user, and/or for a user having a particular condition and/or spiritual journey, may generate a consultation event, while absent such matching data the keyword may not generate a consultation event.

Figure 18:
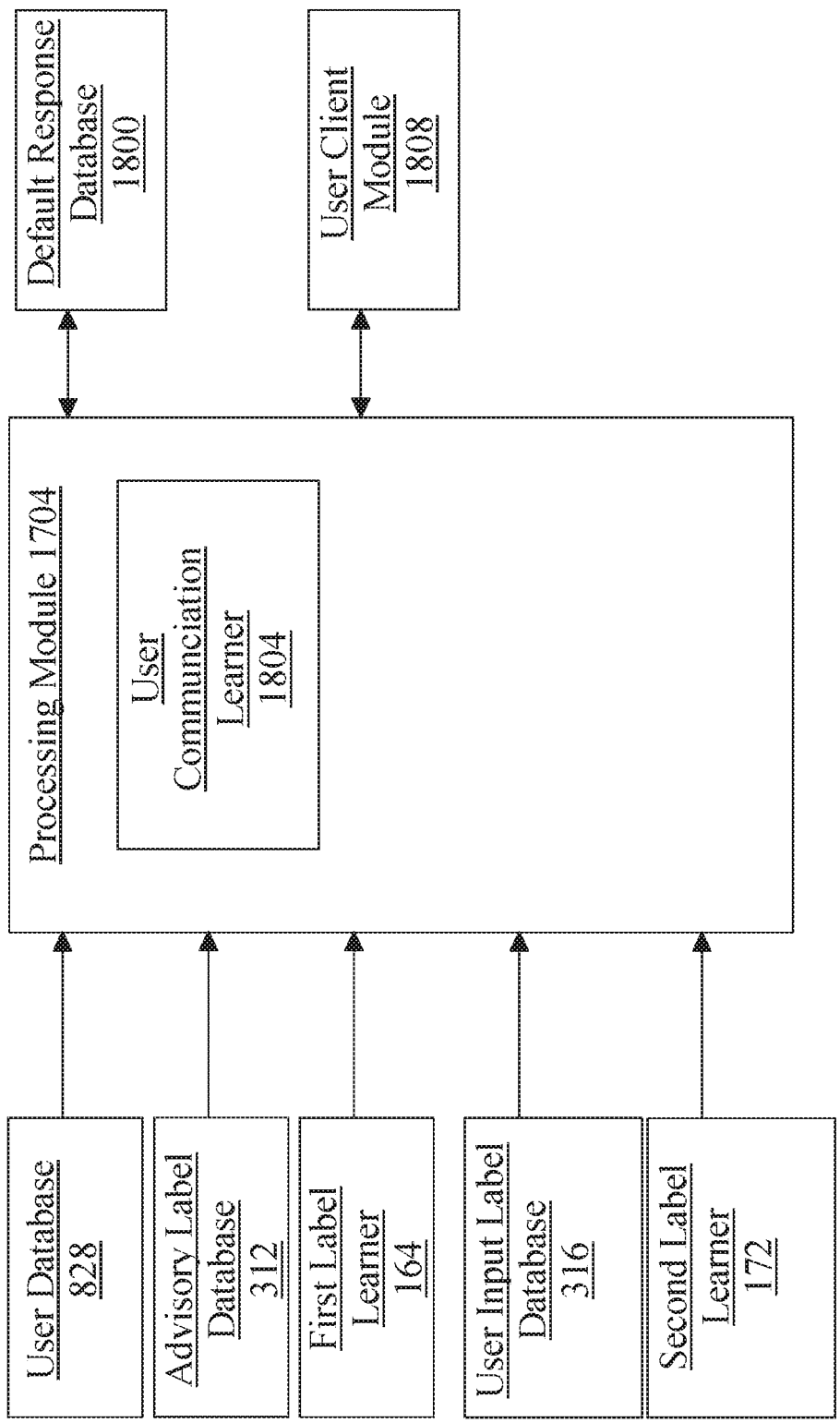
FIG. 18 is a block diagram illustrating an exemplary embodiment of a processing module.

Referring now to FIG. 18, an exemplary embodiment of a processing module 1704 is illustrated. In an embodiment, processing module 1704 may be configured to determine that the at least a query includes a conversational language query and generate a conversational response using the conversational language query. In an embodiment, and as a non-limiting example, processing module 1704 may be configured to generate the conversational response by retrieving at least a datum from a conversational resource, which for purposes of this disclosure is a data structure, database, data store, and/or data module that returns data usable to generate a conversational response when queried using a conversational language query. A conversational resource may include a default response database 1800; for instance, processing module 1704 may be configured to retrieve at least a datum from a default response database 1800 using a conversational language query, and generate the conversational response using the at least a datum. Default response database 1800 may link inputs to outputs according to initial relationships entered by users, including without limitation experts as described above, and/or as created by a previous instance or version of general learner and/or user-specific learner. Default response database 1800 may periodically be updated with information from newly generated instances machine-learning models and/or modules, or other components of artificial intelligence advisor 180. Inputs received by artificial intelligence advisor 180 may be mapped to canonical and/or representative inputs by synonym detection as performed, for instance, by a language processing module 144; language processing module 144 may be involved in textual analysis and/or generation of text at any other point in machine-learning and/or communication processes undergone by artificial intelligence advisor 180.

With continued reference to FIG. 18, processing module 1704 and/or a conversational resource may include a user communication learner 1804 configured to generate the at least a conversational response using the conversational language query. User communication learner 1804 is described in more detail below in reference to FIG. 20.

With continued reference to FIG. 18, processing module 1704 may be further configured to determine that the at least a query includes an informational query and generate an informational response using the informational query. This may be performed, as a non-limiting example, by user communication learner 1804, which use corpus to relate queries to labels identifying conversational queries or informational queries. Alternatively or additionally, parsing module 184 may provide processing module 1704 information indicating that a query is a conversational query and/or an informational query. Generation of an informational response may be accomplished by retrieving at least a datum from an informational resource, which for purposes of this disclosure is a data structure, database, data store, and/or data module that returns data usable to generate an informational response when queried using an informational query. For instance, and without limitation, processing module 1704 may be configured to retrieve at least a datum from a user input datum using the informational query and generate the informational response using the at least a datum. As a non-limiting example, processing module 1704 may compare informational query to one or more textual elements in user input datum; comparison may be performed using any form of textual comparison and/or matching described above as performed by parsing module 184, processing module 1704, and/or language processing module 144.

Still referring to FIG. 18, as a non-limiting example, where at least a user input describes and/or inquiries concerning a spiritual exercise sequence such as a yoga sequence, tai chi, qui gong that is best for arthritis, processing module 1704 may compare textual description of the spiritual exercise to one or more textual descriptions of sequence in an expert database such as expert knowledge database 304 and use the one or more textual descriptions to generate an informational response. As another non-limiting example, where at least a user input describes or inquiries concerning a particular religious practice, processing module 1704 may compare textual description of the religious practice to one or more textual descriptions contained within expert knowledge database 304 to generate an informational response; one or more textual descriptions may include a question or inquiry as to how to practice a particular religion or beliefs, sacraments, holy days and values shared by a particular religion.

Still referring to FIG. 18, generating the informational response using at least a datum may include generating the informational response and/or a portion thereof directly from the at least a datum; for instance, processing module 1704 may convert the at least a datum into narrative language, images, and/or videos using any element of advisory module 116 as described above, and may incorporate the narrative language, images, and/or videos into the informational response. Alternatively or additionally, generating the informational response using at least a datum may include modifying the informational query using the at least a datum and performing any step described herein for generating an informational response from an informational query using the modified informational query.

With continued reference to FIG. 18, processing module 1704 may be configured to retrieve at least a datum from a user database using the informational query and generate the informational response using the at least a datum. For instance, and without limitation, user database may list one or more user preferences, religious beliefs, current religious practices and the like. As a non-limiting example, processing module 1704 may retrieve a current spiritual practice of user from user database 828. As a further non-limiting example, processing module 1704 may retrieve one or more user preferences concerning time user wishes to devote to a spiritual practice. Either retrieval may be performed using a modified informational query: for instance, user may submit an entry inquiring about a particular religious practice, how to perform tai chi, how to practice Reiki and the like; processing module 1704 may retrieve such details and check them against user preferences contained within user database 828. Informational response may further recommend an informed advisor, category of informed advisor, list of advisors, and/or ameliorative label based on the at least a user input.

Continuing to refer to FIG. 18, processing module 1704 may be further configured to retrieve an advisory output from advisory label database 312 using the informational query and generate the informational response using the advisory output. Alternatively or additionally, processing module 1704 may be configured to input the informational query to a first label learner 164 operating on the at least a server, wherein the first label learner 164 is designed and configured to generate at least an advisory output as a function of a training set correlating diagnostic output data to advisory labels and the informational query, receive, from the first label learner 164, the at least a an advisory output, and generate the informational response using the at least an advisory output. For instance, and without limitation, where user input describes one or more symptoms, processing module 1704 may submit an informational query including the one or more symptoms to advisory label database and/or first label learner 164; informational query may be converted to a form of biological extraction data using any processes or modules described above for arrangement of biological extraction data and/or physiological state data for use in advisory label database 312, first training set, and/or as an input to first label learner 164. The above is described for exemplary purposes only; persons skilled in the art, upon reviewing the entirety of this disclosure, will be aware of various additional examples as consistent with this disclosure.

Still referring to FIG. 18, generating the informational response using one or more advisory outputs may include generating the informational response and/or a portion thereof directly from the at least a datum; for instance, processing module 1704 may convert the one or more advisory outputs into narrative language, images, and/or videos using any element of advisory module 116 as described above, and may incorporate the narrative language, images, and/or videos into the informational response. Alternatively or additionally, generating the informational response using one or more advisory outputs may include modifying the informational query using the one or more advisory outputs and performing any step described herein for generating an informational response from an informational query using the modified informational query.

With continued reference to FIG. 18, processing module 1704 may be configured to retrieve at least a user input from a user database 828 using an informational query and generate the informational response using the at least a second advisory label. Alternatively or additionally, processing module 1704 may be configured to input an informational query to an second label learner 172 operating on the at least a server, wherein the second label learner 172 is designed and configured to generate at least a second advisory output as a function of a training set correlating user input labels to advisory labels and the informational query, receive, from the second label learner 172, the at least a second advisory output, and generate the informational response using the at least a second advisory output. For instance, and without limitation, where a user input includes an inquiry about a particular meditation sequence, processing module 1704 may retrieve information concerning such the meditation sequence from a second advisory label. The above is described for exemplary purposes only; persons skilled in the art, upon reviewing the entirety of this disclosure, will be aware of various additional examples as consistent with this disclosure. Informational response may further recommend an informed advisor, category of informed advisor, list of advisors, and/or user input label based on the at least a user input.

Still referring to FIG. 18, generating the informational response using at least a second advisory label may include generating the informational response and/or a portion thereof directly from the at least a second advisory output; for instance, processing module 1704 may convert the at least a second advisory output into narrative language, images, and/or videos using any element of advisory module 116 as described above, and may incorporate the narrative language, images, and/or videos into the informational response. Alternatively or additionally, generating the informational response using the at least a second advisory output may include modifying the informational query using the at least a second advisory output and performing any step described herein for generating an informational response from an informational query using the modified informational query.

'With continued reference to FIG. 18, processing module 1704 may be configured to generate the at least an informational response by generating a plurality of informational responses using a first informational resource, retrieving at least an additional datum from at least a second informational resource, and selecting an informational response using the at least an additional datum. This may include, without limitation, elimination from the plurality of informational responses of one or more informational responses that are inconsistent with the at least an additional datum. For instance, and without limitation, where at least a user input, diagnostic output, second label learner, and/or user input label database 316 database may be used to generate a list of second advisory labels that user may engage in user's spiritual request, and/or one or more categories of informed advisors who may be able to assist in user's spiritual journey, and/or a list of such informed advisors; second resource may include, for instance, user database, 828 which may eliminate from any such list one or more elements that contradict one or more user preferences. Continuing the example, and without limitation, advisory labels that contradict user beliefs, or current spiritual practices or the like as listed in user database 828 may be eliminated, informed advisors that live too far away from the user according to user preferences listed in user database 828 may be eliminated, or the like; persons skilled in the art, upon reviewing the entirety of this disclosure, will be aware of the enormous variety of user preferences, and other factors that may be used to eliminate one or more informational responses of a plurality of informational responses. Alternatively or additionally, selection of an informational response may be performed positively, for instance by matching the informational response to the at least a second datum. For instance, and without limitation, user database 828 may list one or more user preferences, and processing module 1704 may select an informational response matching the one or more user preferences. Matching, whether performed negatively or positively, may be performed via any process described in this disclosure for matching one textual element to another, including string comparison, exact matching, detection of vector similarity, such as without limitation cosine similarity, above a threshold amount, or the like.

Still referring to FIG. 18, second information resource may include user client module 1808; in an embodiment, processing module 1704 may generate a user clarification question, provide the user clarification question to the user client module, and receive a user response from a user client device via the user client module. Generating the clarification question may be performed using any suitable process for generating a conversational response as described above and/or any process for generating a combined conversational and informational response as set forth in further detail below. For instance, and as a non-limiting illustration, default response database 1800 may contain a response template instructing artificial intelligence advisor, given variables stored in "option_1" and "option_2," to concatenate string and variable values in the following form: "Did you mean"+option_1+"or"+option_2+"?" so as to receive a user clarification. Similar templates could be constructed asking a user if her or she prefers an option stored in a first variable to an option stored in a second variable, or the like. Generation of clarification question may include identifying a difference between a first informational response and a second informational response and forming a question for a user asking about the difference. For instance, if a first informational response provides a first advisory label describing a disease state associated with a yoga practice, and the second informational response provides a second advisory label describing a disease state with a meditation sequence, a clarification question may ask whether the user has a preference for yoga or meditation; this approach for generating a request may be accomplished, without limitation, by dividing text describing each informational response, such as text obtained from a narrative language database, into tokens such as words or phrases, and using a similarity test such as vector similarity to detect one or more dissimilar tokens between two or more informational responses; the one or more dissimilar tokes may then be used to generate a conversational response as described above.

Continuing to refer to FIG. 18, processing module 1704 may be configured to convert an informational response into at least a portion of a textual output; this may be performed using any process and/or processes as described above for converting diagnostic outputs to narrative language, images, videos, and/or combinations thereof in plan generator or the like. For instance, and without limitation, processing module 1704 may retrieve one or more strings and/or templates from narrative language database to generate a narrative language form of or analog to an informational output. A narrative language unit may perform conversion of informational output into at least a portion of a textual output.

Still referring to FIG. 18, in an embodiment, processing module 1704 may be configured to determine that the at least a query includes a conversation language query and an informational query, generate a conversational response using the conversational language query; generate an informational response using the informational query, and combine the conversational response and the informational response. Determination may be performed as described above. In an embodiment, processing module 1704 may generate each of conversational response and informational response as described above. Conversational response and informational response may be combined in any suitable manner. For instance, where conversational response and informational response are two separate sentences, clauses, or sequentially arrangeable phrases, combination may include concatenation; as a non-limiting illustration, conversational response may include an initial sentence such as "Hi. Thank you for your question." and a final sentence such as "Do you have any more questions?" and informational response may include a statement such as "your bible reading tonight includes readings from the Old Testament," which processing module 1704 may combine into "Hi. Thank you for your question. Your bible reading tonight includes readings from the Old Testament. Do you have any more questions?" As a further non-limiting example, conversational response may include a template, as described above, into which an informational response may be inserted. As a non-limiting illustration, conversational response may be "Your bible readings tonight include <INFO>." and informational response, which processing module may use to replace "<INFO>" may be "Old Testament"; replacement may be performed as described above. Templates may be nested and/or concatenated; for instance a variable or label calling for insertion of a textual value into a template may itself refer to an additional template to be inserted at that point. Persons skilled in the art, upon reviewing the entirety of this disclosure, will be aware of various ways in which conversational responses and informational responses may be combined to produce textual output.

Figure 19:
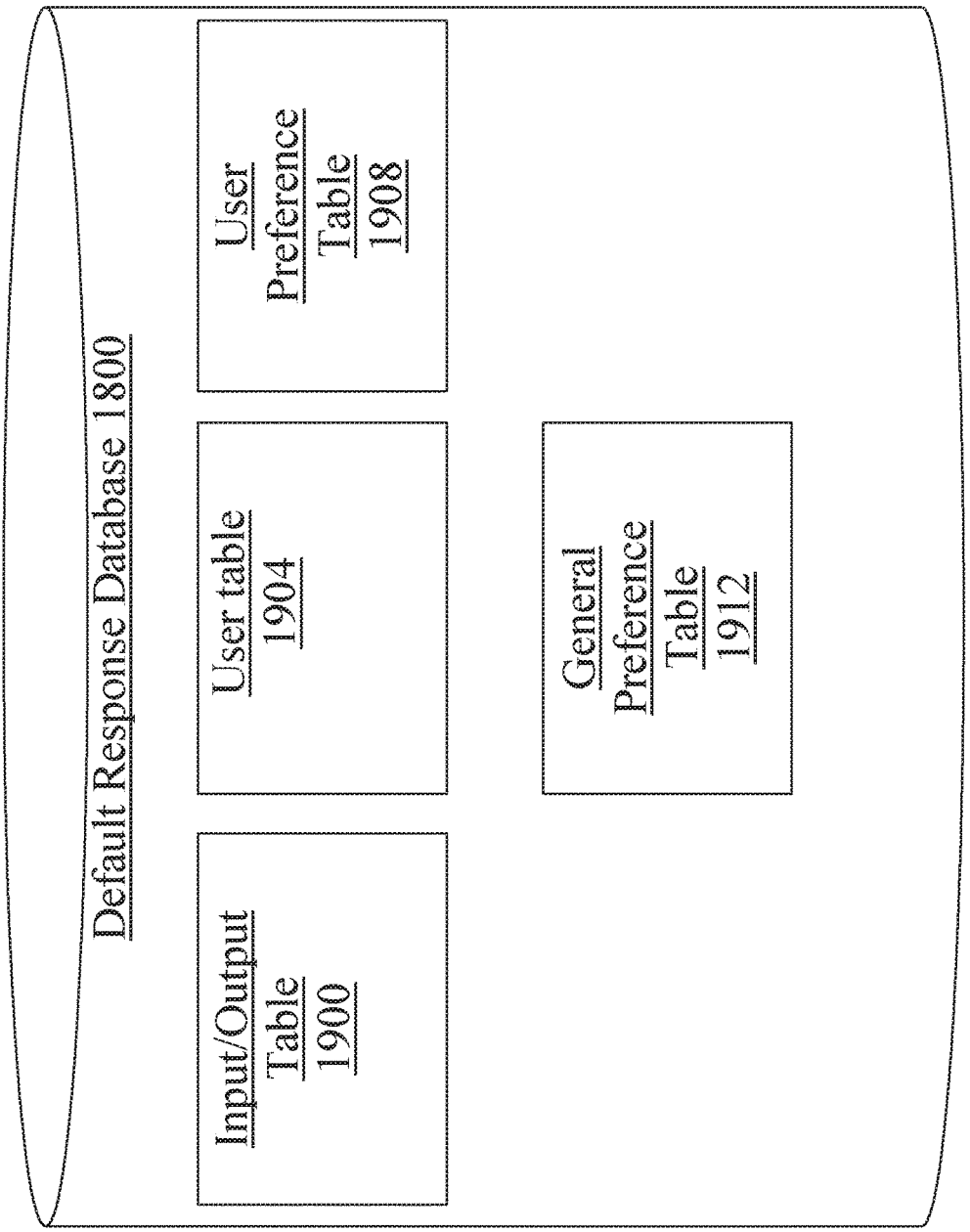
FIG. 19 is a block diagram illustrating an exemplary embodiment of a default response database.

Referring now to FIG. 19, an exemplary embodiment of a default response database 1800 is illustrated. Default response database 1800 may be implemented as any database and/or datastore suitable for use as biological extraction database 300 as described above. One or more database tables in default response database 1800 may include, without limitation, an input/output table 1900, which may link default inputs to default outputs. Default response database 1800 may include a user table 1904, which may, for instance, map users and/or a user client device 108 to particular user-specific learners and/or past conversations. Default response database 1800 may include a user preference table 1908 listing preferred modes of address, turns of phrase, or other user-specific communication preferences. Default response database 1800 may include a general preference table 1912, which may track, for instance, output-input pairings associated with greater degrees of user satisfaction. Where multiple records and/or responses may be retrieved from default response database 1800, processing module 1704 may relate such records hierarchically, for instance using hierarchical pattern-matching programs.

Figure 20:
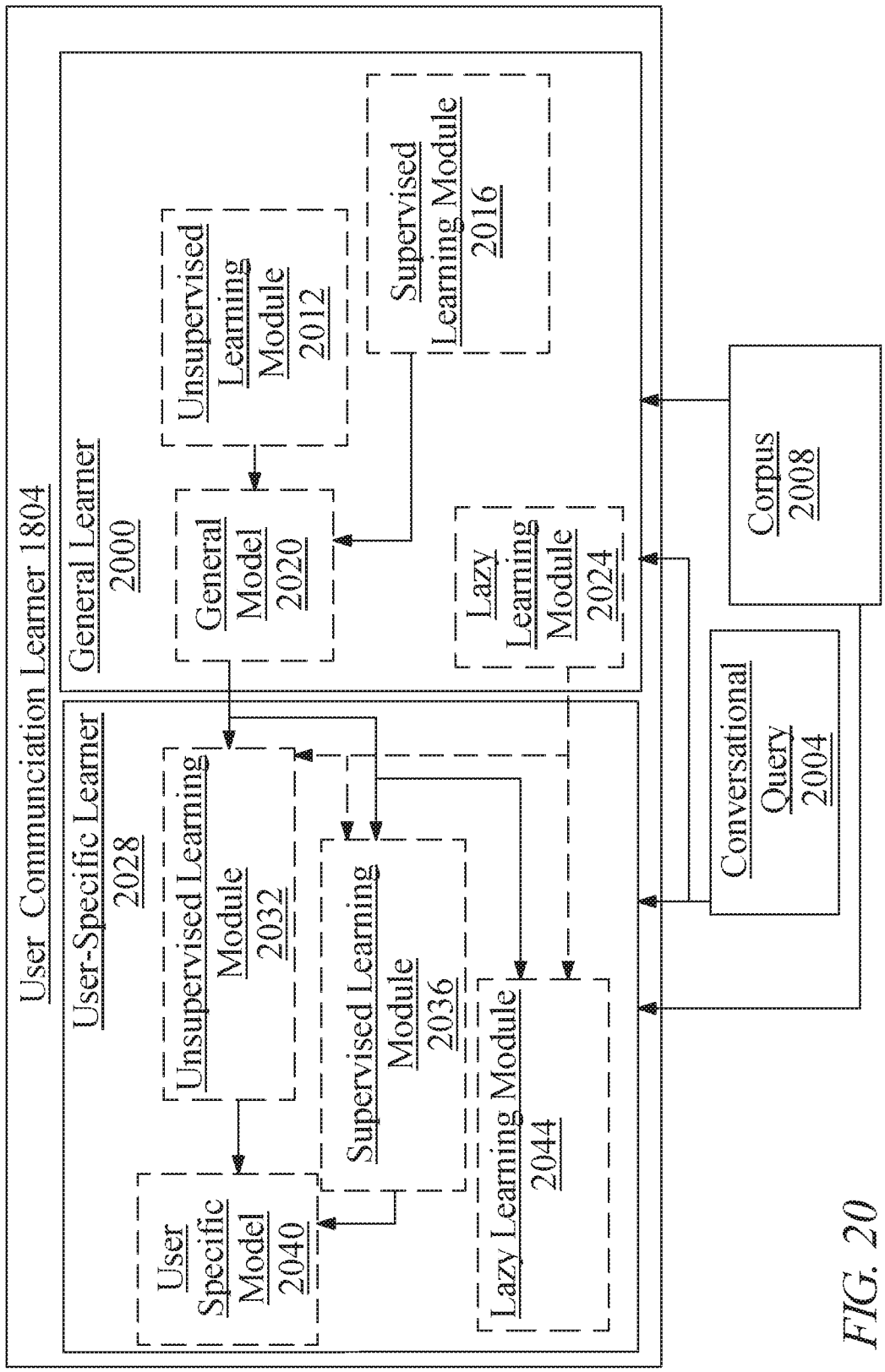
FIG. 20 is a block diagram illustrating an exemplary embodiment of a user communication learner.

Referring now to FIG. 20, an exemplary embodiment of a user communication learner 1804 is illustrated. User communication learner 1804 may include any form of machine-learning learner as described above, implementing any form of language processing and/or machine learning. In an embodiment, user communication learner 1804 may include a general learner 2000; general learner 2000 may be a learner that derives relationships between a conversational query 2004 and correct outputs using a training set that includes, without limitation, a corpus 2008 of previous conversations. Corpus 2008 of previous conversations may be logged by at least a server 104 as conversations take place; user feedback, and/or one or more functions indicating degree of success of a conversation may be used to differentiate between positive input-output pairs to use for training and negative input-output pairs not to use for training. Outputs may include textual strings and/or outputs from any databases, modules, and/or learners as described in this disclosure, including without limitation prognostic labels, prognostic descriptors, ameliorative labels, ameliorative descriptors, user information, or the like; for instance, general learner may determine that some inputs optimally map to textual response outputs, while other inputs map to outputs created by retrieval of module and/or database outputs, such as retrieval of prognostic descriptors, ameliorative descriptors, or the like. General learner 2000 may include any elements suitable for use in any machine-learning module and/or learner as described in this description, including without limitation an unsupervised learning module 2012 and/or a supervised learning module 2016. General learner 2000 may generate a general model 2020 relating conversational inputs to conversational outputs, which may be used to generate conversational outputs; this may be implemented according to any process for implementing machine-learning models and/or language learning models as described in this disclosure. Alternatively or additionally, general learner 2000 may include a lazy learning module 2024. Lazy learning module 2024 may be implemented according to any description in this disclosure for implementation of lazy learning modules.

With continued reference to FIG. 20, user communication learner 1804 may include a user-specific learner 2028, which may generate one or more modules that learn input-output pairs pertaining to communication with a particular user; a user specific learner may initially use input-output pairs established by general learner 2000 and may modify such pairs to match optimal conversation with the particular user by iteratively minimizing an error function. User-specific learner 2028 may include any elements suitable for use in any machine-learning module and/or learner as described in this description, including without limitation an unsupervised learning module 2032 and/or a supervised learning module 2036. User-specific learner 2028 may generate a user-specific model 2040 relating conversational inputs to conversational outputs, which may be used to generate conversational outputs; this may be implemented according to any process for implementing machine-learning models and/or language learning models as described in this disclosure. Alternatively or additionally, user-specific learner 2028 may include a lazy learning module 2044. General learner 2000 and/or user-specific learner 2028 may initialize, prior to training, using one or more records retrieved from default response database 1800 as described above.

Figure 21:
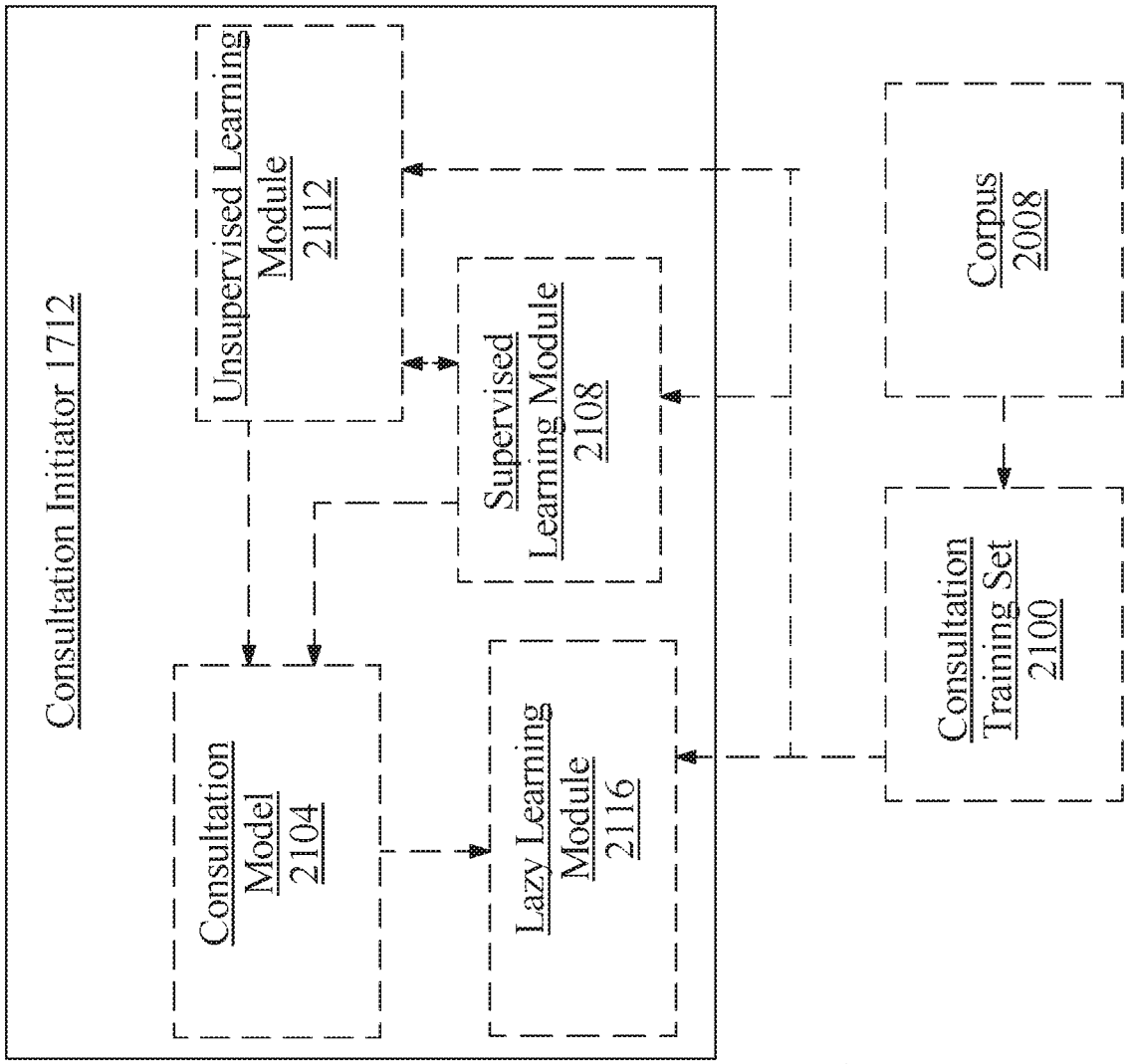
FIG. 21 is a block diagram illustrating an exemplary embodiment of a consultation initiator.

Referring now to FIG. 21, consultation initiator 1708 may alternatively or additionally perform one or more machine-learning operations to detect consultation events. In an embodiment, consultation initiator may perform machine-learning operations using a consultation training set 2100, which may be any training set as described in this disclosure. Consultation training set may, as a non-limiting example, include a plurality of entries, each entry including an input having a word or phrase and an output indicating a category of consultation event; category of consultation event may include no consultation event, hospitalization, and/or consultation with a particular informed advisor such as a medical professional, spiritual advisor, meditation expert, or the like. Consultation training set 2100 may be assembled using, without limitation elements from corpus 2008 of conversations as described above, combined with data describing outcomes for users engaged in such conversations; outcomes may be entered by informed advisors who dealt with outcomes, such as without limitation spiritual informed advisors who treated a user after a given conversation. Additional users of system 100 may alternatively or additionally enter outcome information from records or the like.

Still referring to FIG. 21, consultation initiator 1708 may generate outputs indicating a consultation event, or absence of a consultation event, using at least a user entry and consultation training set. This may be performed according to any machine-learning process as described in this disclosure, such as without limitation any machine-learning process performed by first label learner and/or second label learner. Consultation initiator 1708 may generate a consultation model 2104 relating conversation text to consultation events. For instance, and without limitation, consultation initiator 1708 may be configured to perform one or more supervised learning processes, as described above; supervised learning processes may be performed by a supervised learning module 2108, which may be any supervised learning nodule as described in this disclosure. Inputs to supervised learning module 2108 may include, without limitation words or phrases from corpus 2008, while outputs may include categories of consultation events. Consultation initiator 1708 may perform one or more unsupervised machine-learning processes as described above; unsupervised processes may be performed by an unsupervised learning module 2112, which may be any unsupervised learning nodule as described in this disclosure. Unsupervised learning module 2112 may, for instance, detect correlations between keywords from keyword listing 1716 and/or words or phrases from corpus 2008 that supervised learning module 2108 has associated with consultation events, and other words and phrases, to add additional keywords and/or potential words/phrases that may trigger consultation.

Continuing to view FIG. 21, consultation initiator 1708 may be configured to perform a lazy learning process as a function of the consultation training set 2100 at least a user input. Lazy learning processes may be performed by a lazy learning module 2116 executing on diagnostic engine 108 and/or on another computing device in communication with at least a server 104, which may include any hardware or software module.

In an embodiment, and still viewing FIG. 21, machine-learning processes and/or modules of consultation initiator 1708 may be combined with keyword detection. For instance, machine-learning processes and/or outputs may be triggered upon keyword detection or may operate in parallel or independently from keyword-detection processes. Machine-learning may supplement keyword detection; for instance, and without limitation there may be some keywords that definitely cause consultation events, or there may be keywords that are not enough by themselves to trigger consultation, but may trigger consultation if combined with another detection, which may include a machine-learning output and/or detection of an additional keyword. Machine-learning processes may add keywords when a certain keyword is repeatedly found to be linked to a consultation event, such as without limitation if a linear regression analysis or the like maps a single word or phrase, and/or a combination of one phrase with one prognostic label or one category of prognostic label and/or user datum; such detected keywords may be added to keyword listing 1712 by consultation initiator 1708. As a non-limiting illustration, machine-learning algorithms may determine that if user is currently practicing a form of organized religion such as Christianity and user reports no longer having a belief in God anymore, keyword listing 1712 may create a data entry for that. Consultation initiator 1708 may automatically place an emergency call for one or more consultation events; for instance and without limitation, keyword listing 1712 and/or consultation model 2104 may include flags indicating that a detected consultation event requires an emergency call. User database 828 or any other suitable database may list one or more numbers to place emergency calls to, for instance using voice-over-internet-protocol (VoIP) or other automatic telephonic call protocols.

Figure 22:
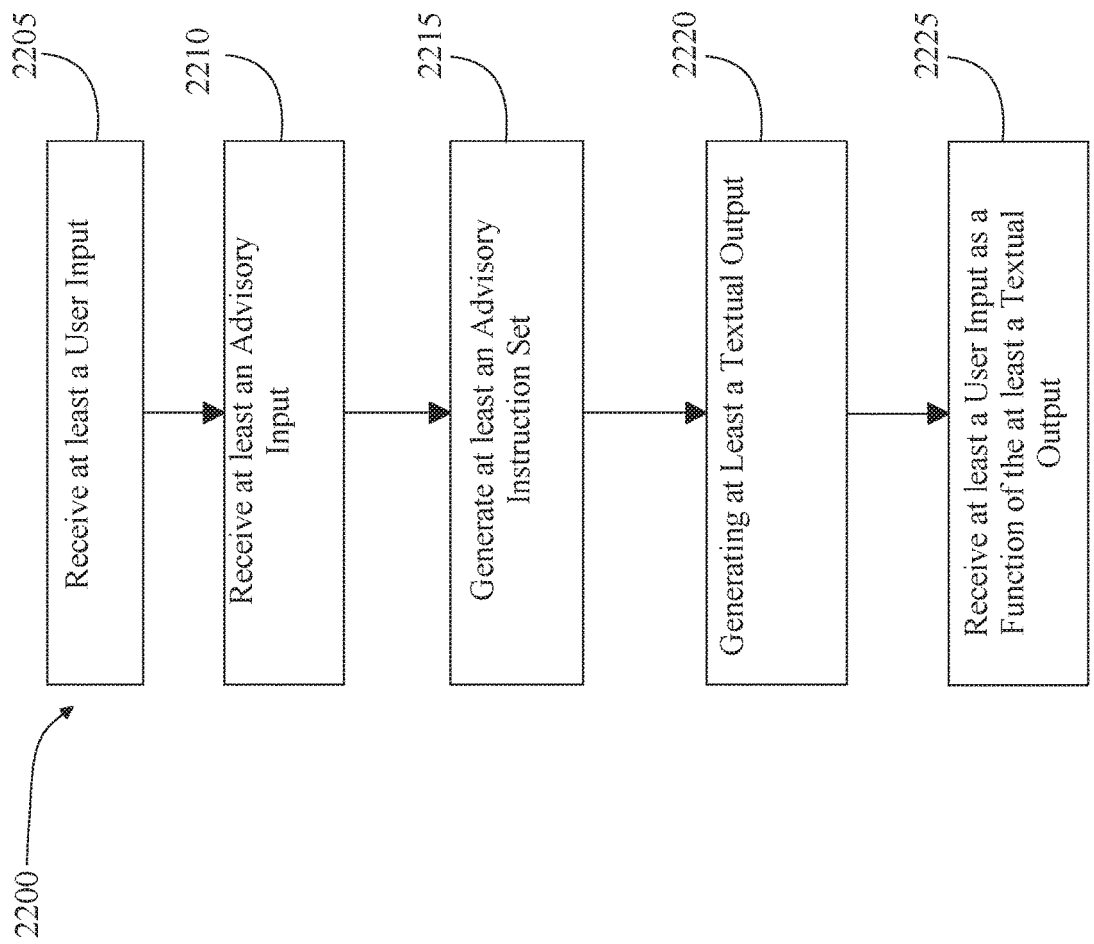
FIG. 22 is a flow diagram illustrating an exemplary method of an artificial intelligence advisory system for textual analysis.

Referring now to FIG. 22, an artificial intelligence method 2200 of textual analysis is illustrated. At step 2205, at least a server 104 receives at least a user input from a user client device. User input may include any of the user input as described above in reference to FIG. 1. User client device includes any of the user client devices as described above in reference to FIG. 1. Receiving at least a user input may be performed using any methodologies as described herein.

With continued reference to FIG. 22, at step 2210 at least a server receives at least an advisory input from an advisor client device. Advisory input may include any of the advisory inputs as described above in reference to FIGS. 1-22. Advisor client device may include any of the advisor client devices as described above in reference to FIGS. 1-22. Receiving at least an advisor input may be performed using any methodologies as described herein.

With continued reference to FIG. 22, at step 2215 at least a server generates at least an advisory instruction set as a function of the at least a user input datum and the at least an advisory input. Generating at least an advisory instruction set may be performed utilizing any of the methodologies as described above in reference to FIGS. 1-22. In an embodiment, generating at least an advisory instruction set may include a diagnostic engine operating on at least a server wherein the diagnostic engine is further configured to record at least a biological extraction from a user and generate a diagnostic output based on the at least a biological extraction. Recording at least a biological extraction from a user and generating at least a diagnostic output based on the at least a biological extraction may be performed utilizing any of the methodologies as described above in reference to FIG. 2. In an embodiment, generating at least an advisory instruction set may include receiving a first training set including a plurality of first data entries, each first data entry of the plurality of first data entries including at least an element of diagnostic output data and at least a correlated advisory label. Generating at least an advisory instruction set may including using a machine-learning algorithm and the first training set. This may be performed utilizing any of the methodologies as described above in reference to FIGS. 1-22.

With continued reference to FIG. 22, generating at least an advisory instruction set may include receiving a second training set including a plurality of second data entries, each second data entry of the plurality of second data entries including at least an element of user input data and at least a correlated second advisory label. Receiving at least a second training set may be performed by any of the methodologies as described above in reference to FIGS. 1-22. Generating at least an advisory instruction set may include using a machine-learning algorithm and the second training data. This may be done utilizing any of the methodologies as described above in reference to FIGS. 1-22.

With continued reference to FIG. 22, generating at least an advisory instruction set may include generating a loss function of user-specific variables and minimizing the loss function. Loss function may include any of the loss functions as described above in reference to FIGS. 1-22. Generating a loss function may be done utilizing any of the methodologies as described above in reference to FIGS. 1-22. User-specific variables may include any of the variables as described above in reference to FIG. 1 and FIG. 16.

With continued reference to FIG. 22, at step 2220 at least a server 104 generates at least a textual output as a function of the at least an advisory instruction set and the at least a user input datum. This may be implemented as described above in reference to FIGS. 1-22. For instance, and without limitation, generating the at least a textual output may include generating at least a query using the at least a user input, and generating the at least a textual output as a function of the at least a query; this may be implemented, without limitation, as described above in reference to FIGS. 1-22. Artificial intelligence advisor 180 and/or a processing module 1704 may determine that the at least a query includes a conversational language query and generating a conversational response using the conversational language query; this may be implemented, without limitation, as described above in reference to FIGS. 1-21. As a further non-limiting example, artificial intelligence advisor 180 and/or a processing module 1704 may determine that the at least a query includes an informational query and generate an informational response using the informational query; this may be implemented, without limitation, as described above in reference to FIGS. 1-21.

Still referring to FIG. 22, artificial intelligence advisor 180 and/or processing module 1704 may submit an informational query to one or more informational resources; for instance, and without limitation, artificial intelligence advisor 180 and/or a processing module 1704 may input the informational query to a first label learner 164 operating on at least a server 104, where the first label learner 164 is designed and configured to generate at least an advisory output as a function of a first training set 128 correlating physiological state data to advisory labels and the informational query, receive, the at least an advisory output from the first label learner 164, and generate the informational response using the at least an advisory output; this may be implemented, without limitation, as described above in reference to FIGS. 1-22. As a further non-limiting example, artificial intelligence advisor 180 and/or a processing module 1704 may input an informational query to a second label leaner 172 operating on at least a server 104, where the second label learner 172 is designed and configured to generate at least a second advisory output as a function of a second training set 148 correlating user input labels to second advisory labels and the informational query, receive the at least a second advisory output from the second label learner 172, and generate the informational response using the at least a second advisory label; this may be implemented, without limitation, as described above in reference to FIGS. 1-22.

With continued reference to FIG. 22, at step 2225 at least a server receives at least a user input as a function of the at least a textual output. At least a user input may include any of the user inputs as described above in reference to FIG. 1. In an embodiment, at least a user input may include a textual response containing a description about a user's progress in reference to a textual output and/or advisory instruction set. In such an instance, textual output and/or advisory instruction set may be updated to reflect information contained within at least a user input. For example, a user input containing mastery of a meditation sequence may be utilized to generate a textual output that includes a harder meditation sequence for user to work on mastering next. In yet another non-limiting example, a user input containing a description of an inability to perform a certain yoga flow sequence may be utilized to update advisory instruction set and/or textual output to include a less challenging yoga flow sequence that user may be able to perform. In yet another non-limiting example, a user input containing an inability to keep with a certain schedule of bible readings may be utilized to generate a new advisory instruction set and/or textual output to contain a bible reading schedule tailored to user's availability and time user may devote to bible reading. In an embodiment, a user input may be verified by artificial intelligence advisory module so as to ensure what user enters is truthful. For example, a user input that includes a textual response indicating user attended a bible study may be verified to see if user really did attend bible study such as by checking with another bible study participant or verifying user's geolocation at the time of the bible study. In such an instance, a user who did attend bible study may receive a textual output congratulating user for attending and offering words of encouragement to keep attending bible study whereas a user who did not attend bible study may receive a textual output that includes words of motivation to encourage user to attend bible study.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 23:
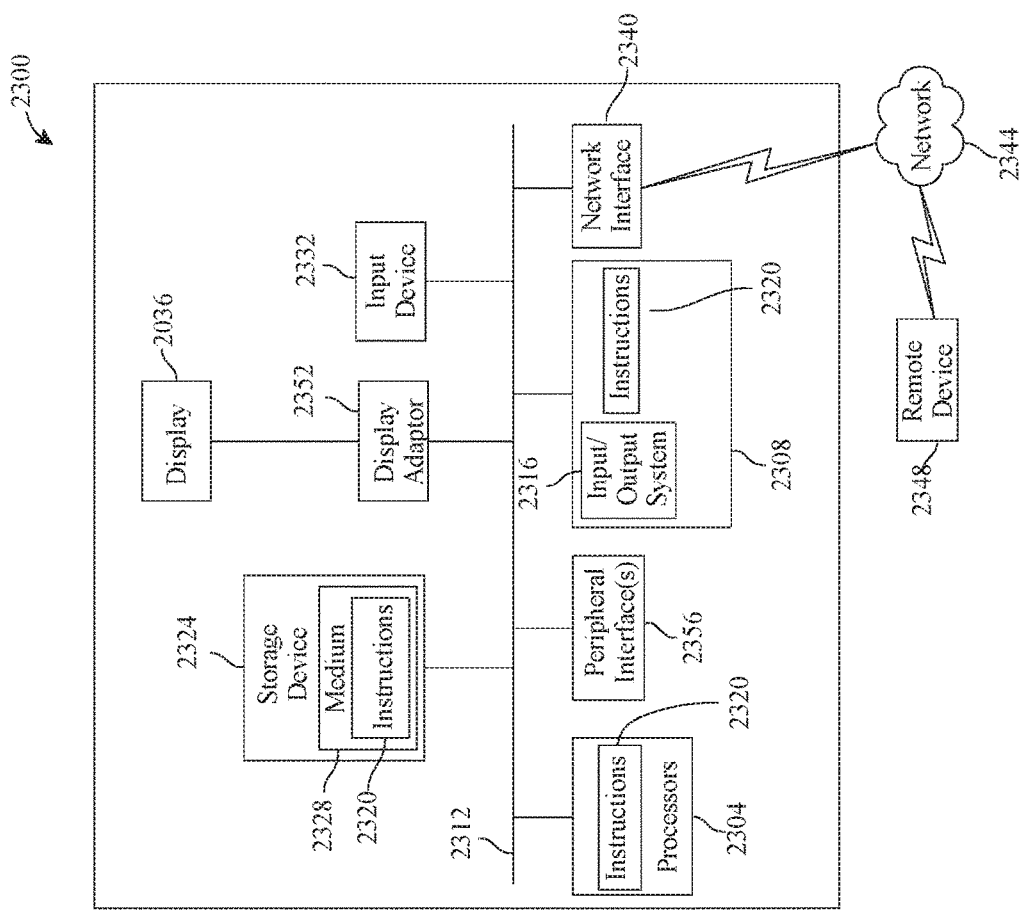
FIG. 23 is a block diagram of a computing system that can be used to implement any one or more of the methodologies disclosed herein and any one or more portions thereof.

FIG. 23 shows a diagrammatic representation of one embodiment of a computing device in the exemplary form of a computer system 2300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2300 includes a processor 2304 and a memory 2308 that communicate with each other, and with other components, via a bus 2312. Bus 2312 may include any of several types of bus structures including, but not limited to, a memory bus, a memory controller, a peripheral bus, a local bus, and any combinations thereof, using any of a variety of bus architectures.

Memory 2308 may include various components (e.g., machine-readable media) including, but not limited to, a random access memory component, a read only component, and any combinations thereof. In one example, a basic input/output system 2316 (BIOS), including basic routines that help to transfer information between elements within computer system 2300, such as during start-up, may be stored in memory 2308. Memory 2308 may also include (e.g., stored on one or more machine-readable media) instructions (e.g., software) 2320 embodying any one or more of the aspects and/or methodologies of the present disclosure. In another example, memory 2308 may further include any number of program modules including, but not limited to, an operating system, one or more application programs, other program modules, program data, and any combinations thereof.

Computer system 2300 may also include a storage device 2324. Examples of a storage device (e.g., storage device 2324) include, but are not limited to, a hard disk drive, a magnetic disk drive, an optical disc drive in combination with an optical medium, a solid-state memory device, and any combinations thereof. Storage device 2324 may be connected to bus 2312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2324 (or one or more components thereof) may be removably interfaced with computer system 2300 (e.g., via an external port connector (not shown)). Particularly, storage device 2324 and an associated machine-readable medium 2328 may provide nonvolatile and/or volatile storage of machine-readable instructions, data structures, program modules, and/or other data for computer system 2300. In one example, software 2320 may reside, completely or partially, within machine-readable medium 2328. In another example, software 2320 may reside, completely or partially, within processor 2304.

Computer system 2300 may also include an input device 2332. In one example, a user of computer system 2300 may enter commands and/or other information into computer system 2300 via input device 2332. Examples of an input device 2332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2332 may be interfaced to bus 2312 via any of a variety of interfaces (not shown) including, but not limited to, a serial interface, a parallel interface, a game port, a USB interface, a FIREWIRE interface, a direct interface to bus 2312, and any combinations thereof. Input device 2332 may include a touch screen interface that may be a part of or separate from display 2336, discussed further below. Input device 2332 may be utilized as a user selection device for selecting one or more graphical representations in a graphical interface as described above.

A user may also input commands and/or other information to computer system 2300 via storage device 2324 (e.g., a removable disk drive, a flash drive, etc.) and/or network interface device 2340. A network interface device, such as network interface device 2340, may be utilized for connecting computer system 2300 to one or more of a variety of networks, such as network 2344, and one or more remote devices 2348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2344, may employ a wired and/or a wireless mode of communication. In general, any network topology may be used. Information (e.g., data, software 2320, etc.) may be communicated to and/or from computer system 2300 via network interface device 2340.

Computer system 2300 may further include a video display adapter 2352 for communicating a displayable image to a display device, such as display device 2336. Examples of a display device include, but are not limited to, a liquid crystal display (LCD), a cathode ray tube (CRT), a plasma display, a light emitting diode (LED) display, and any combinations thereof. Display adapter 2352 and display device 2336 may be utilized in combination with processor 2304 to provide graphical representations of aspects of the present disclosure. In addition to a display device, computer system 2300 may include one or more other peripheral output devices including, but not limited to, an audio speaker, a printer, and any combinations thereof. Such peripheral output devices may be connected to bus 2312 via a peripheral interface 2356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An artificial intelligence advisory system for textual analysis, the system comprising:
   at least a server, wherein the at least a server is configured to:
      receive at least a user input datum from a user client device of a user;
   an advisory module operating on the at least a server, wherein the advisory module is configured to:
      receive at least an advisory input from an advisor client device, wherein the advisory input comprises an advisory recommendation for the user to engage in a specific spiritual practice; and
      generate at least an advisory instruction set as a function of the at least a user input datum and the at least an advisory input;
   a label learner operating on the at least a server, wherein the label learner generates a plurality of advisory labels tailored to the user, wherein generating the plurality of advisory labels comprises:
      determine a correctness probability for each of the plurality of advisory labels;
      filter the plurality of advisory labels as a function of comparing the correctness probability for each of the plurality of advisory labels and a correctness probability threshold; and
   an artificial intelligence advisor operating on the at least a server, wherein the artificial intelligence advisor is configured to:
      generate at least a textual output as a function of the at least an advisory instruction set and the at least a user input datum;
      receive at least a user input as a function of the at least a textual output through the user client device via an instant messaging protocol of the at least a server, wherein the at least a user input includes text;
      verify the at least a user input as a function of a geolocation of the user;
      communicate the at least a user input to the advisory module through a parsing module, wherein the parsing module is configured to classify a polarity of the text of the at least a user input and generate at least a query as a function of the at least a user input;
      determine an informational response for the user as a function of the at least a query;
      detect a consultation event using a consultation model configured to classify the user input to the consultation event, wherein the consultation model is trained with a training data set correlating keywords, from a keyword listing populated with expert data inputs, and phrases from a corpus that a supervised learning module has associated with consultation events; and
      provide the informational response and the consultation event to the user client device through the instant messaging protocol of the at least a server.

2. The artificial intelligence advisory system of claim 1, wherein the at least a server further comprises a diagnostic engine operating on the at least a server wherein the diagnostic engine is further configured to:
   record at least a biological extraction from the user; and
   generate a diagnostic output based on the at least a biological extraction.

3. The artificial intelligence advisory system of claim 2, wherein the advisory module is further configured to receive a first training set including a plurality of first data entries, each first data entry of the plurality of first data entries including at least an element of diagnostic output data and at least a correlated advisory label.

4. The artificial intelligence advisory system of claim 3, wherein the advisory module is further configured to generate the at least an advisory instruction set using a first machine-learning algorithm and the first training data.

5. The artificial intelligence advisory system of claim 1, wherein the advisory module is further configured to receive a second training set including a plurality of second data entries, each second data entry of the plurality of second data entries including at least an element of the user input data and at least a correlated second advisory label.

6. The artificial intelligence advisory system of claim 1, wherein the informational response comprises spiritual life coaching from an informed advisor.

7. The artificial intelligence advisory system of claim 1, wherein generating at least an advisory instruction set further comprises:
   generating a loss function of user-specific variables of the user; and
   minimizing the loss function.

8. The artificial intelligence advisory system of claim 1, wherein the parsing module is further configured to at least a textual output as a function of the at least a query.

9. An artificial intelligence advisory method of textual analysis, the method comprising:
   receiving by at least a server at least a user input datum from a user client device of a user;

receiving by the at least a server at least an advisory input from an advisor client device, wherein the advisory input comprises an advisory recommendation for a user to engage in a specific spiritual practice;

generating by the at least a server at least an advisory instruction set as a function of the at least a user input datum and the at least an advisory input;

generating by the at least a label learner operating on the at least a server plurality of advisory labels tailored to the user, wherein generating the plurality of advisory labels comprises:
  determining a correctness probability for each of the plurality of advisory labels;
  filtering the plurality of advisory labels as a function of comparing the correctness probability for each of the plurality of advisory labels and a correctness probability threshold;

generating by the at least a server at least a textual output as a function of the at least an advisory instruction set and the at least a user input datum;

receiving by the at least a server at least a user input as function of the at least a textual output through the user client device via an instant messaging protocol of the at least a server, wherein the at least a user input includes text;

verifying the at least a user input as a function of a geolocation of the user;

communicating the at least a user input to the advisory module through a parsing module, wherein the parsing module is configured to classify a polarity of the text of the at least a user input and generate at least a query as a function of the at least a user input;

determining an informational response for the user as a function of the at least a query;

detecting a consultation event using a consultation model configured to classify the user input to the consultation event, wherein the consultation model is trained with a training data set correlating keywords, from a keyword listing populated with expert data inputs, and phrases from a corpus that a supervised learning module has associated with consultation events; and providing the informational response and the consultation event to the user client device through the instant messaging protocol of the at least a server.

10. The artificial intelligence advisory method of claim 9, wherein receiving further comprises:
  recording by at least a server at least a biological extraction from the user; and
  generating by at least a server a diagnostic output based on the at least a biological extraction.

11. The artificial intelligence advisory method of claim 10 further comprising receiving a first training set including a plurality of first data entries, each first data entry of the plurality of first data entries including at least an element of diagnostic output data and at least a correlated advisory label.

12. The artificial intelligence advisory method of claim 11 further comprising generating the at least an advisory instruction set using a first machine-learning algorithm and the first training data.

13. The artificial intelligence advisory method of claim 9, wherein receiving further comprises receiving a second training set including a plurality of second data entries, each second data entry of the plurality of second data entries including at least an element of the user input data and at least a correlated second advisory label.

14. The artificial intelligence advisory method of claim 9, wherein the informational response comprises spiritual life coaching from an informed advisor.

15. The artificial intelligence method of claim 9, wherein generating at least an advisory instruction set further comprises:
  generating a loss function of user-specific variables of the user; and
  minimizing the loss function.

16. The artificial intelligence advisory method of claim 9 further comprising:
  generating the at least a textual output as a function of the at least a query.

17. The artificial intelligence advisory system of claim 1, wherein the keyword listing comprises user-specific keywords.

18. The artificial intelligence advisory system of claim 1, wherein the consultation model is further configured to flag a user input correlated to an emergency based consultation event category.

19. The artificial intelligence advisory method of claim 9, wherein the keyword listing comprises user-specific keywords.

20. The artificial intelligence advisory method of claim 9, wherein the consultation model is further configured to flag a user input correlated to an emergency based consultation event category.

* * * * *